United States Patent
Lanter et al.

(10) Patent No.: US 9,434,688 B2
(45) Date of Patent: Sep. 6, 2016

(54) INDOLE DERIVATIVES AS SELECTIVE ANDROGEN RECEPTOR MODULATORS (SARMS)

(71) Applicant: Janssen Pharmaceutica, NV, Beerse (BE)

(72) Inventors: James C Lanter, Audubon, PA (US); Zhihua Sui, Flemington, NJ (US); James J Fiordeliso, Morrisville, PA (US); Weiqin Jiang, Rockville, MD (US); Xuqing Zhang, Spring House, PA (US)

(73) Assignee: Janssen Pharmaceutica NV, Beerse (BE)

( * ) Notice: Subject to any disclaimer, the term of this patent is extended or adjusted under 35 U.S.C. 154(b) by 58 days.

(21) Appl. No.: 14/277,429

(22) Filed: May 14, 2014

(65) Prior Publication Data

US 2014/0249197 A1    Sep. 4, 2014

Related U.S. Application Data

(62) Division of application No. 12/707,295, filed on Feb. 17, 2010, now Pat. No. 8,765,782, which is a division of application No. 12/188,586, filed on Aug. 8, 2008, now Pat. No. 7,705,147, which is a division of application No. 11/096,740, filed on Apr. 1, 2005, now Pat. No. 7,427,682.

(60) Provisional application No. 60/567,717, filed on May 3, 2004.

(51) Int. Cl.
| | | |
|---|---|---|
| *C07D 209/12* | (2006.01) |
| *C07D 209/08* | (2006.01) |
| *C07D 209/30* | (2006.01) |
| *A61K 31/407* | (2006.01) |
| *A61K 31/5025* | (2006.01) |
| *A61K 31/519* | (2006.01) |
| *A61K 31/4985* | (2006.01) |
| *C07D 401/04* | (2006.01) |
| *C07D 405/04* | (2006.01) |
| *C07D 409/04* | (2006.01) |
| *C07D 487/04* | (2006.01) |

(52) U.S. Cl.
CPC ......... *C07D 209/12* (2013.01); *A61K 31/407* (2013.01); *A61K 31/4985* (2013.01); *A61K 31/5025* (2013.01); *A61K 31/519* (2013.01); *C07D 209/08* (2013.01); *C07D 209/30* (2013.01); *C07D 401/04* (2013.01); *C07D 405/04* (2013.01); *C07D 409/04* (2013.01); *C07D 487/04* (2013.01)

(58) Field of Classification Search
CPC  C07D 209/12; C07D 209/08; C07D 209/30; A61K 31/407; A61K 31/5025; A61K 31/519; A61K 31/4985
See application file for complete search history.

(56) References Cited

U.S. PATENT DOCUMENTS

| 4,831,144 A | 5/1989 | Dormoy et al. |
| 6,140,317 A | 10/2000 | Traxler et al. |

FOREIGN PATENT DOCUMENTS

| EP | 0199618 A1 | 10/1986 |
| EP | 1452525 A | 9/2004 |
| JP | 61267581 A | 11/1986 |
| WO | WO 03/020721 A1 | 3/2003 |

OTHER PUBLICATIONS

Basaria, S. et al.: Clinical Review 138: Anabolic-Androgenic Steroid Therapy in the Treatment of Chronic Diseases; the J of Clin Endocrinology & Metabolism 86(11) pp. 5108-5117.
Chacun-Lefevre, L. et al.: Ring closure metathesis of indole 2-carboxylic acid allylamide derivatives; Tetrahedron 58 (2002) pp. 10181-10188.
Dormoy, Jean-Robert and Heymes, Alain; "Synthese Industrielle en serie ellipticine. I." Tetrahedron, vol. 49, No. 14, 1993, pp. 2885-2914. XP002338131.(English abstract only).
Netchitailo, P. et al.: Synthese de flavones et de xanthones dans la serie du benzo[4,5]thiophene; J. Heterocyclic Chem., 15, (1978) pp. 337-342. (English summary only).
Newling, D.W.W.: Anti-androgens in the treatment of prostate cancer; British J. of Urology (1996) 77, pp. 776-784.
Shahidi, N.T. Md.: a Review of the Chemistry, Bioilogical Action, and Clinical Applications of Anabolic-Androgenic Steroids; Clinical Therapeutics, vol. 23, No. 9. (2001) pp. 1355-1390.
Wells, G. et al.: 4-Substituted 4-Hydroxycyclohexa-2,5-dien-1-ones with Selective Activities against Colon and Renal Cancer Cell Lines; J. Med. Chem. (2003) 46, pp. 532-541.
PCT International Search Report and Written Opinion, PCT/US2005/011057, dated Aug. 9, 2005.
International Preliminary Report, PCT/US2005/011057, dated Nov. 7, 2006.

*Primary Examiner* — Sahar Javanmard

(57) ABSTRACT

The present invention is directed to novel indole derivatives, pharmaceutical compositions containing them and their use in the treatment of disorders and conditions modulated by the androgen receptor.

1 Claim, No Drawings

INDOLE DERIVATIVES AS SELECTIVE ANDROGEN RECEPTOR MODULATORS (SARMS)

CROSS REFERENCE TO RELATED APPLICATIONS

This application is a division of U.S. application Ser. No. 12/707,295, filed on Feb. 17, 2010, currently pending, which is a divisional application of U.S. application Ser. No. 12/188,586, filed on Aug. 8, 2008, issued as U.S. Pat. No. 7,705,147, which is a divisional of U.S. application Ser. No. 11/096,740, filed on Apr. 1, 2005, issued as a U.S. Pat. No. 7,427,682 and claims the benefit of U.S. Provisional Application 60/567,717, filed on May 3, 2004, abandoned.

The complete disclosures of the aforementioned related U.S. patent applications are hereby incorporated herein by reference for all purposes.

FIELD OF THE INVENTION

The present invention is directed to novel indole derivatives, pharmaceutical compositions containing them and their use in the treatment of disorders and conditions modulated by the androgen receptor. More particularly, the compounds of the present invention are useful in the treatment of prostate carcinoma, benign prostatic hyperplasia (BPH), hirsutism, alopecia, anorexia nervosa, breast cancer, acne, AIDS, cachexia, as a male contraceptive, and/or as a male performance enhancer.

BACKGROUND OF THE INVENTION

Androgens are the anabolic steroid hormones of animals, controlling muscle and skeletal mass, the maturation of the reproductive system, the development of secondary sexual characteristics and the maintenance of fertility in the male. In women, testosterone is converted to estrogen in most target tissues, but androgens themselves may play a role in normal female physiology, for example, in the brain. The chief androgen found in serum is testosterone, and this is the effective compound in tissues such as the testes and pituitary. In prostate and skin, testosterone is converted to dihydrotestosterone (DHT) by the action of 5α-reductase. DHT is a more potent androgen than testosterone because it binds more strongly to the androgen receptor.

Like all steroid hormones, androgens bind to a specific receptor inside the cells of target tissues, in this case the androgen receptor. This is a member of the nuclear receptor transcription factor family. Binding of androgen to the receptor activates it and causes it to bind to DNA binding sites adjacent to target genes. From there it interacts with coactivator proteins and basic transcription factors to regulate the expression of the gene. Thus, via its receptor, androgens cause changes in gene expression in cells. These changes ultimately have consequences on the metabolic output, differentiation or proliferation of the cell that are visible in the physiology of the target tissue.

Although modulators of androgen receptor function have been employed clinically for some time, both the steroidal (Basaria, S., Wahlstrom, J. T., Dobs, A. S., *J. Clin Endocrinol Metab* (2001), 86, pp 5108-5117; Shahidi, N. T., *Clin Therapeutics*, (2001), 23, pp 1355-1390), and non-steroidal (Newling, D. W., *Br. J. Urol.*, 1996, 77 (6), pp 776-784) compounds have significant liabilities related to their pharmacological parameters, including gynecomastia, breast tenderness and hepatotoxicity. In addition, drug-drug interactions have been observed in patients receiving anticoagulation therapy using coumarins. Finally, patients with aniline sensitivities could be compromised by the metabolites of non-steroidal antiandrogens.

Non-steroidal agonists and antagonists of the androgen receptor are useful in the treatment of a variety of disorders and diseases. More particularly, agonists of the androgen receptor could be employed in the treatment of prostate cancer, benign prostatic hyperplasia, hirsutism in women, alopecia, anorexia nervosa, breast cancer and acne. Antagonists of the androgen receptor could be employed in male contraception, male performance enhancement, as well as in the treatment of cancer, AIDS, cachexia, and other disorders.

Nonetheless, there exists a need for small molecule, non-steroidal antagonists of the androgen receptor. We now describe a novel series of indole derivatives as androgen receptor modulators.

SUMMARY OF THE INVENTION

The present invention is directed to a compound of formula (I)

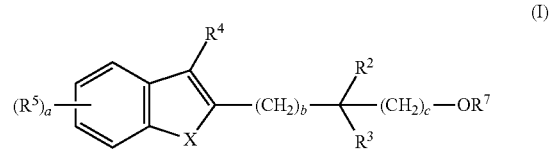

X is selected from the group consisting of O, S and NR$^1$;

R$^1$ is selected from the group consisting of hydrogen, lower alkyl, fluorinated lower alkyl, —SO$_2$-(lower alkyl), —SO$_2$-phenyl, —SO$_2$-tolyl, —(CH$_2$)-(fluorinated lower alkyl), -(lower alkyl)-CN, -(lower alkyl)-C(O)—O-(lower alkyl), -(lower alkyl)-O-(lower alkyl) and -(lower alkyl)-S(O)$_{0-2}$-(lower alkyl);

R$^4$ is selected from the group consisting of hydrogen, halogen, lower alkyl, lower alkenyl, lower alkynyl and cyano; wherein the lower alkyl, lower alkenyl or lower alkynyl is optionally substituted on the terminal carbon atom with —Si(lower alkyl)$_3$;

a is an integer from 0 to 4;

R$^5$ is selected from the group consisting halogen, hydroxy, carboxy, lower alkyl, halogen substituted lower alkyl, lower alkoxy, halogen substituted lower alkoxy, cyano, nitro, amino, lower alkylamino, di(lower alkyl)amino, —C(O)-(lower alkyl), —C(O)-(lower alkoxy), —C(O)—N(R$^A$)$_2$, —S(O)$_{0-2}$-(lower alkyl), —SO$_2$—N(R$^A$)$_2$, —N(R$^A$)—C(O)-(lower alkyl), —N(R$^A$)—C(O)-(halogen substituted lower alkyl) and aryl;

wherein each R$^A$ is independently selected from hydrogen or lower alkyl;

wherein the aryl is optionally substituted with one or more substituents independently selected from halogen, hydroxy, carboxy, lower alkyl, halogen substituted lower alkyl, lower alkoxy, halogen substituted lower alkoxy, cyano, nitro, amino, lower alkylamino or di(lower alkyl)amino;

b is an integer from 0 to 1;

c is an integer from 0 to 1;

R$^7$ is selected from the group consisting of hydrogen, lower alkyl and —Si(lower alkyl)$_3$;

R$^2$ is selected from the group consisting of hydrogen, lower alkyl, halogen substituted lower alkyl and —(CH$_2$)$_{1-4}$—Z—R$^6$;

$R^3$ is selected from the group consisting of lower alkyl, halogen substituted lower alkyl and $-(CH_2)_{1-4}-Z-R^6$;

wherein each Z is independently selected from the group consisting of $-S(O)_{0-2}-$, $-O-$, $-O-C(O)-$, $-NH-$ and $-N$(lower alkyl)-;

wherein each $R^6$ is independently selected from the group consisting of lower alkyl, halogen substituted lower alkyl, lower alkenyl, aryl, aralkyl, biphenyl, cycloalkyl, cycloalkyl-(lower alkyl), heteroaryl and heteroaryl-(lower alkyl);

wherein the cycloalkyl, aryl or heteroaryl group, whether alone or as part of a substituent group is optionally substituted with one or more substituents independently selected from halogen, hydroxy, carboxy, lower alkyl, halogen substituted lower alkyl, lower alkoxy, cyano, nitro, amino, lower alkylamino, di(lower alkyl)amino, $-S(O)_{0-2}$-(lower alkyl) and $-SO_2-N(R^4)_2$;

provided that when Z is O, NH or N(lower alkyl) then $R^6$ is other than lower alkenyl;

provided further that when $R^2$ is methyl, than $R^3$ is other than methyl;

provided further that when X is $NR^1$, $R^1$ is hydrogen or lower alkyl, b is 1, c is 0, $R^4$ is hydrogen, $R^7$ is hydrogen, a is 0 ($R^5$ is absent) and $R^2$ is $CF_3$, then $R^3$ is other than $CF_3$;

provided further that when X is NH, $R^4$ is methyl, b is 0, c is 0, $R^7$ is hydrogen, a is 0 ($R^5$ is absent) and $R^2$ is methyl, then $R^3$ is other than $CF_3$;

provided further that when X is $NR^1$, $R^1$ is hydrogen or lower alkyl, $R^4$ is hydrogen or methyl, b is 0, c is 0, $R^7$ is hydrogen, a is 0 ($R^5$ is absent) and $R^2$ is hydrogen or methyl, then $R^3$ is other than $-(CH_2)_{1-2}-N(R^4)$-(lower alkyl) or $-(CH_2)_3-N(R^4)$-(benzyl);

provided further that when X is NH, $R^4$ is hydrogen, b is 1, c is 0, $R^7$ is hydrogen, a is 0 ($R^5$ is absent) and $R^2$ is hydrogen, then $R^3$ is other than $-(CH_2)-NH$-(lower alkyl);

provided further that when X is NH, $R^4$ is hydrogen, a is 0 ($R^5$ is absent), $R^7$ is hydrogen, b is 0, c is 0 and $R^2$ is $CF_3$, then $R_3$ is other than $-CH_2-O-C(O)-CH_3$;

provided further that when X is NH, $R^4$ is hydrogen, a is 0 ($R^5$ is absent), $R^7$ is hydrogen, b is 1, c is 1 and $R^2$ is hydrogen, then $R_3$ is other than $-CH_2-O-C(O)-CH_3$;

provided further that when X is $NR^1$, $R^1$ is hydrogen or methyl, $R^4$ is hydrogen or methyl, b is 0, c is 0, a is 0 ($R^5$ is absent), $R^7$ is hydrogen and $R^2$ is hydrogen, then $R^3$ is other than $-CH_2-O$-lower alkyl or $-CH_2-O$-benzyl;

provided further that when X is O, $R^4$ is hydrogen, b is 0, c is 0, $R^7$ is hydrogen and $R^2$ is hydrogen, then $R^3$ is other than CH2-O-phenyl, wherein the phenyl is optionally substituted with one to two substituents independently selected from lower alkyl, hydroxy substituted lower alkyl, carboxy and $-C(O)$-(lower alkoxy);

or a pharmaceutically acceptable salt thereof.

The present invention is further directed to a compound of formula (II)

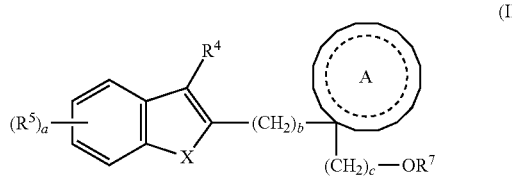

(II)

wherein

X is selected from the group consisting of O, S and $NR^1$;

$R^1$ is selected from the group consisting of hydrogen, lower alkyl, fluorinated lower alkyl, $-SO_2$-(lower alkyl), $-SO_2$-phenyl, $-SO_2$-tolyl, $-(CH_2)-$ (fluorinated lower alkyl), -(lower alkyl)-CN, -(lower alkyl)-C(O)—O-(lower alkyl), -(lower alkyl)-O-(lower alkyl) and -(lower alkyl)-S$(O)_{0-2}$-(lower alkyl);

$R^4$ is selected from the group consisting of hydrogen, halogen, lower alkyl, lower alkenyl, lower alkynyl and cyano; wherein the lower alkyl, lower alkenyl or lower alkynyl is optionally substituted on the terminal carbon atom with $-Si$(lower alkyl)$_3$;

a is an integer from 0 to 4;

$R^5$ is selected from the group consisting halogen, hydroxy, carboxy, lower alkyl, halogen substituted lower alkyl, lower alkoxy, halogen substituted lower alkoxy, cyano, nitro, amino, lower alkylamino, di(lower alkyl)amino, $-C(O)$-(lower alkyl), $-C(O)$-(lower alkoxy), $-C(O)-N(R^4)_2$, $-S(O)_{0-2}$-(lower alkyl), $-SO_2-N(R^4)_2$, $-N(R^4)-C(O)$-(lower alkyl), $-N(R^4)-C(O)$-(halogen substituted lower alkyl) and aryl;

wherein each $R^4$ is independently selected from hydrogen or lower alkyl;

wherein the aryl is optionally substituted with one or more substituents independently selected from halogen, hydroxy, carboxy, lower alkyl, halogen substituted lower alkyl, lower alkoxy, halogen substituted lower alkoxy, cyano, nitro, amino, lower alkylamino or di(lower alkyl)amino;

b is an integer from 0 to 1;

c is an integer from 0 to 1;

$R^7$ is selected from the group consisting of hydrogen, lower alkyl and $-Si$(lower alkyl)$_3$;

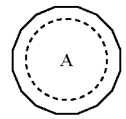

is a four to seven membered, saturated or partially unsaturated ring structure (i.e. not an aromatic ring), containing one to two heteroatoms selected from O, N or S; wherein the four to seven membered, saturated or partially unsaturated ring structure is optionally substituted with a substituent selected from $-(L^1)_{0-1}-R^8$;

wherein $L^1$ is selected from the group consisting of $-(CH_2)_{1-4}-$, $-C(O)-$, $-C(O)-(CH_2)_{1-4}-$, $-C(O)O-$ and $-C(O)O-(CH_2)_{1-4}$;

wherein $R^8$ is selected from the group consisting of aryl and heteroaryl; wherein the aryl or heteroaryl is optionally substituted with one or more substituents independently selected from the group consisting of halogen, hydroxy, carboxy, lower alkyl, halogen substituted lower alkyl, lower alkoxy, cyano, nitro, amino, lower alkylamino, di(lower alkyl)amino, $-S(O)_{0-2}$-(lower alkyl) and $-SO_2-N(R^4)_2$;

provided that when X is NH or $N(CH_3)$, $R^4$ is hydrogen, b is 0, c is 0, $R^7$ is hydrogen or methyl and a is 0 ($R^5$ is absent), then

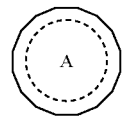

is other than piperidinyl, wherein the piperidinyl is optionally substituted with lower alkyl or aralkyl;

or a pharmaceutically acceptable salt thereof.

The present invention is further directed to a compound of formula (III)

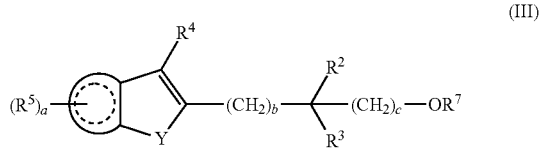

wherein

is a six membered heteroaryl ring structure containing one to two nitrogen atoms;

Y is $NR^1$;

$R^1$ is selected from the group consisting of hydrogen, lower alkyl, fluorinated lower alkyl, $—SO_2$-(lower alkyl), $—SO_2$-phenyl, $—SO_2$-tolyl, $—(CH_2)$-(fluorinated lower alkyl), -(lower alkyl)-CN, -(lower alkyl)-C(O)—O-(lower alkyl), -(lower alkyl)-O-(lower alkyl) and -(lower alkyl)-S$(O)_{0-2}$-(lower alkyl);

$R^4$ is selected from the group consisting of hydrogen, halogen, lower alkyl, lower alkenyl, lower alkynyl and cyano; wherein the lower alkyl, lower alkenyl or lower alkynyl is optionally substituted on the terminal carbon atom with $—Si$(lower alkyl)$_3$;

a is an integer from 0 to 4;

$R^5$ is selected from the group consisting halogen, hydroxy, carboxy, lower alkyl, halogen substituted lower alkyl, lower alkoxy, halogen substituted lower alkoxy, cyano, nitro, amino, lower alkylamino, di(lower alkyl)amino, —C(O)-(lower alkyl), —C(O)-(lower alkoxy), —C(O)—N$(R^4)_2$, —S(O)$_{0-2}$-(lower alkyl), —SO$_2$—N$(R^4)_2$, —N$(R^4)$—C(O)-(lower alkyl), —N$(R^4)$—C(O)-(halogen substituted lower alkyl) and aryl;

wherein each $R^A$ is independently selected from hydrogen or lower alkyl;

wherein the aryl is optionally substituted with one or more substituents independently selected from halogen, hydroxy, carboxy, lower alkyl, halogen substituted lower alkyl, lower alkoxy, halogen substituted lower alkoxy, cyano, nitro, amino, lower alkylamino or di(lower alkyl)amino;

b is an integer from 0 to 1;

c is an integer from 0 to 1;

$R^7$ is selected from the group consisting of hydrogen, lower alkyl and —Si(lower alkyl)$_3$;

$R^2$ is selected from the group consisting of hydrogen, lower alkyl, halogen substituted lower alkyl and —(CH$_2$)$_{1-4}$—Z—R$^6$;

$R^3$ is selected from the group consisting of lower alkyl, halogen substituted lower alkyl and —(CH$_2$)$_{1-4}$—Z—R$^6$;

wherein each Z is independently selected from the group consisting of —S(O)$_{0-2}$—, —O—, —O—C(O)—, —NH— and —N(lower alkyl)-;

wherein each $R^6$ is independently selected from the group consisting of lower alkyl, halogen substituted lower alkyl, lower alkenyl, aryl, aralkyl, biphenyl, cycloalkyl, cycloalkyl-(lower alkyl), heteroaryl and heteroaryl-(lower alkyl);

wherein the cycloalkyl, aryl or heteroaryl group, whether alone or as part of a substituent group is optionally substituted with one or more substituents independently selected from halogen, hydroxy, carboxy, lower alkyl, halogen substituted lower alkyl, lower alkoxy, cyano, nitro, amino, lower alkylamino, di(lower alkyl)amino, —S(O)$_{0-2}$-(lower alkyl) and —SO$_2$—N$(R^A)_2$;

provided that when Z is O, NH or N(lower alkyl) then $R^6$ is other than lower alkenyl;

or a pharmaceutically acceptable salt thereof.

Illustrative of the invention is a pharmaceutical composition comprising a pharmaceutically acceptable carrier and any of the compounds described herein. An illustration of the invention is a pharmaceutical composition made by mixing any of the compounds described herein and a pharmaceutically acceptable carrier. Illustrating the invention is a process for making a pharmaceutical composition comprising mixing any of the compounds described herein and a pharmaceutically acceptable carrier.

Exemplifying the invention are methods of treating disorders and conditions modulated by the androgen receptor in a subject in need thereof comprising administering to the subject a therapeutically effective amount of any of the compounds or pharmaceutical compositions described herein.

An example of the invention is a method for treating an androgen receptor modulated disorder selected from the group consisting of prostate carcinoma, benign prostatic hyperplasia, hirsutism, or for male contraception, in a subject in need thereof comprising administering to the subject an effective amount of any of the compounds or pharmaceutical compositions described herein.

Another example of the invention is the use of any of the compounds described herein in the preparation of a medicament for treating: (a) prostate carcinoma, (b) benign prostatic hyperplasia, (c) hirsutism, (d) alopecia, (e) anorexia nervosa, (f) breast cancer, (g) acne, (h) AIDS, (i) cachexia, for (j) male contraception, or for (k) male performance enhancement, in a subject in need thereof.

DETAILED DESCRIPTION OF THE INVENTION

The present invention is directed to compounds of formula (I), compounds of formula (II) and compounds of formula (III)

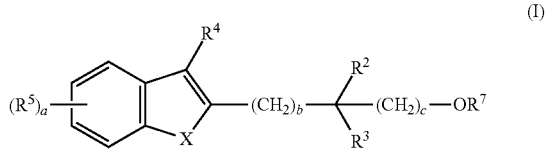

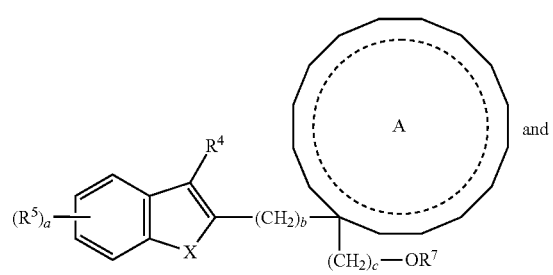

-continued

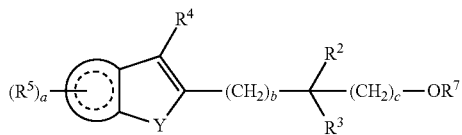
(III)

wherein

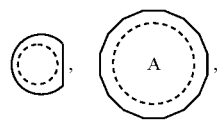

a, b, c, X, Y, $R^2$, $R^3$, $R^4$, $R^5$ and $R^7$ are as herein defined, useful as selective androgen receptor modulators for the treatment of prostate carcinoma, benign prostatic hyperplasia (BPH), hirsutism, alopecia, anorexia nervosa, breast cancer, acne, AIDS, cachexia, as a male contraceptive, and/or as a male performance enhancer.

In an embodiment, the present invention is directed to compounds of formula (I) wherein X is selected from the group consisting of O, S and $NR^1$;

$R^1$ is selected from the group consisting of hydrogen, lower alkyl, fluorinated lower alkyl, —$SO_2$-(lower alkyl), —($CH_2$)-(fluorinated lower alkyl), -(lower alkyl)-CN, -(lower alkyl)-C(O)—O-(lower alkyl), -(lower alkyl)-O-(lower alkyl) and -(lower alkyl)-$S(O)_{0-2}$-(lower alkyl);

$R^4$ is selected from the group consisting of hydrogen, halogen, lower alkyl, lower alkenyl, lower alkynyl and cyano; wherein the lower alkyl, lower alkenyl or lower alkynyl is optionally substituted on the terminal carbon atom with —Si(lower alkyl)$_3$;

a is an integer from 0 to 4;

$R^5$ is selected from the group consisting halogen, hydroxy, carboxy, lower alkyl, halogen substituted lower alkyl, lower alkoxy, halogen substituted lower alkoxy, cyano, nitro, amino, lower alkylamino, di(lower alkyl)amino, —C(O)-(lower alkyl), —C(O)-(lower alkoxy), —C(O)—$N(R^4)_2$, —$S(O)_{0-2}$-(lower alkyl), —$SO_2$—$N(R^4)_2$, —$N(R^4)$—C(O)-(lower alkyl), —$N(R^4)$—C(O)-(halogen substituted lower alkyl) and aryl;

wherein each $R^4$ is independently selected from hydrogen or lower alkyl;

wherein the aryl is optionally substituted with one or more substituents independently selected from halogen, hydroxy, carboxy, lower alkyl, halogen substituted lower alkyl, lower alkoxy, halogen substituted lower alkoxy, cyano, nitro, amino, lower alkylamino or di(lower alkyl)amino;

b is an integer from 0 to 1;

c is an integer from 0 to 1;

$R^7$ is selected from the group consisting of hydrogen, lower alkyl and —Si(lower alkyl)$_3$;

$R^2$ is selected from the group consisting of hydrogen, lower alkyl, halogen substituted lower alkyl and —($CH_2$)$_{1-4}$—Z—$R^6$;

$R^3$ is selected from the group consisting of lower alkyl, halogen substituted lower alkyl and —($CH_2$)$_{1-4}$—Z—$R^6$;

wherein each Z is independently selected from the group consisting of —$S(O)_{0-2}$—, —O—, —O—C(O)—, —NH— and —N(lower alkyl)-;

wherein each $R^6$ is independently selected from the group consisting of lower alkyl, halogen substituted lower alkyl, lower alkenyl, aryl, aralkyl, biphenyl, cycloalkyl, cycloalkyl-(lower alkyl), heteroaryl and heteroaryl-(lower alkyl);

wherein the cycloalkyl, aryl or heteroaryl group, whether alone or as part of a substituent group is optionally substituted with one or more substituents independently selected from halogen, hydroxy, carboxy, lower alkyl, halogen substituted lower alkyl, lower alkoxy, cyano, nitro, amino, lower alkylamino, di(lower alkyl)amino, —$S(O)_{0-2}$-(lower alkyl) and —$SO_2$—$N(R^4)_2$;

and pharmaceutically acceptable salts thereof.

In an embodiment, the present invention is directed to compounds of formula (II) wherein X is selected from the group consisting of O, S and $NR^1$;

$R^1$ is selected from the group consisting of hydrogen, lower alkyl, fluorinated lower alkyl, —$SO_2$-(lower alkyl), —($CH_2$)-(fluorinated lower alkyl), —(lower alkyl)-CN, -(lower alkyl)-C(O)—O-(lower alkyl), -(lower alkyl)-O-(lower alkyl) and -(lower alkyl)-$S(O)_{0-2}$-(lower alkyl);

$R^4$ is selected from the group consisting of hydrogen, halogen, lower alkyl, lower alkenyl, lower alkynyl and cyano; wherein the lower alkyl, lower alkenyl or lower alkynyl is optionally substituted on the terminal carbon atom with —Si(lower alkyl)$_3$;

a is an integer from 0 to 4;

$R^5$ is selected from the group consisting halogen, hydroxy, carboxy, lower alkyl, halogen substituted lower alkyl, lower alkoxy, halogen substituted lower alkoxy, cyano, nitro, amino, lower alkylamino, di(lower alkyl)amino, —C(O)-(lower alkyl), —C(O)-(lower alkoxy), —C(O)—$N(R^4)_2$, —$S(O)_{0-2}$-(lower alkyl), —$SO_2$—$N(R^4)_2$, —$N(R^4)$—C(O)-(lower alkyl), —$N(R^4)$—C(O)-(halogen substituted lower alkyl) and aryl;

wherein each $R^4$ is independently selected from hydrogen or lower alkyl;

wherein the aryl is optionally substituted with one or more substituents independently selected from halogen, hydroxy, carboxy, lower alkyl, halogen substituted lower alkyl, lower alkoxy, halogen substituted lower alkoxy, cyano, nitro, amino, lower alkylamino or di(lower alkyl)amino;

b is an integer from 0 to 1;

c is an integer from 0 to 1;

$R^7$ is selected from the group consisting of hydrogen, lower alkyl and —Si(lower alkyl)$_3$;

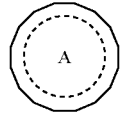

is a four to seven membered saturated or partially unsaturated ring structure, containing one to two heteroatoms selected from O, N or S; wherein the four to seven membered saturated or partially unsaturated ring structure is optionally substituted with a substituent selected from -($L^1$)$_{0-1}$-$R^8$;

wherein $L^1$ is selected from the group consisting of —($CH_2$)$_{1-4}$—, —C(O)—, —C(O)—($CH_2$)$_{1-4}$—, —C(O)O— and —C(O)O—($CH_2$)$_{1-4}$;

wherein $R^8$ is selected from the group consisting of aryl and heteroaryl; wherein the aryl or heteroaryl is optionally substituted with one or more substituents independently selected from the group consisting of halogen, hydroxy, carboxy, lower alkyl, halogen substituted lower alkyl, lower alkoxy, cyano, nitro, amino, lower alkylamino, di(lower alkyl)amino, —S(O)$_{0-2}$-(lower alkyl) and —SO$_2$—N(R$^A$)$_2$;

and pharmaceutically acceptable salts thereof.

In an embodiment, the present invention is directed to compounds of formula (III) wherein

is a six membered heteroaryl ring structure containing one to two nitrogen atoms;

Y is NR$^1$;

R$^1$ is selected from the group consisting of hydrogen, lower alkyl, fluorinated lower alkyl, —SO$_2$-(lower alkyl), —(CH$_2$)-(fluorinated lower alkyl), -(lower alkyl)-CN, -(lower alkyl)-C(O)—O-(lower alkyl), -(lower alkyl)-O-(lower alkyl) and -(lower alkyl)-S(O)$_{0-2}$-(lower alkyl);

R$^4$ is selected from the group consisting of hydrogen, halogen, lower alkyl, lower alkenyl, lower alkynyl and cyano; wherein the lower alkyl, lower alkenyl or lower alkynyl is optionally substituted on the terminal carbon atom with —Si(lower alkyl)$_3$;

a is an integer from 0 to 4;

R$^5$ is selected from the group consisting halogen, hydroxy, carboxy, lower alkyl, halogen substituted lower alkyl, lower alkoxy, halogen substituted lower alkoxy, cyano, nitro, amino, lower alkylamino, di(lower alkyl)amino, —C(O)-(lower alkyl), —C(O)-(lower alkoxy), —C(O)—N(R$^A$)$_2$, —S(O)$_{0-2}$-(lower alkyl), —SO$_2$—N(R$^A$)$_2$, —N(R$^A$)—C(O)-(lower alkyl), —N(R$^A$)—C(O)-(halogen substituted lower alkyl) and aryl;

wherein each R$^A$ is independently selected from hydrogen or lower alkyl;

wherein the aryl is optionally substituted with one or more substituents independently selected from halogen, hydroxy, carboxy, lower alkyl, halogen substituted lower alkyl, lower alkoxy, halogen substituted lower alkoxy, cyano, nitro, amino, lower alkylamino or di(lower alkyl)amino;

b is an integer from 0 to 1;

c is an integer from 0 to 1;

R$^7$ is selected from the group consisting of hydrogen, lower alkyl and —Si(lower alkyl)$_3$;

R$^2$ is selected from the group consisting of hydrogen, lower alkyl, halogen substituted lower alkyl and —(CH$_2$)$_{1-4}$—Z—R$^6$;

R$^3$ is selected from the group consisting of lower alkyl, halogen substituted lower alkyl and —(CH$_2$)$_{1-4}$—Z—R$^6$;

wherein each Z is independently selected from the group consisting of —S(O)$_{0-2}$—, —O—, —O—C(O)—, —NH— and —N(lower alkyl)-;

wherein each R$^6$ is independently selected from the group consisting of lower alkyl, halogen substituted lower alkyl lower alkenyl, aryl, aralkyl, biphenyl, cycloalkyl, cycloalkyl-(lower alkyl), heteroaryl and heteroaryl-(lower alkyl);

wherein the cycloalkyl, aryl or heteroaryl group, whether alone or part of a substituent group is optionally substituted with one or more substituents independently selected from halogen, hydroxy, carboxy, lower alkyl, halogen substituted lower alkyl, lower alkoxy, cyano, nitro, amino, lower alkylamino, di(lower alkyl)amino, —S(O)$_{0-2}$-(lower alkyl) and —SO$_2$—N(R$^A$)$_2$;

and pharmaceutically acceptable salts thereof.

In an embodiment of the present invention is a compound of formula (Ia)

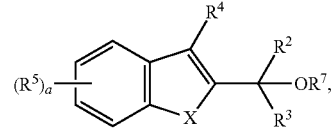

i.e. a compound of formula (I) wherein b and c are each 0. In an embodiment of the present invention is a compound of formula (Ia) wherein R$^2$ is other than —(CH$_2$)$_{1-4}$—Z—R$^6$. In another embodiment of the present invention is a compound of formula (Ia) wherein R$^3$ is selected from —(CH$_2$)$_{1-4}$—Z—R$^6$.

In an embodiment of the present invention is a compound of formula (Ia) wherein R$^3$ is —(CH$_2$)$_{1-4}$—S(O)$_{0-2}$—R$^6$. In another embodiment of the present invention is a compound of formula (Ia) wherein R$^3$ is selected from —(CH$_2$)$_{1-4}$—NH—R$^6$. or —(CH$_2$)$_{1-4}$—N(lower alkyl)-R$^6$. In yet another embodiment of the present invention is a compound of formula (Ia) wherein R$^3$ is selected from —(CH$_2$)$_{1-4}$—O—R$^6$. or —(CH$_2$)$_{1-4}$—O—C(O)—R$^6$.

In an embodiment of the present invention

is pyridyl. In another embodiment of the present invention,

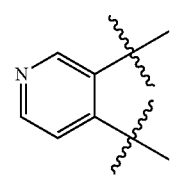

is selected from the group consisting of

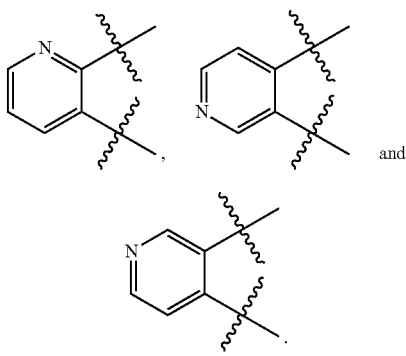

Preferably,

is selected from the group consisting of

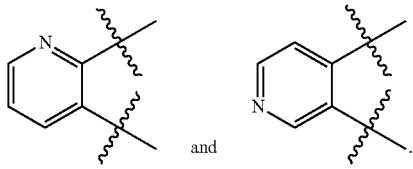 [SMILES: *c1cccnc1* ; *c1ccncc1*]

and

In another embodiment of the present invention,

is selected from the group consisting of

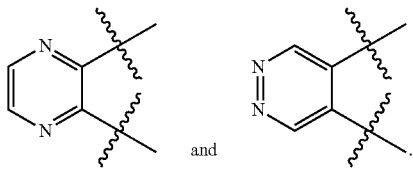 [SMILES: *c1nccnc1* ; *c1cnncc1*]

and

In an embodiment of the present invention is a compound of formula (III) wherein $R^3$ is —$(CH_2)_{1-4}$—$S(O)_{0-2}$—$R^6$. In another embodiment of the present invention is a compound of formula (III) wherein $R^3$ is selected from —$(CH_2)_{1-4}$—NH—$R^6$. or —$(CH_2)_{1-4}$—N(lower alkyl)-$R^6$. In yet another embodiment of the present invention is a compound of formula (III) wherein $R^3$ is selected from —$(CH_2)_{1-4}$—O—$R^6$. or —$(CH_2)_{1-4}$—O—C(O)—$R^6$.

In an embodiment of the present invention

is a four to seven membered saturated or partially unsaturated ring structure, containing one to two heteroatoms selected from O, N or S; wherein the four to seven membered saturated or partially unsaturated ring structure is optionally substituted with a substituent selected from -($L^1$)$_{0-1}$-$R^8$.

In an embodiment of the present invention $L^1$ is selected from the group consisting of —$(CH_2)_{1-4}$—, —C(O)— and —C(O)—$(CH_2)_{1-4}$—.

In an embodiment of the present invention $R^8$ is selected from the group consisting of aryl and heteroaryl; wherein the aryl or heteroaryl is optionally substituted with one or more substituents independently selected from the group consisting of halogen, hydroxy, carboxy, lower alkyl, halogen substituted lower alkyl, lower alkoxy, cyano, nitro, amino, lower alkylamino, di(lower alkyl)amino, —$S(O)_{0-2}$-(lower alkyl) and —$SO_2$—$N(R^A)_2$.

In an embodiment of the present invention

is selected from the group consisting of tetrahydro-thienyl, tetrahydro-thiopyranyl and piperidinyl.

In another embodiment of the present invention

is piperidinyl, wherein the piperidinyl is optionally substituted with a group selected from aryl, aryl-carbonyl, aralkyl or aralkyl-carbonyl, and wherein the aryl or aralkyl substituent on the piperidinyl is optionally substituted with one or more, preferably one to two, more preferably one, substituent selected from the group consisting of halogen, lower alkyl, lower alkoxy, trifluoromethyl, trifluoromethoxy and lower alkyl-sulfonyl.

In yet another embodiment of the present invention

is piperidinyl, wherein the piperidinyl is optionally substituted with a group selected from benzyl, fluoro-benzyl, chloro-benzyl, dichloro-benzyl, methyl-benzyl, methoxy-benzyl, trifluoromethyl-benzyl, t-butyl-benzyl, methylsulfonyl-benzyl, benzyloxy-carbonyl or chlorophenyl-carbonyl.

In an embodiment of the present invention a is an integer from 0 to 3. Preferably, a is an integer from 0 to 2. More preferably, a is an integer from 1 to 2.

In an embodiment of the present invention b is 0 and c is 1. In another embodiment of the present invention b is 1 and c is 0. In yet another embodiment of the present invention b is 0 and c is 0.

In an embodiment of the present invention X is O or $NR^1$. Preferably, X is $NR^1$.

In an embodiment of the present invention $R^1$ is selected from the group consisting of hydrogen, lower alkyl, fluorinated lower alkyl, -(lower alkyl)-CN, (lower alkyl)-O-(lower alkyl), (lower alkyl)-$S(O)_{0-2}$-(lower alkyl), —$SO_2$-(lower alkyl), —$SO_2$-phenyl and —$SO_2$-toyl.

In another embodiment of the present invention $R^1$ is selected from the group consisting of hydrogen, lower alkyl, fluorinated lower alkyl, -(lower alkyl)-CN, (lower alkyl)-O-(lower alkyl), (lower alkyl)-$S(O)_{0-2}$-(lower alkyl) and —$SO_2$-(lower alkyl).

In another embodiment of the present invention $R^1$ is selected from the group consisting of hydrogen, lower alkyl, halogentated lower alkyl, lower alkyl-sulfonyl, lower alkoxy-lower alkyl, cyano-lower alkyl and lower alkyl-thio-lower alkyl. Preferably, $R^1$ is selected from the group consisting of hydrogen, methyl, ethyl, 2,2,2-trifluoroethyl, methyl-sulfonyl, methoxy-methyl, cyano-methyl and methyl-thio-methyl.

In an embodiment of the present invention $R^2$ is selected from the group consisting of hydrogen, lower alkyl, halogen substituted lower alkyl and —$(CH_2)$—Z—$R^6$, wherein Z is selected from the group consisting of —$S(O)_{0-2}$—, preferably Z is —S—. Preferably $R^2$ is selected from the group consisting of hydrogen, methyl, ethyl, trifluoromethyl and —$CH_2$—S-ethyl.

In another embodiment of the present invention $R^2$ is selected from the group consisting of hydrogen and lower alkyl. Preferably, $R^2$ is selected from the group consisting of hydrogen and methyl. More preferably, $R^2$ is methyl. In another embodiment, $R^2$ is selected from the group consisting of hydrogen and trifluoromethyl.

In an embodiment of the present invention $R^3$ is selected from the group consisting of lower alkyl, halogen substituted lower alkyl, —$(CH_2)_{0-2}$—Z—$R^6$.

In another embodiment of the present invention $R^3$ is selected from the group consisting of methyl, chloromethyl, trifluoromethyl, —$CH_2$—O-(4-cyanophenyl), —$CH_2$—O-(3-nitrophenyl), —$CH_2$-(3-trifluoromethyl-4-cyanophenyl), —S-methyl, —S-isopropyl, —S-cyclohexyl, —S-phenyl, —S-(4-chlorophenyl), —S-(4-fluorophenyl), —S-(3,4-dichlorophenyl), —S-(4-aminophenyl), —$SO_2$-(4-chlorophenyl), —$SO_2$-(3,4-dichlorophenyl), —$CH_2$—S-methyl, —$CH_2$—S-ethyl, —$CH_2$—S-butyl, —$CH_2$—S-propyl, —$CH_2$—S-isopropyl, —$CH_2$—S-isobutyl, —$CH_2$—S-allyl, —$CH_2$—S-phenyl, —$CH_2$—S-(2-chlorophenyl), —$CH_2$—S-(4-chlorophenyl), —$CH_2$—S-(4-fluorophenyl), —$CH_2$—S-(4-methoxyphenyl), —$CH_2$—S-(4-carboxyphenyl), —$CH_2$—S-(4-hydroxyphenyl), —$CH_2$—S-(4-nitrophenyl), —$CH_2$—S-(4-aminophenyl), —$CH_2$—S-(4-dimethylamino-phenyl), —$CH_2$—S-(3,4-dichlorophenyl), —$CH_2$—S-(2,2,2-trifluoroethyl), —$CH_2$—S-benzyl, —$CH_2$—S-cyclopentyl, —$CH_2$—S-cyclohexyl, —$CH_2$—S-(2-thienyl-methyl), —$CH_2$—S-(2-furyl-methyl), —$CH_2$—S-(2-pyridyl-methyl), —$CH_2$—SO-ethyl, —$CH_2$—SO-phenyl, —$CH_2$—SO-(3,4-dichlorophenyl), —$CH_2$—SO-(2,2,2-trifluoroethyl), —$CH_2$—SO-benzyl, —$CH_2$—$SO_2$-methyl, —$CH_2$—$SO_2$-ethyl, —$CH_2$—$SO_2$-propyl, —$CH_2$—$SO_2$-(4-fluorophenyl), —$CH_2$—$SO_2$-(4-hydroxyphenyl), —$CH_2$—$SO_2$-(4-aminophenyl), —$CH_2$—$SO_2$-(4-dimethylamino-phenyl), —$CH_2$—$SO_2$-(4-methoxyphenyl), —$CH_2$—$SO_2$-(2,2,2-trifluoroethyl), —$CH_2$—$SO_2$-benzyl, —$CH_2CH_2$—S-methyl, —$CH_2CH_2$—SO-methyl, —$CH_2CH_2$—$SO_2$-methyl, —$CH_2$—O—C(O)-(2-chlorophenyl), —$CH_2$—O—C(O)-(3-chlorophenyl), —$CH_2$—O—C(O)-(4-chlorophenyl), —$CH_2$—O—C(O)-(4-fluorophenyl), —$CH_2$—O—C(O)-(4-nitrophenyl), —$CH_2$—O—C(O)-(4-methyl-phenyl), —$CH_2$—O—C(O)-(4-methoxyphenyl), —$CH_2$—O—C(O)-(2-trifluoro-methyl-phenyl), —$CH_2$—O—C(O)-(4-t-butyl-phenyl), —$CH_2$—O—C(O)-phenyl, —$CH_2$—O—C(O)-(3,4-dichloro-phenyl), —$CH_2$—O—C(O)-(2,6-dichloro-phenyl), —$CH_2$—O—C(O)-(4-dimethyl-amino-phenyl), —$CH_2$—O—C(O)-(4-biphenyl), —$CH_2$—O—C(O)-(2-pyridyl), —$CH_2$—O—C(O)-(3-pyridyl) and —$CH_2$—O—C(O)-(5-chloro-6-benzothienyl).

In another embodiment of the present invention $R^3$ is selected from the group consisting of methyl, chloromethyl, trifluoromethyl, —S-methyl, —S-isopropyl, —S-cyclohexyl, —S-phenyl, —S-(4-chlorophenyl), —S-(4-fluorophenyl), —S-(3,4-dichlorophenyl), —S-(4-aminophenyl), —$SO_2$-(4-chlorophenyl), —$SO_2$-(3,4-dichlorophenyl), —$CH_2$—S-methyl, —$CH_2$—S-ethyl, —$CH_2$—S-butyl, —$CH_2$—S-propyl, —$CH_2$—S-isopropyl, —$CH_2$—S-isobutyl, —$CH_2$—S-allyl, —$CH_2$—S-phenyl, —$CH_2$—S-(2-chlorophenyl), —$CH_2$—S-(4-chlorophenyl), —$CH_2$—S-(4-fluorophenyl), —$CH_2$—S-(4-methoxyphenyl), —$CH_2$—S-(4-carboxyphenyl), —$CH_2$—S-(4-hydroxyphenyl), —$CH_2$—S-(4-nitrophenyl), —$CH_2$—S-(4-aminophenyl), —$CH_2$—S-(4-dimethylamino-phenyl), —$CH_2$—S-(3,4-dichlorophenyl), —$CH_2$—S-(2,2,2-trifluoroethyl), —$CH_2$—S-benzyl, —$CH_2$—S-cyclopentyl, —$CH_2$—S-cyclohexyl, —$CH_2$—S-(2-thienyl-methyl), —$CH_2$—S-(2-furyl-methyl), —$CH_2$—S-(2-pyridyl-methyl), —$CH_2$—SO-ethyl, —$CH_2$—SO-phenyl, —$CH_2$—SO-(3,4-dichlorophenyl), —$CH_2$—SO-(2,2,2-trifluoroethyl), —$CH_2$—SO-benzyl, —$CH_2$—$SO_2$-methyl, —$CH_2$—$SO_2$-ethyl, —$CH_2$—$SO_2$-propyl, —$CH_2$—$SO_2$-(4-fluorophenyl), —$CH_2$—$SO_2$-(4-hydroxyphenyl), —$CH_2$—$SO_2$-(4-aminophenyl), —$CH_2$—$SO_2$-(4-dimethylamino-phenyl), —$CH_2$—$SO_2$-(4-methoxyphenyl), —$CH_2$—$SO_2$-(2,2,2-trifluoroethyl), —$CH_2$—$SO_2$-benzyl, —$CH_2CH_2$—S-methyl, —$CH_2CH_2$—SO-methyl, —$CH_2CH_2$—$SO_2$-methyl, —$CH_2$—O—C(O)-(2-chlorophenyl), —$CH_2$—O—C(O)-(3-chlorophenyl), —$CH_2$—O—C(O)-(4-chlorophenyl), —$CH_2$—O—C(O)-(4-fluorophenyl), —$CH_2$—O—C(O)-(4-nitrophenyl), —$CH_2$—O—C(O)-(4-methyl-phenyl), —$CH_2$—O—C(O)-(4-methoxy-phenyl), —$CH_2$—O—C(O)-(2-trifluoro-methyl-phenyl), —$CH_2$—O—C(O)-(4-t-butyl-phenyl), —$CH_2$—O—C(O)-phenyl, —$CH_2$—O—C(O)-(3,4-dichloro-phenyl), —$CH_2$—O—C(O)-(2,6-dichloro-phenyl), —$CH_2$—O—C(O)-(4-dimethyl-amino-phenyl), —$CH_2$—O—C(O)-(4-biphenyl), —$CH_2$—O—C(O)-(2-pyridyl), —$CH_2$—O—C(O)-(3-pyridyl) and —$CH_2$—O—C(O)-(5-chloro-6-benzothienyl).

In another embodiment of the present invention $R^3$ is selected from the group consisting of —$CH_2$—$S(O)_{0-2}$—$R^6$, wherein $R^6$ is selected from the group consisting of lower alkyl, halogen substituted lower alkyl, aryl, aralkyl, biphenyl, heteroaryl and heteroaryl-(lower alkyl); wherein the aryl or heteroaryl group, whether alone or as part of a substituent group is optionally substituted with one or more, preferably, one to three, substituents independently selected from halogen, hydroxy, carboxy, lower alkyl, halogen substituted lower alkyl, lower alkoxy, cyano, nitro, amino, lower alkylamino, di(lower alkyl)amino, —$S(O)_{0-2}$-(lower alkyl) and —$SO_2$—$N(R^A)_2$; and wherein each $R^A$ is independently selected from hydrogen or lower alkyl. Preferably, $R^3$ is selected from the group consisting of —$CH_2$—$S(O)_{0-2}$-(lower alkyl), more preferably, $R^3$ is selected from the group consisting of —$CH_2$—S-(lower alkyl) and —$CH_2$—$SO_2$-(lower alkyl).

In an embodiment of the present invention Z is selected from the group consisting of —$S(O)_{0-2}$—, —O— and —O—C(O)—. In another embodiment of the present invention Z is selected from the group consisting of —$S(O)_{0-2}$— and —O—C(O)—. In another embodiment of the present invention Z is selected from the group consisting of —S—, —SO— and —$SO_2$—, preferably Z is selected from the group consisting of —S— and —$SO_2$—. In another embodiment of the present invention Z is selected from the group consisting of —NH— and —N(lower alkyl)-. In yet another embodiment of the present invention Z is selected from the group consisting of —O— and —O—C(O)—, preferably Z is —O—C(O)—.

In an embodiment of the present invention $R^6$ is selected from the group consisting of lower alkyl, halogen substituted lower alkyl, lower alkenyl, cycloalkyl, aryl, aralkyl, biphenyl, heteroaryl and heteroaryl-(lower alkyl)-; wherein the aryl or heteroaryl, whether alone or as part of a substituent group is optionally substituted with one or more substituents independently selected from halogen, hydroxy, carboxy, cyano, nitro, amino, (lower alkyl)amino, di(lower alkyl)amino, lower alkyl, halogen substituted lower alkyl, lower alkoxy or —$S(O)_{0-2}$-(lower alkyl).

In another embodiment of the present invention, $R^6$ is selected from the group consisting of lower alkyl, lower alkenyl, halogen substituted lower alkyl, cycloalkyl, aryl, aralkyl, heteroaryl and -(lower alkyl)-heteroaryl; wherein the aryl or heteroaryl, whether alone or as part of a substituent group, is optionally substituted with one or more, preferably one to two, substituents independently selected from halogen, hydroxy, carboxy, nitro, amino, (lower alkyl) amino, di(lower alkyl)amino, lower alkyl, lower alkoxy, trifluoromethyl or phenyl.

Preferably, $R^6$ is selected from the group consisting of methyl, ethyl, propyl, isopropyl, butyl, isobutyl, allyl, cyclopentyl, cyclohexyl, phenyl, 2-chlorophenyl, 3-chlorophenyl, 4-chlorophenyl, 4-fluorophenyl, 4-methylphenyl, 4-methoxyphenyl, 4-carboxyphenyl, 4-hydroxyphenyl, 4-nitrophenyl, 4-aminophenyl, 4-dimethylamino-phenyl, 3,4-dichlorophenyl, 2,6-dichloro-phenyl 2-trifluoromethyl-phenyl, 2,2,2-trifluoroethyl, benzyl, 2-thienyl-methyl, 2-furyl-methyl, 2-pyridyl-methyl, 4-biphenyl, 2-pyridyl, 3-pyridyl and 5-chloro-6-benzothienyl.

In an embodiment of the present invention, $R^4$ is selected from the group consisting of hydrogen, halogen, lower alkyl, lower alkenyl, lower alkynyl and cyano; wherein the lower alkyl, the lower alkenyl or the lower alkynyl is optionally substituted on the terminal carbon atom with —Si(lower alkyl)$_3$. In another embodiment of the present invention $R^4$ is selected from the group consisting of hydrogen, halogen, lower alkyl, lower alkenyl, lower alkynyl, cyano and —CC—Si(CH$_3$)$_3$. Preferably, $R^4$ is selected from the group consisting of hydrogen, chloro, iodo, bromo, methyl, ethyl, —CH=CH$_2$, —CCH, cyano and —CC—Si(CH$_3$)$_3$.

In an embodiment of the present invention $R^5$ is selected from the group consisting of halogen, lower alkyl, halogen substituted lower alkyl, lower alkoxy, halogen substituted lower alkoxy, cyano, nitro, amino, (lower alkyl)amino, di(lower alkyl)amino, —C(O)-(lower alkyl), —C(O)-(lower alkoxy), —NH—C(O)-(lower alkyl), —NH—C(O)-(trifluoromethyl) and phenyl; wherein the phenyl is optionally substituted with one or more, preferably, one to two substituents independently selected from halogen, hydroxy, carboxy, lower alkyl, trifluoromethyl, lower alkoxy, trifluoromethoxy, cyano, nitro, amino, lower alkylamino or di(lower alkyl)amino.

In another embodiment of the present invention $R^5$ is selected from the group consisting of halogen, cyano, nitro, amino, lower alkylamino, di(lower alkyl)amino, carboxy, lower-alkyl-carbonyl, lower alkoxy-carbonyl, halogenated lower alkyl, preferably fluorinated lower alkyl, —NHC(O)—CF$_3$, phenyl and phenyl substituted with a halogen. Preferably, $R^5$ is selected from the group consisting of chloro, fluoro, bromo, cyano, nitro, amino, trifluoromethyl, —NHC(O)—CF$_3$, methoxy-carbonyl and chloro-phenyl.

In another embodiment of the present invention, $R^5$ is selected from the group consisting of halogen lower alkyl, lower alkoxy, trifluoromethyl, cyano, nitro, amino, —NH—C(O)—CF$_3$, —C(O)-lower alkoxy and phenyl substituted with halogen. Preferably, $R^5$ is selected from the group consisting of chloro, bromo, fluoro, iodo, methyl, trifluoromethyl, methoxy, cyano, nitro, amino, —NH—C(O)—CF$_3$, methoxy-carbonyl- and 3-chlorophenyl.

In an embodiment of the present invention, $R^7$ is selected from the group consisting of hydrogen, lower alkyl and —Si(lower alkyl)$_3$. In another embodiment of the present invention $R^7$ is selected from the group consisting of hydrogen, lower alkyl and Si(methyl)$_3$. Preferably, $R^7$ is selected from the group consisting of hydrogen, methyl and trimethyl-silyl.

In an embodiment of the present invention $R^2$ is other than methyl and $R^3$ is other than methyl. Preferably, $R^2$ is other than lower alkyl and $R^3$ is other than lower alkyl.

In an embodiment of the present invention X is O. In another embodiment of the present invention X is NR$^1$ and R$^1$ is selected from the group consisting of hydrogen, (lower alkyl)-sulfonyl (preferably, methyl-sulfonyl), phenylsulfonyl, toylysulfonyl (preferably p-tolylsulfonyl), lower alkyl (preferably, methyl or ethyl), —CH$_2$-(fluorinated lower alkyl) (preferably, 2,2,2-trifluoroethyl), cyano-(lower alkyl) (preferably, cyano-methyl), (lower alkyl)-O-(lower alkyl) (preferably, methoxy-methyl) and (lower alkyl)-S-(lower alkyl) (preferably, methyl-thio-methyl).

In another embodiment of the present invention X is O. In another embodiment of the present invention X is NR$^1$ and R$^1$ is selected from the group consisting of hydrogen, (lower alkyl)-sulfonyl (preferably, methyl-sulfonyl), lower alkyl (preferably, methyl or ethyl), —CH$_2$-(fluorinated lower alkyl) (preferably, 2,2,2-trifluoroethyl), cyano-(lower alkyl) (preferably, cyano-methyl), (lower alkyl)-O-(lower alkyl) (preferably, methoxy-methyl) and (lower alkyl)-S-(lower alkyl) (preferably, methyl-thio-methyl).

In an embodiment of the present invention R$^7$ is hydrogen or lower alkyl (preferably methyl). In another embodiment of the present invention b and c are each 0.

In an embodiment of the present invention R$^4$ is selected from the group consisting of hydrogen, halogen (preferably, chloro, bromo or iodo), cyano, lower alkyl (preferably, methyl or ethyl), lower alkenyl (preferably, —CH=CH$_2$), lower alkynyl (preferably, —CCH) and —CC—Si(CH$_3$)$_3$. In another embodiment of the present invention R$^4$ is selected from the group consisting of hydrogen and lower alkyl, preferably, R$^4$ is hydrogen or methyl.

In an embodiment of the present invention a is an integer from 0 to 3, preferably 1 to 3 and R$^5$ is selected from the group consisting of halogen (preferably, chloro, bromo or fluoro), nitro, amino, cyano, (lower alkoxy)-carbonyl (preferably, methoxy-carbonyl), trifluoromethyl, —NHC(O)—CF$_3$ and halogen substituted phenyl (preferably, chlorophenyl).

In an embodiment of the present invention R$^2$ is selected from the group consisting of hydrogen, lower alkyl, trifluoromethyl and —(CH$_2$)—S(O)$_{0-2}$—R$^6$, wherein R$^6$ is selected from lower alkyl (preferably, methyl or ethyl). Preferably, R$^2$ is selected from the group consisting of hydrogen, methyl, ethyl, trifluoromethyl and —CH$_2$—S-ethyl. In another embodiment of the present invention R$^2$ is selected from the group consisting of hydrogen and lower alkyl. Preferably, R$^2$ is selected from the group consisting of hydrogen and methyl. More preferably, R$^2$ is methyl. In another embodiment, R$^2$ is selected from the group consisting of hydrogen and trifluoromethyl.

In an embodiment of the present invention R$^3$ is selected from the group consisting of lower alkyl, halogen substituted lower alkyl, —(CH$_2$)$_{0-2}$—Z—R$^6$; wherein Z is selected from —S—, —SO—, —SO$_2$— and —O—C(O)—; and wherein R$^6$ is selected from the group consisting of lower alkyl, lower akenyl, halogen substituted lower alkyl, cycloalkyl, aryl, aralkyl, heteroaryl and -(lower alkyl)-heteroaryl; wherein the aryl or heteroaryl is optionally substituted with one to two substituents independently selected from halogen, hydroxy, carboxy, nitro, amino, (lower alkyl) amino, di(lower alkyl)amino, lower alkyl, lower alkoxy, trifluoromethyl or phenyl.

In another embodiment of the present invention R$^3$ is selected from the group consisting of lower alkyl (preferably, methyl), halogen substituted lower alkyl (preferably, chloromethyl or trifluoromethyl), —(CH$_2$)$_{0-2}$—S(O)$_{0-2}$—R$^6$ and —(CH$_2$)—OC(O)—R$^6$; wherein R$^6$ is selected from the group consisting of lower alkyl (preferably, methyl, ethyl, propyl, isopropyl or butyl), halogen substituted alkyl (preferably, 2,2,2-trifluoroethyl), lower alkenyl, lower alkynyl, phenyl (optionally substituted with one to two substituents independently selected from halogen, hydroxy, carboxy, trifluoromethyl, nitro, amino, (lower alkyl)amino, di(lower alkyl)amino, lower alkyl, lower alkoxy, phenyl, heteroaryl), aralkyl (preferably, benzyl), cycloalkyl (preferably, cyclopentyl or cyclohexyl) and heteroaryl (preferably, thienyl, furyl or pyridyl) (wherein the heteroaryl is optionally substituted with a substituent selected from lower alkyl).

In an embodiment, $R^3$ is selected from the group consisting of methyl, chloromethyl, trifluoromethyl, —CH$_2$—O-(3-nitrophenyl), —CH$_2$—O-(4-cyanophenyl), —CH$_2$—O-(3-trifluoromethyl-4-cyano-phenyl), —S-methyl, —S-isopropyl, —S-cyclohexyl, S-phenyl, —S-(4-chlorophenyl), —S-(4-fluorophenyl), —S-(3,4-dichlorophenyl), —S-(4-aminophenyl), —SO$_2$-(4-chlorophenyl), —SO$_2$-(3,4-dichlorophenyl), —CH$_2$—S-methyl, —CH$_2$—S-ethyl, —CH$_2$—S-butyl, —CH$_2$—S-propyl, —CH$_2$—S-isopropyl, —CH$_2$—S-isobutyl, —CH$_2$—S-allyl, —CH$_2$—S-phenyl, —CH$_2$—S-(2-chlorophenyl), —CH$_2$—S-(4-chlorophenyl), —CH$_2$—S-(4-fluorophenyl), —CH$_2$—S-(4-methoxyphenyl), —CH$_2$—S-(4-carboxyphenyl), —CH$_2$—S-(4-hydroxyphenyl), —CH$_2$—S-(4-nitrophenyl), —CH$_2$—S-(4-aminophenyl), —CH$_2$—S-(4-dimethylamino-phenyl), —CH$_2$—S-(3,4-dichlorophenyl), —CH$_2$—S-(2,2,2-trifluoroethyl), —CH$_2$—S-benzyl, —CH$_2$—S-cyclopentyl, —CH$_2$—S-cyclohexyl, —CH$_2$—S-(2-thienyl-methyl), —CH$_2$—S-(2-furyl-methyl), —CH$_2$—S-(2-pyridyl-methyl), —CH$_2$—SO-ethyl, —CH$_2$—SO-phenyl, —CH$_2$—SO-(3,4-dichlorophenyl), —CH$_2$—SO-(2,2,2-trifluoroethyl), —CH$_2$—SO-benzyl, —CH$_2$—SO$_2$-methyl, —CH$_2$—SO$_2$-ethyl, —CH$_2$—SO$_2$-propyl, —CH$_2$—SO$_2$-(4-fluorophenyl), —CH$_2$—SO$_2$-(4-hydroxyphenyl), —CH$_2$—SO$_2$-(4-aminophenyl), —CH$_2$—SO$_2$-(4-dimethyl-amino-phenyl), —CH$_2$—SO$_2$-(4-methoxyphenyl), —CH$_2$—SO$_2$-(2,2,2-trifluoroethyl), —CH$_2$—SO$_2$-benzyl, —CH$_2$CH$_2$—S-methyl, —CH$_2$CH$_2$—SO-methyl, —CH$_2$CH$_2$—SO$_2$-methyl, —CH$_2$—O—C(O)-(2-chlorophenyl), —CH$_2$—O—C(O)-(3-chlorophenyl), —CH$_2$—O—C(O)-(4-chlorophenyl), —CH$_2$—O—C(O)-(4-fluorophenyl), —CH$_2$—O—C(O)-(4-nitrophenyl), —CH$_2$—O—C(O)-(4-methyl-phenyl), —CH$_2$—O—C(O)-(4-methoxyphenyl), —CH$_2$—O—C(O)-(2-trifluoro-methyl-phenyl), —CH$_2$—O—C(O)-(4-t-butyl-phenyl), —CH$_2$—O—C(O)-phenyl, —CH$_2$—O—C(O)-(3,4-dichloro-phenyl), —CH$_2$—O—C(O)-(2,6-dichloro-phenyl), —CH$_2$—O—C(O)-(4-dimethyl-amino-phenyl), —CH$_2$—O—C(O)-(4-biphenyl), —CH$_2$—O—C(O)-(2-pyridyl), —CH$_2$—O—C(O)-(3-pyridyl) and —CH$_2$—O—C(O)-(5-chloro-6-benzothienyl).

Preferably, $R^3$ is selected from the group consisting of methyl, chloromethyl, trifluoromethyl, —S-methyl, —S-isopropyl, —S-cyclohexyl, S-phenyl, —S-(4-chlorophenyl), —S-(4-fluorophenyl), —S-(3,4-dichlorophenyl), —S-(4-aminophenyl), —SO$_2$-(4-chlorophenyl), —SO$_2$-(3,4-dichlorophenyl), —CH$_2$—S-methyl, —CH$_2$—S-ethyl, —CH$_2$—S-butyl, —CH$_2$—S-propyl, —CH$_2$—S-isopropyl, —CH$_2$—S-isobutyl, —CH$_2$—S-allyl, —CH$_2$—S-phenyl, —CH$_2$—S-(2-chlorophenyl), —CH$_2$—S-(4-chlorophenyl), —CH$_2$—S-(4-fluorophenyl), —CH$_2$—S-(4-methoxyphenyl), —CH$_2$—S-(4-carboxyphenyl), —CH$_2$—S-(4-hydroxyphenyl), —CH$_2$—S-(4-nitrophenyl), —CH$_2$—S-(4-aminophenyl), —CH$_2$—S-(4-dimethylamino-phenyl), —CH$_2$—S-(3,4-dichlorophenyl), —CH$_2$—S-(2,2,2-trifluoroethyl), —CH$_2$—S-benzyl, —CH$_2$—S-cyclopentyl, —CH$_2$—S-cyclohexyl, —CH$_2$—S-(2-thienyl-methyl), —CH$_2$—S-(2-furyl-methyl), —CH$_2$—S-(2-pyridyl-methyl), —CH$_2$—SO-ethyl, —CH$_2$—SO-phenyl, —CH$_2$—SO-(3,4-dichlorophenyl), —CH$_2$—SO-(2,2,2-trifluoroethyl), —CH$_2$—SO-benzyl, —CH$_2$—SO$_2$-methyl, —CH$_2$—SO$_2$-ethyl, —CH$_2$—SO$_2$-propyl, —CH$_2$—SO$_2$-(4-fluorophenyl), —CH$_2$—SO$_2$-(4-hydroxyphenyl), —CH$_2$—SO$_2$-(4-aminophenyl), —CH$_2$—SO$_2$-(4-dimethylamino-phenyl), —CH$_2$—SO$_2$-(4-methoxyphenyl), —CH$_2$—SO$_2$-(2,2,2-trifluoroethyl), —CH$_2$—SO$_2$-benzyl, —CH$_2$CH$_2$—S-methyl, —CH$_2$CH$_2$—SO-methyl, —CH$_2$CH$_2$—SO$_2$-methyl, —CH$_2$—O—C(O)-(2-chlorophenyl), —CH$_2$—O—C(O)-(3-chlorophenyl), —CH$_2$—O—C(O)-(4-chlorophenyl), —CH$_2$—O—C(O)-(4-fluorophenyl), —CH$_2$—O—C(O)-(4-nitrophenyl), —CH$_2$—O—C(O)-(4-methyl-phenyl), —CH$_2$—O—C(O)-(4-methoxy-phenyl), —CH$_2$—O—C(O)-(2-trifluoro-methyl-phenyl), —CH$_2$—O—C(O)-(4-t-butyl-phenyl), —CH$_2$—O—C(O)-phenyl, —CH$_2$—O—C(O)-(3,4-dichloro-phenyl), —CH$_2$—O—C(O)-(2,6-dichloro-phenyl), —CH$_2$—O—C(O)-(4-dimethyl-amino-phenyl), —CH$_2$—O—C(O)-(4-biphenyl), —CH$_2$—O—C(O)-(2-pyridyl), —CH$_2$—O—C(O)-(3-pyridyl) and —CH$_2$—O—C(O)-(5-chloro-6-benzothienyl).

In an embodiment of the present invention a is 2 and $R^5$ is selected from the group consisting of halogen (preferably, chloro), nitro, cyano and trifluoromethyl. In another embodiment of the present invention b and c are each 0. In another embodiment of the present invention $R^4$ is hydrogen. In another embodiment of the present invention $R^7$ is hydrogen. In another embodiment of the present invention $R^1$ is selected from the group consisting of H and lower alkylsulfonyl (preferably, methyl-sulfonyl).

In an embodiment of the present invention

is a five to six membered, saturated or partially unsaturated ring structure containing one to two heteroatoms selected from O, S or N; wherein the five to six membered, saturated or partially unsaturated ring is optionally substituted with a substituent selected from aralkyl (wherein the aralkyl is optionally substituted with one to two substituents selected independently from the group consisting of halogen, lower alkyl, lower alkoxy, lower alkylsulfonyl and trifluoromethyl), aryl (wherein the aryl is optionally substituted with one to two substituents selected independently from the group consisting of halogen, lower alkyl, lower alkoxy, lower alkylsulfonyl and trifluoromethyl) and aralkyloxycarbonyl.

Preferably,

is selected from the group consisting of tetrahydro-thien-3-yl, (S)-tetrahydro-thien-3-yl, (R)-tetrahydro-thien-3-yl, tetrahydro-thiopyran-4-yl, 4-(1-benzyloxy-carbonyl-piperidinyl), 4-(1-benzyl-piperidinyl), 4-piperidinyl, 4-(1-(4-chlorophenyl)-carbonyl-piperidinyl), 4-(1-(4-trifluoromethyl-benzyl)-piperidinyl), 4-(1-(4-methyl-benzyl)-piperidinyl), 4-(1-(4-fluoro-benzyl)-piperidinyl), 4-(1-(3-methoxy-benzyl)-piperidinyl), 4-(1-(4-chloro-benzyl)-piperidinyl), 4-(1-(4-t-butyl-benzyl)piperidinyl), 4-(1-(4-methylsulfonyl-benzyl)-piperidinyl), 4-(1-(4-methoxy-benzyl)-piperidinyl) and 4-(1-(3,4-dichloro-benzyl)-piperidinyl).

In an embodiment of the present invention

is pyridyl. In another embodiment of the present invention a $R^1$ is hydrogen. In another embodiment of the present invention a is 1 and $R^5$ is selected from cyano or trifluoromethyl. In another embodiment of the present invention b and c are each 0. In another embodiment of the present invention $R^2$ is lower alkyl (preferably, methyl).

In an embodiment of the present invention $R^3$ is selected from the group consisting of halogenated lower alkyl and -(lower alkyl)-$S(O)_{0-2}$—$R^6$. Preferably, $R^3$ is selected from the group consisting of chloromethyl and —$CH_2$—S—$R^6$. Preferably, $R^3$ is selected from the group consisting of chloromethyl, —$CH_2$—S-ethyl, —$CH_2$—S-phenyl, —$CH_2$—S-(4-chlorophenyl), —$CH_2$—S-(4-fluorophenyl) and —$CH_2$—S-cyclohexyl.

In an embodiment of the present invention $R^6$ is selected from the group consisting of lower alkyl, cycloalkyl and aryl (wherein the aryl is optionally substituted with a halogen). Preferably, $R^6$ is selected from the group consisting of ethyl, cyclohexyl, phenyl, 4-chlorophenyl and 4-fluorophenyl.)

In an embodiment of the present invention are compounds of formula (I) wherein $R^1$ is selected from hydrogen or methyl-sulfonyl, $R^4$ is selected from hydrogen, halogen, cyano, —CH=$CH_2$, —CCH or —CC—$Si(CH_3)_3$ (preferably, $R^4$ is selected from hydrogen, halogen or cyano, more preferably, $R^4$ is hydrogen or halogen), $R^7$ is hydrogen, $R^2$ and $R^3$ are each methyl, b is 0, c is 0, a is an integer from 1 to 2, each $R^5$ is independently selected from halogen (preferably, bromo or chloro), cyano, nitro and trifluoromethyl and the $R^5$ groups are bound at the 5 and 6 positions.

Additional embodiments of the present invention, include those wherein the substituents selected for one or more of the variables defined herein (i.e.

, a, b, c, X, Y, $R^2$, $R^3$, $R^4$, $R^5$ and $R^7$) are independently selected to be any individual substituent or any subset of substituents selected from the complete list as defined herein.

In an embodiment of the present invention, the stereo-configuration at the carbon atom bound to $R^2$, $R^3$ and —$(CH_2)_c$—$OR^7$ (i.e. the starred (*) carbon atom in the Tables below) is in the (+) configuration. In another embodiment of the present invention, the stereoconfiguration at the carbon atom bound to $R^2$, $R^3$ and —$(CH_2)_c$—$OR^7$ (i.e. the starred (*) carbon atom in the Tables below) is in the (−) configuration.

Representative compounds of the present invention are as listed in Tables 1, 2, 3, 4 and 5 below. In Tables 2, 3, 4 and 5 the column headed with the "*" symbol denotes the stereo-configuration of the tertiary carbon. The "+" and "−" configurations are based on experimental determination. (The absolute configuration may or may not have been determined.) A notation of "±" indicates a mixture of configurations. A notation of "n/a" indicates that no stereo-center was present. Unless otherwise noted, for compounds listed below wherein $R^2$ contains an —SO— group, said chiral center was present as a mixture of configurations.

TABLE 1

Compounds of Formula (II)

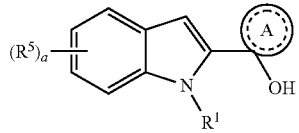

| ID No | $R^1$ | A | $(R^5)_a$ |
|---|---|---|---|
| 14 | H | tetrahydro-thien-3-yl | 5-chloro, 6-$CF_3$ |
| 15 | H | tetrahydro-thien-3-yl | 5-cyano, 6-$CF_3$ |
| 16 | methyl-sulfonyl | tetrahydro-thiopyran-4-yl | 5-nitro, 6-$CF_3$ |
| 17 | H | tetrahydro-thiopyran-4-yl | 5-nitro, 6-$CF_3$ |
| 18 | H | tetrahydro-thien-3-yl | 5-nitro, 6-$CF_3$ |
| 19 | methyl-sulfonyl | 4-(1-benzyloxy-carbonyl-piperidinyl) | 5-chloro, 6-$CF_3$ |
| 20 | H | 4-(1-benzyloxy-carbonyl-piperidinyl) | 5-chloro, 6-$CF_3$ |
| 21 | methyl-sulfonyl | 4-(1-benzyl-piperidinyl) | 5-chloro, 6-$CF_3$ |
| 22 | H | 4-(1-benzyl-piperidinyl) | 5-chloro, 6-$CF_3$ |
| 23 | methyl-sulfonyl | 4-piperidinyl | 5-chloro, 6-$CF_3$ |
| 24 | methyl-sulfonyl | 4-(1-(4-chlorophenyl)-carbonyl-piperidinyl) | 5-chloro, 6-$CF_3$ |
| 25 | H | 4-(1-(4-chlorophenyl)-carbonyl-piperidinyl) | 5-chloro, 6-$CF_3$ |
| 26 | H | 4-(1-(4-trifluoromethyl-benzyl)-piperidinyl) | 5-nitro, 6-$CF_3$ |
| 27 | H | 4-(1-(4-methyl-benzyl)-piperidinyl) | 5-nitro, 6-$CF_3$ |
| 28 | H | 4-(1-(4-fluoro-benzyl)-piperidinyl) | 5-chloro, 6-$CF_3$ |
| 29 | H | 4-(1-(3-methoxy-benzyl)-piperidinyl) | 5-chloro, 6-$CF_3$ |
| 30 | H | 4-(1-(4-methyl-benzyl)-piperidinyl) | 5-chloro, 6-$CF_3$ |
| 31 | H | 4-(1-(4-chloro-benzyl)-piperidinyl) | 5-chloro, 6-$CF_3$ |
| 32 | H | 4-(1-(4-t-butyl-benzyl)-piperidinyl) | 5-chloro, 6-$CF_3$ |
| 33 | H | 4-(1-(4-trifluoromethyl-benzyl)-piperidinyl) | 5-chloro, 6-$CF_3$ |
| 34 | H | 4-(1-(4-methylsulfonyl-benzyl)-piperidinyl) | 5-chloro, 6-$CF_3$ |
| 35 | H | 4-(1-(4-methoxy-benzyl)-piperidinyl) | 5-chloro, 6-$CF_3$ |
| 36 | H | 4-(1-(3,4-dichloro-benzyl)-piperidinyl) | 5-chloro, 6-$CF_3$ |
| 37 | H | 4-(1-(4-fluoro-benzyl)-piperidinyl) | 5-nitro, 6-$CF_3$ |
| 38 | H | 4-(1-(3-methoxy-benzyl)-piperidinyl) | 5-nitro, 6-$CF_3$ |
| 39 | H | 4-(1-(3-methoxy-benzyl)-piperidinyl) | 5-nitro, 6-$CF_3$ |
| 40 | H | 4-(1-(4-chloro-benzyl)-piperidinyl) | 5-nitro, 6-$CF_3$ |
| 41 | H | 4-(1-(4-chloro-benzyl)-piperidinyl) | 5-nitro, 6-$CF_3$ |
| 42 | H | 4-(1-(4-methyl-benzyl)-piperidinyl | 5-nitro, 6-$CF_3$ |
| 43 | H | 4-(1-(3,4-dichloro-benzyl)-piperidinyl) | 5-nitro, 6-$CF_3$ |

TABLE 2

Compounds of Formula (I)

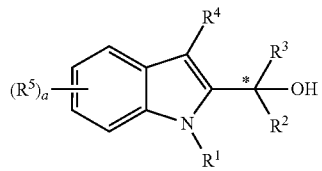

| ID No | * | R¹ | R² | R³ | R⁴ | (R⁵)ₐ |
|---|---|---|---|---|---|---|
| 13 | na | H | —CH₂—S-ethyl | —CH₂—S-ethyl | H | 5-nitro, 6-CF₃ |
| 47 | ± | H | methyl | —CH₂CH₂—S-methyl | H | 5-nitro, 6-CF₃ |
| 48 | ± | methyl-sulfonyl | methyl | —CH₂CH₂—S-methyl | H | 5-nitro, 6-CF₃ |
| 49 | ± | H | methyl | —CH₂CH₂—SO₂-methyl | H | 5-nitro, 6-CF₃ |
| 50 | ± | H | methyl | —CH₂CH₂—SO-methyl | H | 5-nitro, 6-CF₃ |
| 51 | ± | H | methyl | —CH₂CH₂—S-methyl | H | 5-chloro, 6-CF₃ |
| 52 | ± | H | methyl | —CH₂—O—C(O)-(2,6-dichloro-phenyl) | H | 5-nitro, 6-CF₃ |
| 53 | ± | H | methyl | —CH₂—O—C(O)-(4-chloro-phenyl) | H | 5-chloro |
| 54 | ± | H | methyl | —CH₂—O—C(O)-(2-chloro-phenyl) | H | 5-nitro, 6-CF₃ |
| 55 | ± | H | methyl | —CH₂—O—C(O)-(4-chloro-phenyl) | H | 5-nitro, 6-CF₃ |
| 56 | ± | H | methyl | —CH₂—O—C(O)-(3,4-dichloro-phenyl) | H | 5-nitro, 6-CF₃ |
| 57 | ± | H | methyl | —CH₂—O—C(O)-(2-trifluoro-methyl-phenyl) | H | 5-nitro, 6-CF₃ |
| 58 | ± | H | methyl | —CH₂—O—C(O)-(3-chlorophenyl) | H | 5-nitro, 6-CF₃ |
| 59 | ± | H | methyl | —CH₂—O—C(O)-(2-trifluoro-methyl-phenyl) | H | 5-amino, 6-CF₃ |
| 60 | ± | H | methyl | —CH₂—O—C(O)-(2-trifluoro-methyl-phenyl) | H | 5-CF₃—C(O)NH—, 6-CF₃ |
| 61 | ± | H | methyl | —CH₂—O—C(O)-phenyl | H | 5-chloro, 6-CF₃ |
| 62 | ± | H | methyl | —CH₂—O—C(O)-(4-chloro-phenyl) | H | 5-chloro, 6-CF₃ |
| 63 | ± | H | methyl | —CH₂—O—C(O)-(4-nitrophenyl) | H | 5-nitro, 6-CF₃ |
| 64 | ± | H | methyl | —CH₂—O—C(O)-phenyl | H | 5-nitro, 6-CF₃ |
| 65 | ± | H | methyl | —CH₂—O—C(O)-(4-methoxy-phenyl) | H | 5-nitro, 6-CF₃ |
| 66 | ± | H | methyl | —CH₂—O—C(O)-(4-biphenyl) | H | 5-nitro, 6-CF₃ |
| 67 | ± | H | methyl | —CH₂—O—C(O)-(4-dimethyl-amino-phenyl) | H | 5-nitro, 6-CF₃ |
| 68 | ± | H | methyl | —CH₂—O—C(O)-(2-pyridyl) | H | 5-nitro, 6-CF₃ |
| 69 | ± | H | methyl | —CH₂—O—C(O)-(4-methyl-phenyl) | H | 5-nitro, 6-CF₃ |
| 70 | ± | H | methyl | —CH₂—O—C(O)-(5-chloro-6-benzothienyl) | H | 5-nitro, 6-CF₃ |
| 75 | ± | H | methyl | —CH₂—O—C(O)-phenyl | H | 5-cyano, 6-CF₃ |
| 76 | ± | H | methyl | —CH₂—O—C(O)-(4-chloro-phenyl) | H | 5-cyano, 6-CF₃ |
| 77 | ± | H | methyl | —CH₂—O—C(O)-(4-fluorophenyl) | H | 5-cyano, 6-CF₃ |
| 78 | ± | H | methyl | —CH₂—O—C(O)-(3,4-dichloro-phenyl) | H | 5-cyano, 6-CF₃ |
| 79 | ± | H | methyl | —CH₂—O—C(O)-(3-pyridyl) | H | 5-cyano, 6-CF₃ |
| 80 | ± | H | methyl | —CH₂—O—C(O)-(4-t-butyl-phenyl) | H | 5-nitro, 6-CF₃ |
| 81 | ± | methyl-sulfonyl | methyl | —CH₂—S-phenyl | H | 5-methoxy-carbonyl |
| 82 | ± | H | methyl | —CH₂—S-(4-chlorophenyl) | H | 5-chloro, 6-CF₃ |
| 83 | ± | H | methyl | —CH₂—S-(4-fluorophenyl) | H | 5-chloro, 6-CF₃ |
| 84 | ± | H | methyl | —CH₂—S-(2-chlorophenyl) | H | 5-chloro, 6-CF₃ |
| 85 | ± | H | methyl | —CH₂—SO₂-(4-fluorophenyl) | H | 5-chloro, 6-CF₃ |
| 86 | ± | methyl-sulfonyl | methyl | —CH₂—S-(3,4-dichlorophenyl) | H | 5-chloro, 6-CF₃ |
| 87 | ± | H | methyl | —CH₂—S-(3,4-dichlorophenyl) | H | 5-nitro, 6-CF₃ |
| 88 | ± | methyl-sulfonyl | methyl | —CH₂—S-(4-chlorophenyl) | H | a = 0 |
| 89 | ± | H | methyl | —CH₂—S-(4-chlorophenyl) | H | a = 0 |
| 90 | ± | methyl-sulfonyl | methyl | —CH₂—S-phenyl | H | a = 0 |
| 91 | ± | methyl-sulfonyl | methyl | —CH₂—S-(3,4-dichlorophenyl) | H | 5-nitro, 6-CF₃ |
| 92 | ± | H | methyl | —CH₂—S-cyclohexyl | H | 5-cyano, 6-CF₃ |
| 93 | ± | methyl-sulfonyl | methyl | —CH₂—S-cyclohexyl | H | 5-methoxy-carbonyl |
| 94 | ± | H | methyl | —CH₂—S-cyclohexyl | H | 5-methoxy-carbonyl |
| 95 | ± | H | methyl | —CH₂—S-phenyl | H | 5-cyano, 6-CF₃ |
| 96 | ± | H | methyl | —CH₂—S-(4-chlorophenyl) | H | 5-cyano, 6-CF₃ |
| 97 | ± | H | methyl | —CH₂—S-(4-chlorophenyl) | H | 5-methoxy-carbonyl |
| 98 | ± | methyl-sulfonyl | methyl | —CH₂—S-(4-fluorophenyl) | H | 5-methoxy-carbonyl |
| 99 | ± | methyl-sulfonyl | methyl | —CH₂—S-(4-fluorophenyl) | H | 5-chloro |
| 100 | ± | H | methyl | —CH₂—S-(4-fluorophenyl) | H | 5-chloro |
| 101 | ± | methyl-sulfonyl | methyl | —CH₂—S-(4-chlorophenyl) | H | 5-chloro |
| 102 | ± | H | methyl | —CH₂—S-(4-chlorophenyl) | H | 5-chloro |
| 103 | ± | H | methyl | —CH₂—S-(4-nitrophenyl) | H | 5-nitro, 6-CF₃ |
| 104 | ± | H | methyl | —CH₂—S-(4-aminophenyl) | H | 5-chloro, 6-CF₃ |
| 105 | ± | H | methyl | —CH₂—S-(3,4-dichlorophenyl) | H | 5-chloro, 6-CF₃ |
| 106 | ± | H | methyl | —CH₂—S-phenyl | H | 5-chloro, 6-CF₃ |
| 107 | ± | methyl-sulfonyl | methyl | —CH₂—S-(4-fluorophenyl) | H | a = 0 |
| 108 | ± | H | methyl | —CH₂—S-(4-fluorophenyl) | H | a = 0 |
| 109 | ± | H | methyl | —CH₂—S-(4-fluorophenyl) | H | 5-cyano, 6-CF₃ |
| 110 | ± | H | methyl | —CH₂—SO₂-(4-fluorophenyl) | H | 5-cyano, 6-CF₃ |
| 112 | ± | H | methyl | —CH₂—SO-phenyl | H | 5-chloro, 6-CF₃ |
| 113 | (b) | H | methyl | —CH₂—SO-(4-fluorophenyl) | H | 5-chloro, 6-CF₃ |
| 114 | (b) | H | methyl | —CH₂—SO-(4-fluorophenyl) | H | 5-chloro, 6-CF₃ |
| 115 | ± | H | methyl | —CH₂—SO-phenyl | H | 5-chloro, 6-CF₃ |
| 116 | (b) | H | methyl | —CH₂—SO-(3,4-dichlorophenyl) | H | 5-chloro, 6-CF₃ |
| 117 | (b) | H | methyl | —CH₂—SO-(3,4-dichlorophenyl) | H | 5-chloro, 6-CF₃ |

TABLE 2-continued

Compounds of Formula (I)

$$\text{(R}^5\text{)}_a\text{—indole with R}^4\text{ at 3-position, R}^1\text{ on N, and at 2-position: —C*(R}^3\text{)(R}^2\text{)—OH}$$

| ID No | * | R¹ | R² | R³ | R⁴ | (R⁵)ₐ |
|---|---|---|---|---|---|---|
| 118 | ± | H | methyl | -CH₂—SO₂-(4-aminophenyl) | H | 5-chloro, 6-CF₃ |
| 119 | ± | methyl-sulfonyl | methyl | —CH₂—S-(4-hydroxyphenyl) | H | 5-chloro, 6-CF₃ |
| 120 | ± | H | methyl | —CH₂—S-(4-hydroxyphenyl) | H | 5-chloro, 6-CF₃ |
| 121 | ± | H | methyl | —CH₂—SO₂-(4-hydroxyphenyl) | H | 5-chloro, 6-CF₃ |
| 122 | ± | H | methyl | —CH₂—S-(4-nitrophenyl) | H | 5-chloro, 6-CF₃ |
| 123 | ± | H | methyl | —CH₂—S-(2-aminophenyl) | H | 5-chloro, 6-CF₃ |
| 124 | ± | H | methyl | —CH₂—S-(4-dimethylamino-phenyl) | H | 5-chloro, 6-CF₃ |
| 125 | ± | methyl-sulfonyl | methyl | —CH₂—S-(4-aminophenyl) | H | 5-chloro, 6-CF₃ |
| 126 | ± | H | methyl | —CH₂—SO₂-(4-dimethylamino-phenyl) | H | 5-chloro, 6-CF₃ |
| 127 | ± | H | methyl | —CH₂—S-(2-dimethylamino-phenyl) | H | 5-chloro, 6-CF₃ |
| 128 | ± | methyl-sulfonyl | methyl | —CH₂—SO₂-(4-methoxyphenyl) | H | 5-chloro, 6-CF₃ |
| 129 | ± | H | methyl | —CH₂—SO₂-(4-methoxyphenyl) | H | 5-chloro, 6-CF₃ |
| 130 | ± | methyl-sulfonyl | methyl | —CH₂—S-(4-methoxyphenyl) | H | 5-chloro, 6-CF₃ |
| 131 | ± | H | methyl | —CH₂—S-(4-methoxyphenyl) | H | 5-chloro, 6-CF₃ |
| 132 | ± | methyl-sulfonyl | methyl | —CH₂—S-(4-carboxyphenyl) | H | 5-chloro, 6-CF₃ |
| 133 | ± | H | methyl | —CH₂—S-(4-carboxyphenyl) | H | 5-chloro, 6-CF₃ |
| 134 | ± | methyl-sulfonyl | methyl | —CH₂—S-methyl | H | 5-chloro, 6-CF₃ |
| 135 | ± | H | methyl | —CH₂—S-methyl | H | 5-chloro, 6-CF₃ |
| 136 | ± | H | methyl | —CH₂—S-methyl | H | 5-cyano, 6-CF₃ |
| 137 | ± | methyl-sulfonyl | methyl | —CH₂—SO₂-methyl | H | 5-chloro, 6-CF₃ |
| 138 | ± | H | methyl | —CH₂—SO₂-methyl | H | 5-chloro, 6-CF₃ |
| 139 | ± | H | methyl | —CH₂—S-methyl | H | 5-nitro, 6-CF₃ |
| 140 | ± | H | methyl | —CH₂—SO₂-methyl | H | 5-nitro, 6-CF₃ |
| 141 | ± | methyl-sulfonyl | methyl | —CH₂—S-ethyl | H | 5-nitro, 6-CF₃ |
| 142 | ± | H | methyl | —CH₂—S-ethyl | H | 5-nitro, 6-CF₃ |
| 143 | ± | H | methyl | —CH₂—SO₂-ethyl | H | 5-nitro, 6-CF₃ |
| 144 | + | H | methyl | —CH₂—S-methyl | H | 5-nitro, 6-CF₃ |
| 145 | − | H | methyl | —CH₂—S-methyl | H | 5-nitro, 6-CF₃ |
| 146 | ± | methyl-sulfonyl | methyl | —CH₂—S-ethyl | H | 5-chloro, 6-CF₃ |
| 147 | + | H | methyl | —CH₂—SO₂-methyl | H | 5-nitro, 6-CF₃ |
| 148 | − | H | methyl | —CH₂—SO₂-methyl | H | 5-nitro, 6-CF₃ |
| 149 | + | H | methyl | —CH₂—S-ethyl | H | 5-nitro, 6-CF₃ |
| 150 | − | H | methyl | —CH₂—S-ethyl | H | 5-nitro, 6-CF₃ |
| 151 | − (a) | H | methyl | —CH₂—SO₂-ethyl | H | 5-nitro, 6-CF₃ |
| 152 | ± | H | methyl | —CH₂—S-ethyl | H | 5-chloro, 6-CF₃ |
| 153 | ± | H | methyl | —CH₂—S-ethyl | H | 5-nitro, 6-CF₃ |
| 154 | ± | methyl-sulfonyl | methyl | —CH₂—S-ethyl | H | 5-chloro |
| 155 | − (a) | H | methyl | —CH₂—SO-ethyl | H | 5-nitro, 6-CF₃ |
| 156 | + (a) | H | methyl | —CH₂—SO₂-ethyl | H | 5-nitro, 6-CF₃ |
| 157 | ± | methyl-sulfonyl | H | —CH₂—S-ethyl | H | 5-nitro, 6-CF₃ |
| 158 | ± | H | H | —CH₂—S-ethyl | H | 5-nitro, 6-CF₃ |
| 159 | ± | H | methyl | —CH₂—S-ethyl | H | 5-fluoro, 6-CF₃ |
| 160 | ± | H | methyl | —CH₂—S-benzyl | H | 5-nitro, 6-CF₃ |
| 161 | ± | H | methyl | —CH₂—SO-benzyl | H | 5-nitro, 6-CF₃ |
| 162 | ± | H | methyl | —CH₂—SO₂-benzyl | H | 5-nitro, 6-CF₃ |
| 163 | ± | H | methyl | —CH₂—S-isopropyl | H | 5-nitro, 6-CF₃ |
| 164 | ± | H | methyl | —CH₂—S-isopropyl | H | 5-nitro, 6-CF₃ |
| 165 | ± | methyl | methyl | —CH₂—S-ethyl | H | 5-nitro, 6-CF₃ |
| 166 | ± | H | methyl | —CH₂—S-ethyl | H | 5-amino, 6-CF₃ |
| 168 | ± | H | methyl | —CH₂—S-n-propyl | H | 5-nitro, 6-CF₃ |
| 169 | ± | H | ethyl | —CH₂—S-ethyl | H | 5-nitro, 6-CF₃ |
| 170 | ± | H | methyl | —CH₂—S-isobutyl | H | 5-nitro, 6-CF₃ |
| 171 | ± | H | methyl | —CH₂—S-(2,2,2-trifluoroethyl) | H | 5-nitro, 6-CF₃ |
| 172 | ± | methyl-sulfonyl | methyl | —CH₂—S-(2,2,2-trifluoroethyl) | H | 5-nitro, 6-CF₃ |
| 173 | ± | H | methyl | —CH₂—S-cyclopentyl | H | 5-nitro, 6-CF₃ |
| 174 | ± | methyl-sulfonyl | methyl | —CH₂—S-cyclopentyl | H | 5-nitro, 6-CF₃ |
| 175 | ± | H | methyl | -CH₂—SO₂-ethyl | H | 5-nitro, 6-CF₃ |
| 176 | ± | H | ethyl | —CH₂—SO₂-ethyl | H | 5-nitro, 6-CF₃ |
| 177 | ± | H | methyl | —CH₂—SO₂-n-propyl | H | 5-nitro, 6-CF₃ |
| 178 | ± | H | methyl | -CH₂—S-ethyl | H | a = 0 |
| 180 | ± | H | H | —CH₂—SO-ethyl | H | 5-nitro, 6-CF₃ |
| 181 | ± | H | ethyl | —CH₂—S-ethyl | H | 5-chloro, 6-CF₃ |
| 182 | ± | methyl-sulfonyl | ethyl | —CH₂—S-(2,2,2-trifluoroethyl) | H | 5-nitro, 6-CF₃ |
| 183 | ± | methyl-sulfonyl | methyl | —CH₂—S-(2-thienyl-methyl) | H | 5-nitro, 6-CF₃ |
| 184 | ± | methyl-sulfonyl | methyl | —CH₂—S-allyl | H | 5-nitro, 6-CF₃ |
| 185 | ± | H | ethyl | —CH₂—S-(2,2,2-trifluoroethyl) | H | 5-nitro, 6-CF₃ |
| 186 | ± | methyl-sulfonyl | ethyl | —CH₂—S-(2,2,2-trifluoroethyl) | H | 5-chloro, 6-CF₃ |

TABLE 2-continued

Compounds of Formula (I)

| ID No | * | R¹ | R² | R³ | R⁴ | (R⁵)ₐ |
|---|---|---|---|---|---|---|
| 187 | ± | methyl-sulfonyl | methyl | —CH₂—S-(2,2,2-trifluoroethyl) | H | 5-chloro, 6-CF₃ |
| 188 | ± | methyl-sulfonyl | methyl | —CH₂—S-(2,2,2-trifluoroethyl) | H | 5-fluoro, 6-CF₃ |
| 189 | ± | H | methyl | —CH₂—S-(2,2,2-trifluoroethyl) | H | 5-fluoro, 6-CF₃ |
| 190 | ± | H | methyl | —CH₂—S-(2,2,2-trifluoroethyl) | H | 5-chloro, 6-CF₃ |
| 191 | ± | H | ethyl | —CH₂—SO₂-(2,2,2-trifluoroethyl) | H | 5-nitro, 6-CF₃ |
| 192 | ± | H | ethyl | —CH₂—S-(2,2,2-trifluoroethyl) | H | 5-chloro, 6-CF₃ |
| 193 | ± | methyl-sulfonyl | ethyl | —CH₂—S-(2,2,2-trifluoroethyl) | H | 5-fluoro, 6-CF₃ |
| 194 | ± | H | ethyl | —CH₂—S-(2,2,2-trifluoroethyl) | H | 5-fluoro, 6-CF₃ |
| 195 | ± | methyl-sulfonyl | methyl | —CH₂—S-n-butyl | H | 5-nitro, 6-CF₃ |
| 196 | ± | H | methyl | —CH₂—S-propyl | H | 5-chloro, 6-CF₃ |
| 197 | ± | H | methyl | —CH₂—S-(2-thienyl-methyl) | H | 5-nitro, 6-CF₃ |
| 198 | ± | H | methyl | —CH₂—S-(2-furyl-methyl) | H | 5-nitro, 6-CF₃ |
| 199 | ± | H | ethyl | —CH₂—SO₂-(2,2,2-trifluoroethyl) | chloro | 5-nitro, 6-CF₃ |
| 200 | ± | H | methyl | —CH₂—S-n-butyl | H | 5-nitro, 6-CF₃ |
| 201 | + | H | methyl | —CH₂—S-(2,2,2-trifluoroethyl) | H | 5-nitro, 6-CF₃ |
| 202 | − | H | methyl | —CH₂—S-(2,2,2-trifluoroethyl) | H | 5-nitro, 6-CF₃ |
| 203 | ± | methyl-sulfonyl | methyl | —CH₂—S-ethyl | H | 5-fluoro, 6-chloro |
| 204 | ± | H | methyl | —CH₂—S-(2-pyridyl-methyl) | H | 5-nitro, 6-CF₃ |
| 205 | ± | H | methyl | —CH₂—SO-(2,2,2-trifluoroethyl) | H | 5-nitro, 6-CF₃ |
| 206 | ± | H | methyl | —CH₂—S-ethyl | H | 5-fluoro, 6-chloro |
| 207 | ± | H | methyl | —CH₂—SO₂-(2,2,2-trifluoroethyl) | chloro | 5-CF₃, 6-nitro |
| 208 | ± | H | methyl | —CH₂—SO₂-(2,2,2-trifluoroethyl) | H | 5-nitro, 6-CF₃ |
| 209 | ± | H | methyl | —CH₂—S-ethyl | H | 5-cyano, 6-CF₃ |
| 210 | ± | H | methyl | —CH₂—S-(4-aminophenyl) | H | 5-chloro, 6-CF₃ |
| 211 | ± | H | methyl | —CH₂—S-(2,2,2-trifluoroethyl) | H | 5-cyano, 6-CF₃ |
| 212 | ± | H | methyl | —CH₂—S-ethyl | H | 5-nitro, 7-CF₃ |
| 213 | ± | H | methyl | —CH₂—S-(2,2,2-trifluoroethyl) | iodo | 5-nitro, 6-CF₃ |
| 214 | ± | methyl-sulfonyl | methyl | —CH₂—S-ethyl | H | 6-CF₃ |
| 215 | ± | methyl-sulfonyl | methyl | —CH₂—S-ethyl | H | 5-cyano, 6-CF₃ |
| 216 | ± | methyl-sulfonyl | ethyl | —CH₂—S-ethyl | H | 5-nitro, 6-CF₃ |
| 217 | − | H | methyl | —CH₂—S-ethyl | H | 5-cyano, 6-CF₃ |
| 218 | + | H | methyl | —CH₂—S-ethyl | H | 5-cyano, 6-CF₃ |
| 219 | ± | H | methyl | —CH₂—S-ethyl | methyl | 5-cyano, 6-CF₃ |
| 220 | ± | H | methyl | —CH₂—S-ethyl | methyl | 5-bromo, 6-CF₃ |
| 221 | ± | H | methyl | —CH₂—S-ethyl | methyl | 5-nitro, 6-CF₃ |
| 222 | − | H | methyl | —CH₂—SO₂-ethyl | H | 5-cyano, 6-CF₃ |
| 223 | ± | H | ethyl | —CH₂—S-ethyl | H | 5-cyano, 6-CF₃ |
| 224 | ± | H | methyl | —CH₂—S-ethyl | H | 5-cyano, 6-chloro |
| 225 | − | H | methyl | —CH₂—S-ethyl | H | 5-cyano, 6-chloro |
| 226 | ± | methyl | methyl | —CH₂—S-ethyl | H | 5-cyano, 6-chloro |
| 227 | ± | H | methyl | —CH₂—S-ethyl | H | 5,6-dichloro |
| 228 | + | H | methyl | —CH₂—S-ethyl | H | 5-chloro, 6-cyano |
| 229 | ± | methyl-sulfonyl | methyl | —CH₂—S-benzyl | H | 5-nitro, 6-CF₃ |
| 230 | ± | H | methyl | —CH₂—SO-ethyl | H | 5-CF₃, 6-nitro |
| 231 | − (a) | methyl | methyl | —CH₂—S-ethyl | H | 5-nitro, 6-CF₃ |
| 232 | − (a) | methyl | methyl | —CH₂—SO₂-ethyl | H | 5-nitro, 6-CF₃ |
| 233 | − | H | methyl | —CH₂—S-ethyl | methyl | 5-cyano, 6-CF₃ |
| 234 | + | H | methyl | —CH₂—S-ethyl | methyl | 5-cyano, 6-CF₃ |
| 236 | ± | methyl | methyl | —CH₂—S-ethyl | H | 5-cyano, 6-CF₃ |
| 237 | ± | 2,2,2-trifluoro-ethyl | methyl | —CH₂—S-ethyl | H | 5-cyano, 6-CF₃ |
| 238 | ± | methyl-sulfonyl | methyl | —CH₂—S-(2-furyl-methyl) | H | 5-nitro, 6-CF₃ |
| 239 | ± | methyl-sulfonyl | methyl | —CH₂—S-propyl | H | 5-chloro, 6-CF₃ |
| 240 | ± | methyl | methyl | —CH₂—SO₂-ethyl | H | 5-cyano, 6-CF₃ |
| 241 | + (a) | H | methyl | —CH₂—S-ethyl | iodo | 5-nitro, 6-CF₃ |
| 242 | + (a) | H | methyl | —CH₂—S-ethyl | cyano | 5-nitro, 6-CF₃ |
| 243 | ± | ethyl | methyl | —CH₂—S-ethyl | H | 5-cyano, 6-CF₃ |
| 244 | − (a) | H | methyl | —CH₂—S-ethyl | iodo | 5-nitro, 6-CF₃ |
| 245 | ± | H | methyl | —CH₂—SO-ethyl | methyl | 5-cyano, 6-CF₃ |
| 246 | ± | H | methyl | —CH₂—SO₂-ethyl | methyl | 5-cyano, 6-CF₃ |
| 247 | − | H | methyl | —CH₂—S-ethyl | cyano | 5-nitro, 6-CF₃ |
| 248 | − (a) | H | methyl | —CH₂—SO-ethyl | H | 5-cyano, 6-CF₃ |
| 250 | − (a) | methyl | methyl | —CH₂—SO₂-ethyl | H | 5-nitro, 6-CF₃ |
| 251 | − | H | methyl | —CH₂—SO₂-ethyl | methyl | 5-cyano, 6-CF₃ |
| 252 | − (a) | H | methyl | —CH₂—SO-ethyl | methyl | 5-cyano, 6-CF₃ |
| 254 | ± | H | methyl | —S-(3,4-dichlorophenyl) | H | 5-nitro, 6-CF₃ |
| 255 | ± | H | methy | —SO₂-(3,4-dichlorophenyl) | H | 5-nitro, 6-CF₃ |
| 256 | ± | H | methyl | —S-cyclohexyl | H | 5-nitro, 6-CF₃ |

TABLE 2-continued

Compounds of Formula (I)

| ID No | * | R¹ | R² | R³ | R⁴ | (R⁵)ₐ |
|---|---|---|---|---|---|---|
| 257 | ± | H | methyl | —S-cyclohexyl | H | 5-cyano, 6-CF₃ |
| 258 | ± | H | methyl | —S-phenyl | H | 5-nitro, 6-CF₃ |
| 259 | ± | H | methyl | —S-(4-chlorophenyl) | H | 5-nitro, 6-CF₃ |
| 260 | ± | H | methyl | —S-(4-fluorophenyl) | H | 5-nitro, 6-CF₃ |
| 261 | ± | H | methyl | —S-(4-chlorophenyl) | H | 5-cyano, 6-CF₃ |
| 262 | ± | H | methyl | —SO₂-(4-chlorophenyl) | H | 5-cyano, 6-CF₃ |
| 265 | ± | H | methyl | —S-(4-aminophenyl) | H | 5-chloro, 6-CF₃ |
| 266 | ± | H | methyl | —S-(4-aminophenyl) | H | 5-nitro, 6-CF₃ |
| 267 | ± | H | methyl | —S-methyl | H | 5-nitro, 6-CF₃ |
| 273 | na | methyl-sulfonyl | methyl | methyl | H | 5-nitro, 6-CF₃ |
| 274 | na | H | methyl | methyl | H | 5-nitro, 6-CF₃ |
| 275 | na | H | methyl | methyl | chloro | 5-nitro, 6-CF₃ |
| 276 | na | H | methyl | methyl | iodo | 5-nitro, 6-CF₃ |
| 277 | na | H | methyl | methyl | bromo | 5-nitro, 6-CF₃ |
| 278 | na | H | methyl | methyl | iodo | 5-cyano, 6-CF₃ |
| 279 | na | H | methyl | methyl | iodo | 5-chloro, 6-CF₃ |
| 280 | na | H | methyl | methyl | bromo | 5-chloro, 6-CF₃ |
| 281 | na | H | methyl | methyl | —CH=CH₂ | 5-nitro, 6-CF₃ |
| 282 | na | H | methyl | methyl | chloro | 5-chloro, 6-CF₃ |
| 283 | na | methyl-sulfonyl | methyl | methyl | H | 5-cyano, 6-CF₃ |
| 284 | na | methyl-sulfonyl | methyl | methyl | H | 5-chloro, 6-CF₃ |
| 285 | na | H | methyl | methyl | H | 5-chloro, 6-CF₃ |
| 286 | na | H | methyl | methyl | H | 5-cyano, 6-CF₃ |
| 287 | na | H | methyl | methyl | chloro | 5-cyano, 6-CF₃ |
| 288 | na | H | methyl | methyl | bromo | 5-cyano, 6-CF₃ |
| 289 | na | H | methyl | methyl | methyl | 5-cyano, 6-CF₃ |
| 290 | na | H | methyl | methyl | methyl | 5-nitro, 6-CF₃ |
| 291 | na | H | methyl | methyl | cyano | 5-nitro, 6-CF₃ |
| 292 | na | methyl-sulfonyl | methyl | methyl | H | 5-bromo, 6-CF₃ |
| 293 | na | methyl-sulfonyl | methyl | methyl | H | 5-bromo |
| 294 | na | H | methyl | methyl | H | 5-bromo |
| 295 | na | H | methyl | methyl | cyano | 5-cyano, 6-CF₃ |
| 316 | ± | methyl-sulfonyl | methyl | —CH₂—S-ethyl | H | 5-bromo |
| 317 | − (a) | methyl | methyl | —CH₂—S-ethyl | methyl | 5-cyano, 6-CF₃ |
| 318 | − (a) | methyl | methyl | —CH₂—S-ethyl | methyl | 5-cyano, 6-CF₃ |
| 319 | ± | H | methyl | —CH₂—SO-ethyl | methyl | 5-cyano, 6-CF₃ |
| 320 | ± | methyl-sulfonyl | methyl | —CH₂—S-ethyl | H | 5-(3-chloro-phenyl) |
| 321 | ± | H | methyl | —CH₂—S-ethyl | H | 5-(3-chloro-phenyl) |
| 322 | ± | methoxy-methyl | methyl | —CH₂—S-ethyl | H | 5-cyano, 6-CF₃ |
| 323 | ± | cyano-methyl | methyl | —CH₂—S-ethyl | H | 5-cyano, 6-CF₃ |
| 324 | ± | H | methyl | —CH₂—S-ethyl | iodo | 5-cyano, 6-CF₃ |
| 325 | ± | H | methyl | —CH₂—S-ethyl | —CC—Si(CH₃)₃ | 5-cyano, 6-CF₃ |
| 326 | ± | H | methyl | —CH₂—S-ethyl | —CCH | 5-cyano, 6-CF₃ |
| 327 | ± | H | trifluoro-methyl | —CH₂—S-ethyl | H | 5-cyano, 6-CF₃ |
| 328 | ± | methoxy-methyl | H | trifluoromethyl | H | 5-cyano, 6-CF₃ |
| 329 | ± | H | methyl | trifluoromethyl | H | 5-cyano, 6-CF₃ |
| 330 | ± | H | methyl | trifluoromethyl | iodo | 5-cyano, 6-CF₃ |
| 331 | ± | cyano-methyl | methyl | trifluoromethyl | H | 5-cyano, 6-CF₃ |
| 332 | ± | methoxy-methyl | methyl | trifluoromethyl | H | 5-cyano, 6-CF₃ |
| 333 | ± | methyl-thio-methyl | methyl | trifluoromethyl | H | 5-cyano, 6-CF₃ |
| 334 | + | H | methyl | trifluoromethyl | H | 5-cyano, 6-CF₃ |
| 335 | − | H | methyl | trifluoromethyl | H | 5-cyano, 6-CF₃ |
| 344 | ± | H | methyl | —CH₂—S-ethyl | ethyl | 5-cyano, 6-CF₃ |
| 345 | − (a) | H | methyl | trifluoromethyl | chloro | 5-cyano, 6-CF₃ |
| 346 | − (a) | H | methyl | trifluoromethyl | iodo | 5-cyano, 6-CF₃ |
| 347 | − (a) | H | methyl | trifluoromethyl | —CC—Si(CH₃)₃ | 5-cyano, 6-CF₃ |
| 348 | − (a) | H | methyl | trifluoromethyl | —CCH | 5-cyano, 6-CF₃ |
| 349 | − (a) | H | methyl | —CH₂—S-ethyl | iodo | 5-cyano, 6-CF₃ |
| 350 | − (a) | H | methyl | —CH₂—S-ethyl | —CC—Si(CH₃)₃ | 5-cyano, 6-CF₃ |
| 351 | − (a) | H | methyl | —CH₂—S-ethyl | —CCH | 5-cyano, 6-CF₃ |
| 352 | − (a) | H | methyl | —CH₂—S-ethyl | ethyl | 5-cyano, 6-CF₃ |
| 353 | ± | H | methyl | —CH₂—S-ethyl | H | 5-chloro |
| 354 | − (a) | H | methyl | —CH₂—SO₂-ethyl | ethyl | 5-cyano, 6-CF₃ |
| 355 | na | H | methyl | methyl | —CCH | 5-cyano, 6-CF₃ |
| 356 | na | H | methyl | methyl | —CC—Si(CH₃)₃ | 5-cyano, 6-CF₃ |
| 357 | na | H | trifluoro-methyl | trifluoromethyl | H | 5-cyano, 6-CF₃ |
| 358 | na | methyl-sulfonyl | trifluoro-methyl | trifluoromethyl | H | 5-cyano, 6-CF₃ |

TABLE 2-continued

Compounds of Formula (I)

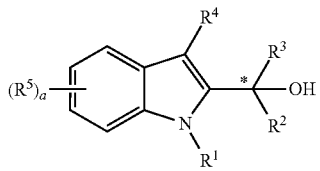

| ID No | * | R¹ | R² | R³ | R⁴ | (R⁵)$_a$ |
|---|---|---|---|---|---|---|
| 394 | ± | H | H | —CH$_2$Cl | H | 5-cyano, 6-CF$_3$ |
| 397 | +[a] | H | methyl | —CH$_2$—SO$_2$-ethyl | H | 5-cyano, 6-CF$_3$ |
| 398 | +[a] | H | methyl | —CH$_2$—S-ethyl | iodo | 5-cyano, 6-CF$_3$ |
| 401 | +[a] | H | methyl | —CH$_2$—S-ethyl | bromo | 5-cyano, 6-CF$_3$ |
| 402 | ± | methyl-sulfonyl | methyl | —CH$_2$—S-ethyl | H | 5-cyano |
| 403 | ± | H | methyl | —CH$_2$—S-ethyl | H | 5-cyano |
| 404 | ± | H | methyl | —CH$_2$—SO$_2$-ethyl | H | 5-chloro, 6-CF$_3$ |
| 405 | na | H | methyl | methyl | H | 5,6-dichloro |
| 406 | ± | H | methyl | —CH$_2$—S-ethyl | chloro | 5-chloro |
| 407 | ± | H | methyl | —CH$_2$—SO$_2$-ethyl | H | 5-cyano, 6-CF$_3$ |
| 408 | ± | H | H | —CH$_2$—S-methyl | H | 5-cyano, 6-CF$_3$ |
| 409 | na | H | methyl | methyl | —CH=CH$_2$ | 5-chloro, 6-CF$_3$ |
| 410 | ± | H | H | —CH$_2$—S-ethyl | H | 5-cyano, 6-CF$_3$ |
| 411 | ± | H | H | —CH$_2$—S-ethyl | iodo | 5-cyano, 6-CF$_3$ |
| 412 | ± | H | H | —CH$_2$—SO$_2$-ethyl | H | 5-cyano, 6-CF$_3$ |
| 413 | ± | H | H | —CH$_2$—S-ethyl | bromo | 5-cyano, 6-CF$_3$ |
| 414 | ± | H | methyl | —CH$_2$—S-ethyl | H | 5-methyl, 6-CF$_3$ |
| 415 | ± | H | methyl | —CH$_2$—S-ethyl | H | 5-cyano, 6-methyl, 7-iodo |
| 426 | ± | H | methyl | —CH$_2$—O-(4-cyano-phenyl) | H | 5-cyano, 6-CF$_3$ |
| 428 | ± | H | methyl | —CH$_2$—O-(3-nitro-phenyl) | H | 5-cyano, 6-CF$_3$ |
| 429 | ± | H | methyl | —CH$_2$—O-(3-CF$_3$-4-cyano-phenyl) | H | 5-cyano, 6-CF$_3$ |
| 436 | ± | H | methyl | trifluoromethyl | H | 5-cyano, 6-CF$_3$ |
| 445 | ± | H | methyl | —CH$_2$—S-ethyl | H | 5-cyano, 6-methoxy |
| 446 | ± | H | methyl | —CH$_2$—S-ethyl | H | 5-cyano, 6-methyl |

(a) The stereo-configuration for these compounds was not experimentally determined. However, the compounds were made from stereospecific precursors. More specifically, compounds #151, 155, 195, 231, 232, 242, 247 and 250 were prepared from compound #150; compounds #156 and 241 were prepared from compound #149; compounds #248, 249, 349, 350, 351, 353 and 354 were prepared from compound #217; compound #252, 397, 398 and 401 were prepared from compound #233; compound #345, 346, 347 and 348 were prepared from compound #355. The listed stereo-configuration os therefore based on the stereo-configuration of the precursor.

(b) Compounds #113, 114, 116 and 117 were prepared with a single configuration at the S of the SO group, although relative and absolute configurations were not determined.

TABLE 3

Compounds of Formula (I)

| ID No | * | R¹ | R² | R³ | R⁴ | (R⁵)$_a$ |
|---|---|---|---|---|---|---|
| 253 | ± | H | methyl | —S-(4-chlorophenyl) | H | 5-chloro, 6-CF$_3$ |
| 268 | ± | H | methyl | —S-isopropyl | H | 5-nitro, 6-CF$_3$ |

TABLE 4

Compounds of Formula (I)

| ID No | * | R⁶ | (R⁵)$_a$ |
|---|---|---|---|
| 8 | ± | 4-chlorophenyl | 5-nitro, 6-CF$_3$ |
| 9 | ± | ethyl | 5-nitro, 6-CF$_3$ |

TABLE 5

Compounds of Formula (III)

| ID No | * | R⁶ | (R⁵)$_a$ |
|---|---|---|---|
| 1 | ± | cyclohexyl | 5-CF$_3$ |
| 2 | ± | phenyl | 5-CF$_3$ |
| 3 | ± | 4-chlorophenyl | 5-CF$_3$ |
| 5 | ± | 4-fluorophenyl | 5-CF$_3$ |
| 6 | ± | ethyl | 5-cyano |

Additional representative compounds of the present invention are as listed in Table 6 below.

TABLE 6

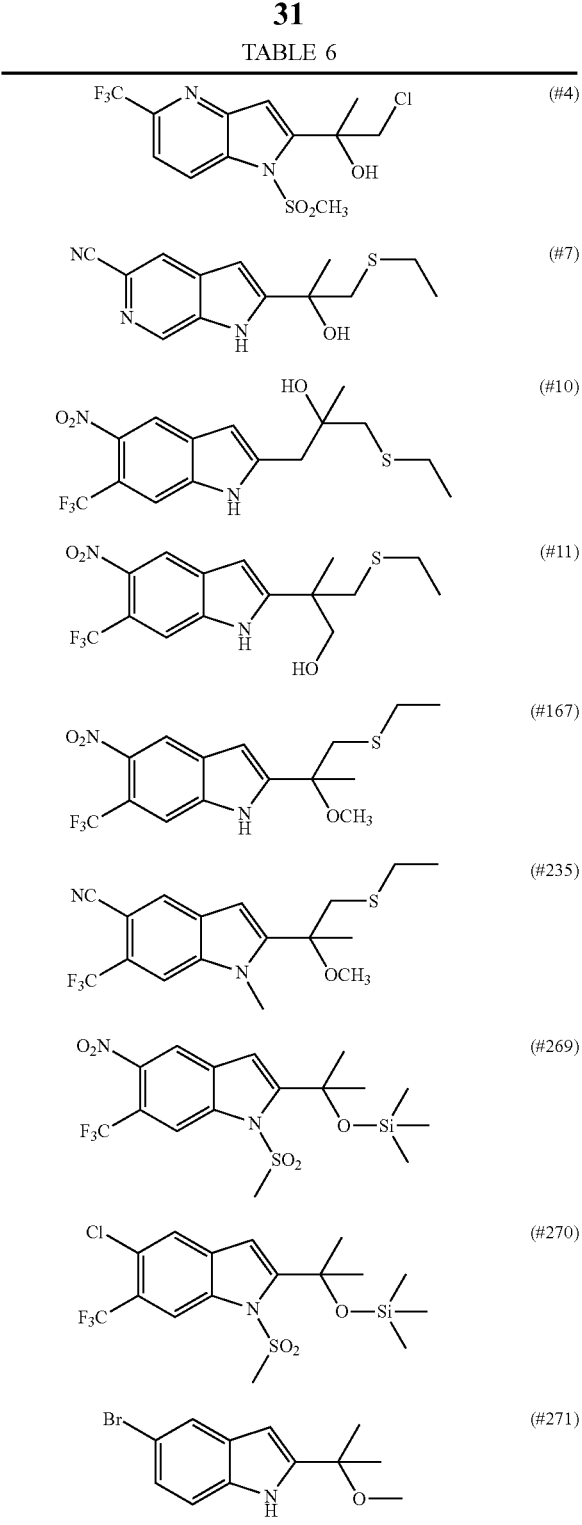

As used herein, unless otherwise noted, the term "halogen" shall mean chlorine, bromine, fluorine and iodine.

As used herein, unless otherwise noted, the term "alkyl", whether used alone or as part of a substituent group, includes straight and branched chains. For example, alkyl radicals include methyl, ethyl, propyl, isopropyl, butyl, isobutyl, sec-butyl, t-butyl, pentyl and the like. Unless otherwise noted, "lower" when used with alkyl means a carbon chain composition of 1-4 carbon atoms.

As used herein, unless otherwise noted, the term "halogen substituted lower alkyl" shall mean a lower alkyl group as defined above wherein one or more of the hydrogen atoms is replaced with a halogen atom. Suitable examples include, but are not limited to, trifluoromethyl, 2,2,2-trifluoro-eth-1-yl, chloromethyl, fluoromethyl and the like. Similarly, the term "fluorinated lower alkyl" shall mean a lower alkyl group as defined above wherein one or more of the hydrogen atoms is replaced with a fluorine atom. Suitable examples include, but are not limited to, fluoromethyl, fluoroethyl, trifluoromethyl, 2,2,2-trifluoro-eth-1-yl, and the like.

As used herein, unless otherwise noted, "alkoxy" shall denote an oxygen ether radical of the above described straight or branched chain alkyl groups. For example, methoxy, ethoxy, n-propoxy, sec-butoxy, t-butoxy, n-hexyloxy and the like.

As used herein, unless otherwise noted, the term "cycloalkyl" shall mean any stable four to eight membered monocyclic, saturated ring system, for example cyclobutyl, cyclopentyl, cyclohexyl, cycloheptyl and cyclooctyl.

As used herein, unless otherwise noted, "aryl" shall refer to unsubstituted carbocylic aromatic groups such as phenyl, naphthyl, and the like.

As used herein, unless otherwise noted, "heteroaryl" shall denote any five or six membered, monocyclic aromatic ring structure containing at least one heteroatom selected from the group consisting of O, N and S, optionally containing one to three additional heteroatoms independently selected from the group consisting of O, N and S; or a nine or ten membered, bicyclic aromatic ring structure containing at least one heteroatom selected from the group consisting of O, N and S, optionally containing one to four additional heteroatoms independently selected from the group consisting of O, N and S. The heteroaryl group may be attached at any heteroatom or carbon atom of the ring such that the result is a stable structure.

Examples of suitable heteroaryl groups include, but are not limited to, pyrrolyl, furyl, thienyl, oxazolyl, imidazolyl, purazolyl, isoxazolyl, isothiazolyl, triazolyl, thiadiazolyl, pyridyl, pyridazinyl, pyrimidinyl, pyrazinyl, pyranyl, furazanyl, indolizinyl, indolyl, isoindolinyl, indazolyl, benzofuryl, benzothienyl, benzimidazolyl, benzthiazolyl, purinyl, quinolizinyl, quinolinyl, isoquinolinyl, isothiazolyl, cinnolinyl, phthalazinyl, quinazolinyl, quinoxalinyl, naphthyridinyl, pteridinyl, and the like.

As used herein, the notation "*" shall denote the presence of a stereogenic center.

When a particular group is "substituted" (e.g., cycloalkyl, aryl, heteroaryl, etc), that group may have one or more substituents, preferably from one to five substituents, more preferably from one to three substituents, most preferably from one to two substituents, independently selected from the list of substituents.

With reference to substituents, the term "independently" means that when more than one of such substituents is possible, such substituents may be the same or different from each other.

Under standard nomenclature used throughout this disclosure, the terminal portion of the designated side chain is described first, followed by the adjacent functionality toward the point of attachment. Thus, for example, a "phenyl-($C_1$-$C_6$alkyl)-aminocarbonyl-($C_1$-$C_6$alkyl)" substituent refers to a group of the formula

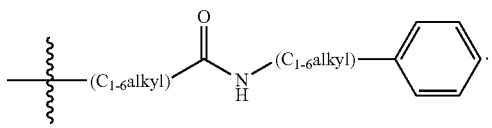

Under the standard nomenclature used throughout this disclosure, substituents on the core will be designated such that the X (or Y) atom is numbered 1 and the remaining ring atoms are numbered sequentially in a counterclockwise direction. For example, for compounds of formula (I), the substituents on the core shall be designated as bound at the following positions of attachment:

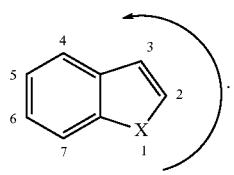

Abbreviations used in the specification, particularly the Schemes and Examples, are as follows:
AR=Androgen Receptor
BPH=Benign Prostatic Hyperplasia
Bu$_4$NHSO$_4$ or =Tetrabutyl ammonium hydrogen sulfate TBAHS
DABCO=1,4-Diazabicyclo[2.2.2]octane
DCM=Dichloromethane
DIPEA or DIEA or =Diisopropylethylamine iPr$_2$NEt
DHT=Dihydrotestosterone
DMAC=N,N-Dimethylacetamide
DMAP=4-N,N-Dimethylaminopyridine
DMEM/F12=Dulbecco's modified Eagle's medium/F12
DMF=N,N-Dimethylformamide
DMSO=Dimethylsulfoxide
DTT=Dithiothreitol
EDTA=Ethylene diamine tetraacetic acid
Et$_2$O=Diethyl ether
EtOAc=Ethyl acetate
EtOH=Ethanol
HPLC=High Pressure Liquid Chromatography
KOAc=Potassium Acetate
mCPBA=m-Chloro-peroxybenzoic acid
MeOH=Methanol
NBS=N-bromosuccinimide
NCS=N-chlorosuccinimide
NIS=N-iodosuccinimide
NMP=1-Methyl2-pyrrolidinone
NMR=Nuclear Magnetic Resonance
PdCl$_2$(PPh$_3$)$_2$=Bis(triphenylphosphine) Palladium (II) chloride
Pd$_2$(dba)$_3$=Tris[μ-[(1,2-η:4,5-η)-(1E,4E)-1,5-diphenyl-1,4-pentadien-3-one]]dipalladium
PdCl$_2$(dppf)=1,1'-Bis(diphenylphosphino)ferrocenepalladium chloride
Pd(OAc)$_2$=Palladium (II) acetate
Ph$_3$P=Triphenyl Phosphine
OTBS=t-Butyl-dimethyl silyloxy
OXONE®=Potassium monopersulfate triple salt
PBS=Phosphate-buffered saline
TBAF=Tetrabutylammonium fluoride
TE or TED Buffer=Tris HCl+EDTA (Tetraacetic Acid Ethylene Diamine)
TEA or Et$_3$N=Triethylamine
THF=Tetrahydrofuran
TMS=Trimethylsilyl
Tris HCl=Tris[hydroxymethyl]aminomethyl hydrochloride The term "subject" as used herein, refers to an animal, preferably a mammal, most preferably a human, who has been the object of treatment, observation or experiment.

The term "therapeutically effective amount" as used herein, means that amount of active compound or pharmaceutical agent that elicits the biological or medicinal response in a tissue system, animal or human that is being sought by a researcher, veterinarian, medical doctor or other clinician, which includes, but is not limited to, alleviation of the symptoms of the disease or disorder being treated.

As used herein, the term "composition" is intended to encompass a product comprising the specified ingredients in the specified amounts, as well as any product which results, directly or indirectly, from combinations of the specified ingredients in the specified amounts.

Where the compounds according to this invention have at least one chiral center, they may accordingly exist as enantiomers. Where the compounds possess two or more chiral centers, they may additionally exist as diastereomers. It is to be understood that all such isomers and mixtures thereof are encompassed within the scope of the present invention. Furthermore, some of the crystalline forms for the compounds may exist as polymorphs and as such are intended to be included in the present invention. In addition, some of the compounds may form solvates with water (i.e., hydrates) or common organic solvents, and such solvates are also intended to be encompassed within the scope of this invention.

Where the processes for the preparation of the compounds according to the invention give rise to mixture of stereoisomers, these isomers may be separated by conventional techniques such as preparative chromatography. The compounds may be prepared in racemic form, or individual enantiomers may be prepared either by enantiospecific synthesis or by resolution. The compounds may, for example, be resolved into their component enantiomers by standard techniques, such as the formation of diastereomeric pairs by salt formation with an optically active acid, such as (−)-di-p-toluoyl-D-tartaric acid and/or (+)-di-p-toluoyl-L-tartaric acid followed by fractional crystallization and regeneration of the free base. The compounds may also be resolved by formation of diastereomeric esters or amides, followed by chromatographic separation and removal of the chiral auxiliary. Alternatively, the compounds may be resolved using a chiral HPLC column.

During any of the processes for preparation of the compounds of the present invention, it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 1991. The protecting groups may be removed at a convenient subsequent stage using methods known from the art.

The present invention includes within its scope prodrugs of the compounds of this invention. In general, such prodrugs will be functional derivatives of the compounds which are readily convertible in vivo into the required compound.

Thus, in the methods of treatment of the present invention, the term "administering" shall encompass the treatment of the various disorders described with the compound specifically disclosed or with a compound which may not be specifically disclosed, but which converts to the specified compound in vivo after administration to the patient. Conventional procedures for the selection and preparation of suitable prodrug derivatives are described, for example, in *Design of Prodrugs*, ed. H. Bundgaard, Elsevier, 1985.

For use in medicine, the salts of the compounds of this invention refer to "pharmaceutically acceptable salts." Other salts may, however, be useful in the preparation of compounds according to this invention or of their pharmaceutically acceptable salts. Suitable pharmaceutically acceptable salts of the compounds include acid addition salts which may, for example, be formed by mixing a solution of the compound with a solution of a pharmaceutically acceptable acid such as hydrochloric acid, sulfuric acid, fumaric acid, maleic acid, succinic acid, acetic acid, benzoic acid, citric acid, tartaric acid, carbonic acid or phosphoric acid. Furthermore, where the compounds of the invention carry an acidic moiety, suitable pharmaceutically acceptable salts thereof may include alkali metal salts, e.g., sodium or potassium salts; alkaline earth metal salts, e.g., calcium or magnesium salts; and salts formed with suitable organic ligands, e.g., quaternary ammonium salts. Representative pharmaceutically acceptable salts include the following:

acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, pamoate (embonate), palmitate, pantothenate, phosphate/diphosphate, polygalacturonate, salicylate, stearate, sulfate, subacetate, succinate, tannate, tartrate, teoclate, tosylate, triethiodide and valerate.

Representative acids and bases which may be used in the preparation of pharmaceutically acceptable salts include the following:

acids including acetic acid, 2,2-dichlorolactic acid, acylated amino acids, adipic acid, alginic acid, ascorbic acid, L-aspartic acid, benzenesulfonic acid, benzoic acid, 4-acetamidobenzoic acid, (+)-camphoric acid, camphorsulfonic acid, (+)-(1S)-camphor-10-sulfonic acid, capric acid, caproic acid, caprylic acid, cinnamic acid, citric acid, cyclamic acid, dodecylsulfuric acid, ethane-1,2-disulfonic acid, ethanesulfonic acid, 2-hydrocy-ethanesulfonic acid, formic acid, fumaric acid, galactaric acid, gentisic acid, glucoheptonic acid, D-gluconic acid, D-glucoronic acid, L-glutamic acid, α-oxo-glutaric acid, glycolic acid, hipuric acid, hydrobromic acid, hydrochloric acid, (+)-L-lactic acid, (±)-DL-lactic acid, lactobionic acid, maleic acid, (−)-L-malic acid, malonic acid, (±)-DL-mandelic acid, methanesulfonic acid, naphthalene-2-sulfonic acid, naphthalene-1,5-disulfonic acid, 1-hydroxy-2-naphthoic acid, nicotinc acid, nitric acid, oleic acid, orotic acid, oxalic acid, palmitric acid, pamoic acid, phosphoric acid, L-pyroglutamic acid, salicylic acid, 4-amino-salicylic acid, sebaic acid, stearic acid, succinic acid, sulfuric acid, tannic acid, (+)-L-tartaric acid, thiocyanic acid, p-toluenesulfonic acid and undecylenic acid; and bases including ammonia, L-arginine, benethamine, benzathine, calcium hydroxide, choline, deanol, diethanolamine, diethylamine, 2-(diethylamino)-ethanol, ethanolamine, ethylenediamine, N-methyl-glucamine, hydrabamine, 1H-imidazole, L-lysine, magnesium hydroxide, 4-(2-hydroxyethyl)-morpholine, piperazine, potassium hydroxide, 1-(2-hydroxyethyl)-pyrrolidine, secondary amine, sodium hydroxide, triethanolamine, tromethamine and zinc hydroxide.

The present invention further comprises pharmaceutical compositions containing one or more compounds of formula (I), compounds of formula (II) and/or compounds of formula (III) with a pharmaceutically acceptable carrier. Pharmaceutical compositions containing one or more of the compounds of the invention described herein as the active ingredient can be prepared by intimately mixing the compound or compounds with a pharmaceutical carrier according to conventional pharmaceutical compounding techniques. The carrier may take a wide variety of forms depending upon the desired route of administration (e.g., oral, parenteral). Thus for liquid oral preparations such as suspensions, elixirs and solutions, suitable carriers and additives include water, glycols, oils, alcohols, flavoring agents, preservatives, stabilizers, coloring agents and the like; for solid oral preparations, such as powders, capsules and tablets, suitable carriers and additives include starches, sugars, diluents, granulating agents, lubricants, binders, disintegrating agents and the like. Solid oral preparations may also be coated with substances such as sugars or be enteric-coated so as to modulate major site of absorption. For parenteral administration, the carrier will usually consist of sterile water and other ingredients may be added to increase solubility or preservation. Injectable suspensions or solutions may also be prepared utilizing aqueous carriers along with appropriate additives.

To prepare the pharmaceutical compositions of this invention, one or more compounds of the present invention as the active ingredient is intimately admixed with a pharmaceutical carrier according to conventional pharmaceutical compounding techniques, which carrier may take a wide variety of forms depending of the form of preparation desired for administration, e.g., oral or parenteral such as intramuscular. In preparing the compositions in oral dosage form, any of the usual pharmaceutical media may be employed. Thus, for liquid oral preparations, such as for example, suspensions, elixirs and solutions, suitable carriers and additives include water, glycols, oils, alcohols, flavoring agents, preservatives, coloring agents and the like; for solid oral preparations such as, for example, powders, capsules, caplets, gelcaps and tablets, suitable carriers and additives include starches, sugars, diluents, granulating agents, lubricants, binders, disintegrating agents and the like. Because of their ease in administration, tablets and capsules represent the most advantageous oral dosage unit form, in which case solid pharmaceutical carriers are obviously employed. If desired, tablets may be sugar coated or enteric coated by standard techniques. For parenterals, the carrier will usually comprise sterile water, through other ingredients, for example, for purposes such as aiding solubility or for preservation, may be included. Injectable suspensions may also be prepared, in which case appropriate liquid carriers, suspending agents and the like may be employed. The pharmaceutical compositions herein will contain, per dosage unit, e.g., tablet, capsule, powder, injection, teaspoonful and the like, an amount of the active ingredient necessary to deliver an effective dose as described above. The pharmaceutical compositions herein will contain, per unit dosage unit, e.g., tablet, capsule, powder, injection, suppository, teaspoonful and the like, of from about 0.01-500 mg and may be given at a dosage of from about 0.05-500 mg/kg/day, preferably from about 0.05-10 mg/kg/day, more preferably from about 1.0-3.0 mg/kg/day. The dosages, however, may be varied depending upon the requirement of the patients, the severity of the condition being treated and the compound being employed. The use of either daily administration or post-periodic dosing may be employed.

Preferably these compositions are in unit dosage forms from such as tablets, pills, capsules, powders, granules, sterile parenteral solutions or suspensions, metered aerosol or liquid sprays, drops, ampoules, autoinjector devices or suppositories; for oral parenteral, intranasal, sublingual or rectal administration, or for administration by inhalation or insufflation. Alternatively, the composition may be presented in a form suitable for once-weekly or once-monthly administration; for example, an insoluble salt of the active compound, such as the decanoate salt, may be adapted to provide a depot preparation for intramuscular injection. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective dosage forms such as tablets, pills and capsules. This solid preformulation composition is then subdivided into unit dosage forms of the type described above containing from 0.1 to about 500 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of material can be used for such enteric layers or coatings, such materials including a number of polymeric acids with such materials as shellac, cetyl alcohol and cellulose acetate.

The liquid forms in which the novel compositions of the present invention may be incorporated for administration orally or by injection include, aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions, include synthetic and natural gums such as tragacanth, acacia, alginate, dextran, sodium carboxymethylcellulose, methylcellulose, polyvinyl-pyrrolidone or gelatin.

The method of treating disorders or conditions modulated by the androgen receptor described in the present invention may also be carried out using a pharmaceutical composition comprising any of the compounds as defined herein and a pharmaceutically acceptable carrier. The pharmaceutical composition may contain between about 0.01 mg and 500 mg, preferably about 10 to 100 mg, of the compound, and may be constituted into any form suitable for the mode of administration selected. Carriers include necessary and inert pharmaceutical excipients, including, but not limited to, binders, suspending agents, lubricants, flavorants, sweeteners, preservatives, dyes, and coatings. Compositions suitable for oral administration include solid forms, such as pills, tablets, caplets, capsules (each including immediate release, timed release and sustained release formulations), granules, and powders, and liquid forms, such as solutions, syrups, elixers, emulsions, and suspensions. Forms useful for parenteral administration include sterile solutions, emulsions and suspensions.

Advantageously, compounds of the present invention may be administered in a single daily dose, or the total daily dosage may be administered in divided doses of two, three or four times daily. Furthermore, compounds for the present invention can be administered in intranasal form via topical use of suitable intranasal vehicles, or via transdermal skin patches well known to those of ordinary skill in that art. To be administered in the form of a transdermal delivery system, the dosage administration will, of course, be continuous rather than intermittent throughout the dosage regimen.

For instance, for oral administration in the form of a tablet or capsule, the active drug component can be combined with an oral, non-toxic pharmaceutically acceptable inert carrier such as ethanol, glycerol, water and the like. Moreover, when desired or necessary, suitable binders; lubricants, disintegrating agents and coloring agents can also be incorporated into the mixture. Suitable binders include, without limitation, starch, gelatin, natural sugars such as glucose or beta-lactose, corn sweeteners, natural and synthetic gums such as acacia, tragacanth or sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

The liquid forms in suitably flavored suspending or dispersing agents such as the synthetic and natural gums, for example, tragacanth, acacia, methyl-cellulose and the like. For parenteral administration, sterile suspensions and solutions are desired. Isotonic preparations which generally contain suitable preservatives are employed when intravenous administration is desired.

The compound of the present invention can also be administered in the form of liposome delivery systems, such as small unilamellar vesicles, large unilamellar vesicles, and multilamellar vesicles. Liposomes can be formed from a variety of phospholipids, such as cholesterol, stearylamine or phophatidylcholines.

Compounds of the present invention may also be delivered by the use of monoclonal antibodies as individual carriers to which the compound molecules are coupled. The compounds of the present invention may also be coupled with soluble polymers as targetable drug carriers. Such polymers can include polyvinylpyrrolidone, pyran copolymer, polyhydroxypropylmethacrylamidephenol, polyhydroxy-ethylaspartamidephenol, or polyethyl eneoxide-polylysine substituted with palmitoyl residue. Furthermore, the compounds of the present invention may be coupled to a class of biodegradable polymers useful in achieving controlled release of a drug, for example, polylactic acid, polyepsilon caprolactone, polyhydroxy butyeric acid, polyorthoesters, polyacetals, polydihydropyrans, polycyanoacrylates and cross-linked or amphipathic block copolymers of hydrogels.

Compounds of this invention may be administered in any of the foregoing compositions and according to dosage regimens established in the art whenever treatment of disorders or conditions modulated by the androgen receptor is required.

The daily dosage of the products may be varied over a wide range from 0.01 to 500 mg per adult human per day. For oral administration, the compositions are preferably provided in the form of tablets containing, 0.01, 0.05, 0.1, 0.5, 1.0, 2.5, 5.0, 10.0, 15.0, 25.0, 50.0, 100, 150, 200, 250 and 500 milligrams of the active ingredient for the symptomatic adjustment of the dosage to the patient to be treated. An effective amount of the drug is ordinarily supplied at a dosage level of from about 0.01 mg/kg to about 500 mg/kg of body weight per day. Preferably, the range is from about 0.5 to about 10.0 mg/kg of body weight per day, most preferably, from about 1.0 to about 3.0 mg/kg of body weight per day. The compounds may be administered on a regimen of 1 to 4 times per day.

Optimal dosages to be administered may be readily determined by those skilled in the art, and will vary with the particular compound used, the mode of administration, the strength of the preparation, the mode of administration, and the advancement of the disease condition. In addition, factors associated with the particular patient being treated, including patient age, weight, diet and time of administration, will result in the need to adjust dosages.

Compounds of formula (I), (II) and (III) may be prepared according to the processes outlined in the Schemes below.

Compounds of formula (I) wherein b is 0, c is 0 and X is $NR^1$, may be prepared according to the process outlined in Scheme 1 below.

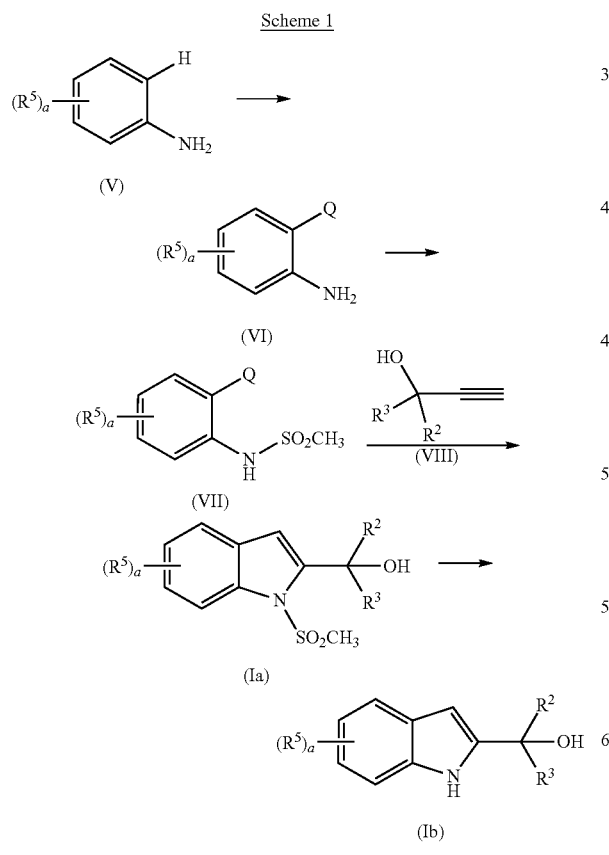

Accordingly, a suitably substituted compound of formula (V), a known compound or compound prepared by known methods, is reacted with a source of iodine or bromine, such as NIS, ICl, NBS, $Br_2$, $I_2$ and the like, in an organic solvent or mixture thereof, such as THF, methanol, acetic acid, THF/methanol, and the like, optionally in the presence of a catalyst, such as acetic acid (with ICl), toluene sulfonic acid (with NIS or NBS), and the like, to yield the corresponding compound of formula (VI), wherein Q is I or Br, respectively.

The compound of formula (VI) is reacted with mesyl chloride (or alternatively, with p-toluenesulfonyl chloride), in the presence of an organic base such as pyridine, potassium t-butoxide, and the like, in an organic solvent such as THF, pyridine, DMF, and the like, to yield the corresponding compound of formula (VII).

The compound of formula (VII) is reacted with a suitably substituted compound of formula (VIII), a known compound or compound prepared by known methods, in the presence of a catalyst such as $PdCl_2(PPh_3)_2$, $Pd_2(dba)_3$, $PdCl_2(dppf)$, and the like, in the presence of CuI, in the presence of an organic base, preferably, in the presence of a tertiary amine base such as TEA, DIPEA, pyridine, and the like, in an organic solvent such as THF, DMF, DMAC, and the like, to yield the corresponding compound of formula (Ia).

The compound of formula (Ia) is optionally de-protected according to known methods, for example, by reacting with a base such as NaOH, KOH, NaO(lower alkyl), and the like, in an organic solvent or mixture thereof such as methanol/water, ethanol/water, THF, and the like, to yield the corresponding compound of formula (Ib). Alternatively, the compound of formula (Ia) is reacted with TBAF in an organic solvent such as THF, DMF, and the like, preferably at an elevated temperature of greater than or equal to about 50° C., to yield the corresponding compound of formula (Ib).

Compounds of formula (II) wherein b is 0, c is 0 and X is $NR^1$ and compounds of formula (III) wherein b is 0 and c is 0, may be similarly prepared according to the process outlined in Scheme 1 above.

More particularly, compounds of formula (II) wherein b is 0, c is 0 and X is $NR^1$ may be prepared by substituting a suitably substituted compound of formula (IX)

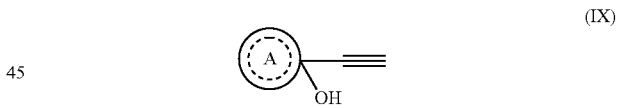

a known compound or compound prepared by known methods, for the compound of formula (VIII), to yield the corresponding compound of formula (IIa)

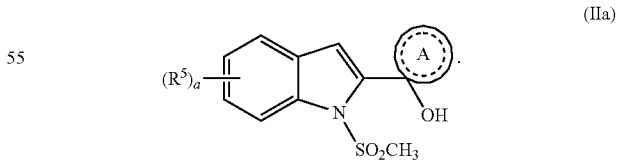

The compound of formula (IIa) may be further optionally de-protected according to known methods to yield the corresponding compound of formula (IIb) wherein $R^1$ is hydrogen.

Similarly, compounds of formula (III) may be prepared according to the process outlined in Scheme 1 by substituting a suitably substituted compound of formula (X)

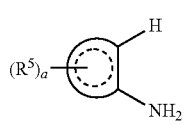

(X)

a known compound or compound prepared by known methods, for the compound of formula (V), to yield the corresponding compound of formula (IIIa)

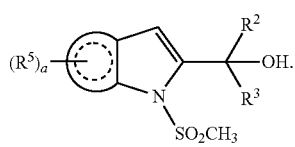

(IIIa)

The compound of formula (IIIa) may be further optionally de-protected according to known methods to yield the corresponding compound of formula (IIIb) wherein $R^1$ is hydrogen.

Compounds of formula (I), compounds of formula (II) and compounds of formula (III) wherein b is 1 and/or c is 1 can be prepared according to the process outlined in Scheme 1 by substituting a suitably substituted compound of formula (XI), (XII) or (XIII)

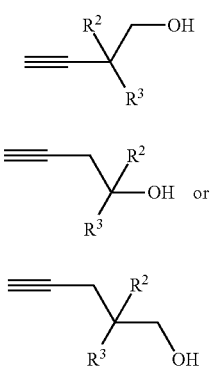

(XI)

(XII)

(XIII)

a known compound or compound prepared by known methods, for the compound of formula (VIII).

Compounds of formula (I) wherein $R^4$ is lower alkyl, more preferably methyl, may be prepared according to the process outlined in Scheme 2.

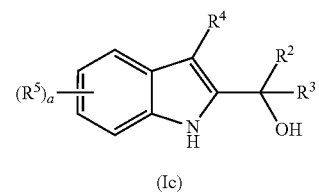

(Ic)

Accordingly, a suitably substituted compound of formula (VI) is reacted with a suitably substituted compound of formula (XIV), a known compound or compound prepared by known methods, in the presence of a catalyst such as palladium acetate, in the presence of a base such as potassium acetate, DABCO, and the like, at an elevated temperature, preferably, at an elevated temperature of greater than or equal to about 70° C., more preferably, at an elevated temperature of about 80° C., to yield the corresponding compound of formula (Ic).

Compounds of formula (II) and compounds of formula (III) wherein $R^4$ is lower alkyl, preferably methyl, may be similarly prepared according to the process outlined in Scheme 2. More specifically, compounds of formula (II) may be prepared by substituting a suitably substituted compound of formula (XV)

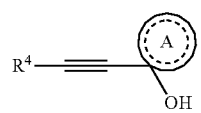

(XV)

for the compound of formula (XIV). Similarly, compounds of formula (III) may be prepared by substituting a suitably substituted compound of formula (XVI)

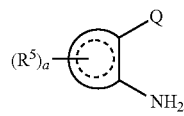

(XVI)

for the compound of formula (VI).

Compounds of formula (I) wherein $R^4$ is other than hydrogen or methyl, may be prepared according to the processes outlined in Schemes 3 and 4 below.

Compounds of formula (I) wherein $R^4$ is cyano may be prepared according to the process outlined in Scheme 3 below.

Scheme 2

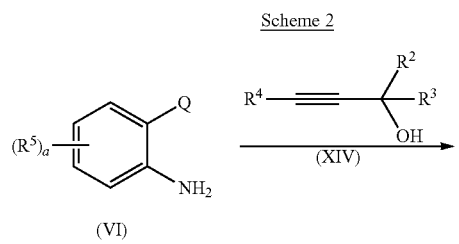

(VI)   (XIV)

Scheme 3

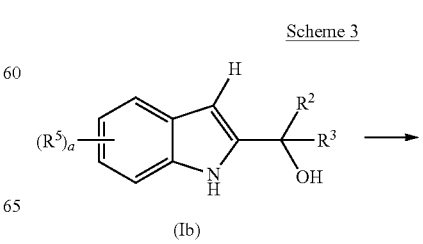

(Ib)

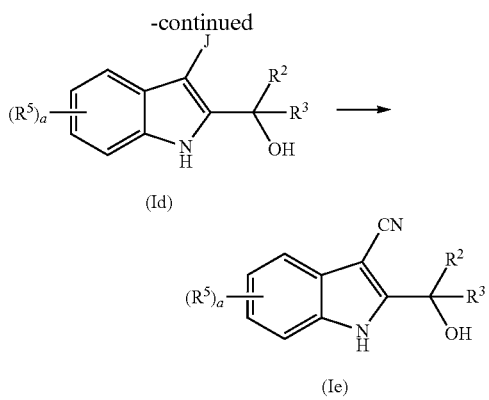

Accordingly, a suitably substituted compound of formula (Ib) is reacted with a source of iodine, bromine or chlorine such as NIS, NBS, NCS, and the like, in the presence of a base such as potassium t-butoxide, NaH, and the like, in an organic solvent such as THF, DMAC, NMP, and the like, to yield the corresponding compound of formula (Id), wherein J is I, Br or Cl, respectively.

The compound of formula (Id) wherein J is Br or I is reacted with CuCN, in an organic solvent such as DMF, DMAC, NMP, and the like, to yield the corresponding compound of formula (Ie).

Compounds of formula (I) wherein $R^4$ is lower alkyl other than methyl, lower alkenyl or lower alkynyl may be prepared according to the process outlined in Scheme 4.

erably a tertiary amine base such as TEA, DIPEA, pyridine, and the like, to yield the corresponding compound of formula (XVIII).

The compound of formula (XVIII) is reacted with a reagent such as TBAF, $K_2CO_3$, NaO(lower alkyl), and the like, in an organic solvent such as THF, MeOH, EtOH, and the like, to yield the corresponding compound of formula (If).

One skilled in the art will recognize that the compound of formula (If) may be further optionally reduced with a suitable reducing agent such as $H_2$ gas in the presence of a catalyst such as Pd on carbon, Pt on carbon, Lindlar's catalyst, and the like, in an organic solvent such as ethyl acetate, methanol, ethanol, and the like, to yield the corresponding compound of formula (I) wherein the alkynyl group is converted to the corresponding alkenyl (i.e. by selecting the reducing conditions to partially reduce the triple bond) or alkyl (i.e. by selecting the reducing conditions to fully reduce the triple bond).

Alternatively, the compound of formula (Id) is reacted with a suitably substituted compound of formula (XIX), a known compound or compound prepared by known methods, in the presence of a catalyst such as $Pd(PPh_3)_4$, and the like, in the presence of an inorganic salt such as lithium chloride, and the like, to yield the corresponding compound of formula (Ig) (For example, see *Tetrahedron*, 58(51) 2002 pp. 10181-10188). The compound of formula (Ig) may then be further, optionally reduced, as described above, to yield the corresponding compound wherein the lower alkenyl is converted to the corresponding lower alkyl (other than methyl).

Scheme 4

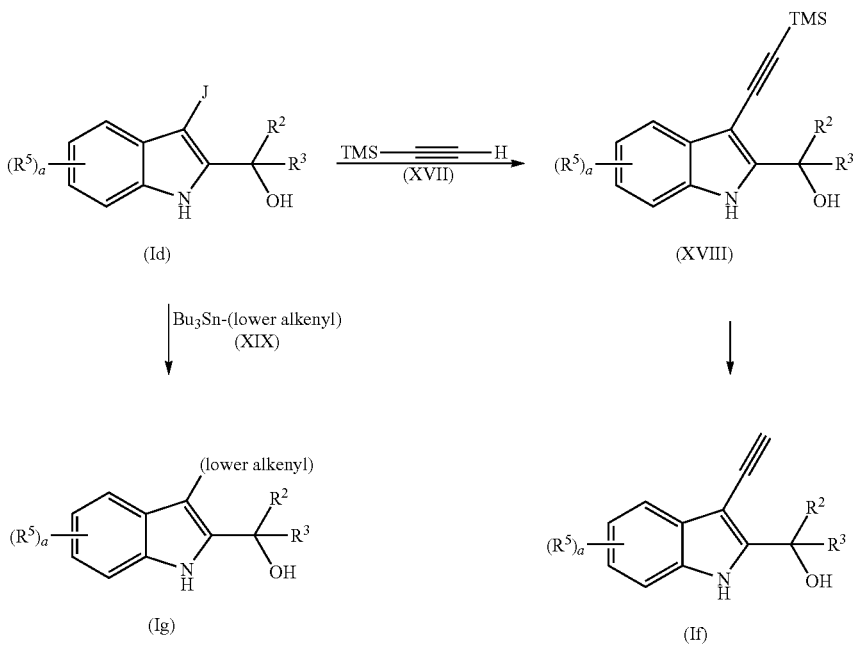

The compound of formula (Id) wherein J is Br or I, is reacted with a suitably substituted compound of formula (XVII), a known compound or compound prepared by known methods, in the presence of a catalyst such as $PdCl_2(PPh_3)_4$, $Pd_2(dba)_3$, $PdCl_2(dppf)$, and the like, in presence of CuI, in the presence of an organic base, pref- One skilled in the art will further recognize that compounds of formula (II) and compounds of formula (III) wherein $R^4$ is other than hydrogen may be similarly prepared according to the processes outlined in Scheme 3 and 4 above, by substituting a suitably substituted compound of formula (IIb) or a suitably substituted compound of formula (IIIb)

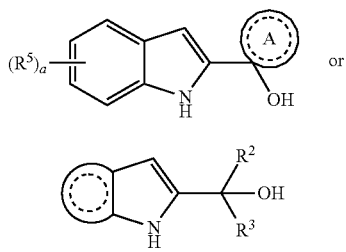

(IIb)

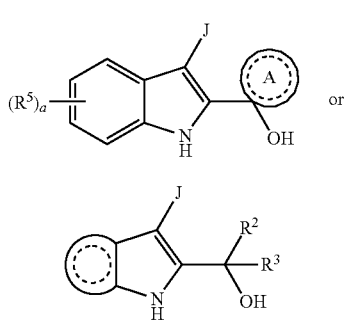

(IIIb)

for the compound of formula (Ib) in Scheme 3; or by substituting a suitably substituted compound of formula (IId) or a suitably substituted compound of formula (IIId)

(IId)

(IIId)

for the compound of formula (Id) in Scheme 4.

Compounds of formula (I), particularly compounds of formula (I) wherein $R^2$ is —(CH$_2$)$_{1-4}$—S(O)$_{0-2}$—$R^6$ may be prepared according to the process outlined in Scheme 5.

known methods, in the presence of a catalyst such as PdCl$_2$(PPh$_3$)$_2$, PdCl$_2$(dppf), Pd$_2$(dba), and the like, in the presence of CuI, in the presence of an organic base, preferably, a tertiary amine base such as TEA, DIPEA, pyridine, and the like, in an organic solvent such as THF, DMF, DMAC, and the like, to yield the corresponding compound of formula (Ih).

The compound of formula (Ih) is optionally de-protected according to known methods to yield the corresponding compound of formula (Ij). For example, when G is H or S—$R^6$, the compound of formula (Ih) may be reacted with a base such as NaOH, KOH, and the like, in an organic solvent or mixture thereof such as methanol/water, ethanol/water, THF/water, and the like, to yield the corresponding compound of formula (Ij) wherein G is H or —S—$R^6$, respectively. Alternatively, when G is OTBS, the compound of formula (Ih) may be reacted with a base such as NaOH, KOH, and the like, in an organic solvent or mixture thereof such as methanol/water, ethanol/water, THF/water, and the like, to yield the corresponding compound of formula (Ij) wherein the OTBS group (G) is converted to an —OH group.

Wherein the compound of formula (Ij) G is S—$R^6$, the compound of formula (Ij) is further optionally reacted with an oxidizing reagent such as OXONE®/TBAHS, mCPBA, and the like, in an organic solvent or mixture thereof such as ethyl acetate/water, methanol/water, DCM, ethyl acetate, and the like, to yield the corresponding compound of formula (Ik).

Alternatively, wherein the compound of formula (Ij) G is S—$R^6$, the compound of formula (Ij) is further optionally reacted with a compound of formula (XIX), a known compound or compound prepared by known methods, wherein E is Cl, Br or I, preferably, in the presence of a base such as NaH, potassium t-butoxide, and the like, in an organic

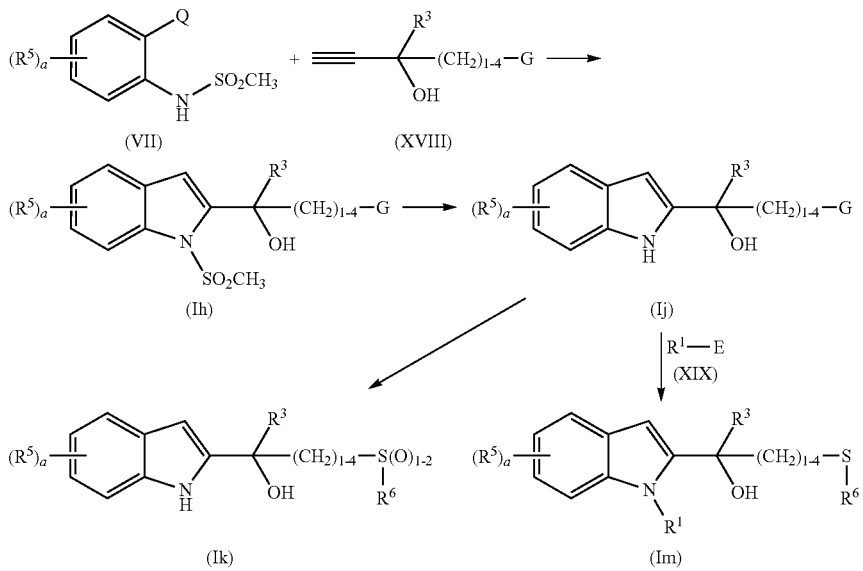

Scheme 5

Accordingly, a suitably substituted compound of formula (VII), wherein Q is I or Br, is reacted with a suitably substituted compound of formula (XVIII), wherein G is a selected from the group consisting of H, Cl, OTBS and S—$R^6$, a known compound or compound prepared by solvent such as THF, DMF, NMP, and the like, to yield the corresponding compound of formula (Im).

One skilled in the art will recognize that the compound of formula (Im) may be further optionally reacted with an oxidizing reagent such as OXONE®/TBAHS, mCPBA, and the like, in an organic solvent or mixture thereof such as ethyl acetate/water, methanol/water, DCM, ethyl acetate, and the like, to yield the corresponding compound wherein the —S— of the —(CH$_2$)$_{1-4}$—S—R$^6$ substituent group is oxidized to the corresponding —SO— or —SO$_2$— group.

One skilled in the art will further recognize that compounds of formula (III) wherein R$^2$ is —(CH$_2$)$_{1-4}$—S(O)$_{0-2}$—R$^6$ may similarly be prepared according to the process outlined in Scheme 5 by substitution of a suitably substituted compound of formula (XX)

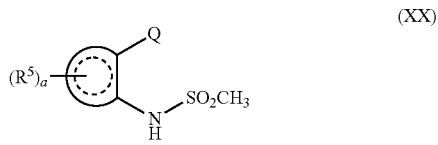

for the compound of formula (VII).

One skilled in the art will further recognize that compounds of formula (I) and compounds of formula (III) wherein R$^2$ is selected from —(CH$_2$)$_{1-4}$—O—R$^6$, —(CH$_2$)$_{1-4}$—NH—R$^6$ or —(CH$_2$)$_{1-4}$—N(lower alkyl)-R$^6$ may be similarly prepared according to the process outlined in Scheme 5 above, by selecting and substituting a suitably substituted compound of formula (XVIII) wherein G is replaced with an —O—R$^6$, —NH—R$^6$ or —N(lower alkyl)-R$^6$ group, respectively.

Compound of formula (I) wherein R$^2$ is selected from the group consisting of —(CH$_2$)$_{1-4}$—S(O)$_{0-2}$—R$^6$ and wherein R$^6$ is an optionally substituted aryl or an optionally substituted heteroaryl may alternatively be prepared from the corresponding compound of formula (Ih) wherein G is Cl, according to the process outlined in Scheme 6.

Scheme 6

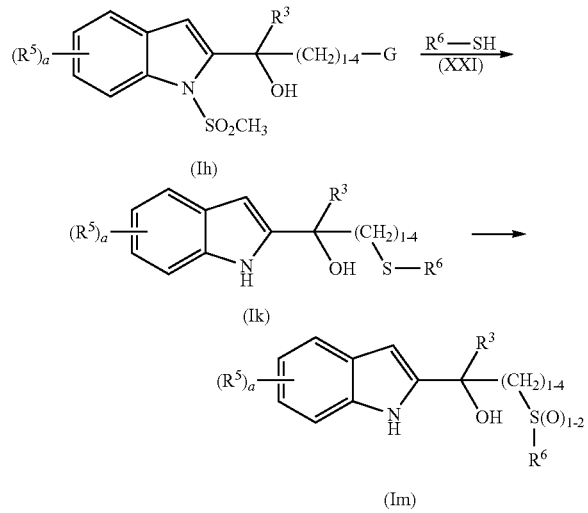

Accordingly, a suitably substituted compound of formula (Ih) wherein G is Cl, is reacted with a suitably substituted compound of formula (XXI), a known compound or compound prepared by known methods, in the presence of a base such as NaOCH$_3$, NaO(lower alkyl), TEA, and the like, in an organic solvent such as methanol, ethanol, THF, and the like, to yield the corresponding compound of formula (Ik).

The compound of formula (Ik) is reacted with a suitably selected oxidizing agent such as OXONE®/TBAHS, mCPBA, and the like, in an organic solvent or mixture thereof such as ethyl acetate/water, methanol/water, DCM, ethyl acetate, and the like, to yield the corresponding compound of formula (Im).

One skilled in the art will further recognize that compounds of formula (III) wherein R$^2$ is —(CH$_2$)$_{1-4}$—S(O)$_{0-2}$—R$^6$ may similarly be prepared according to the process outlined in Scheme 6 by substitution of a suitably substituted compound of formula (IIIh)

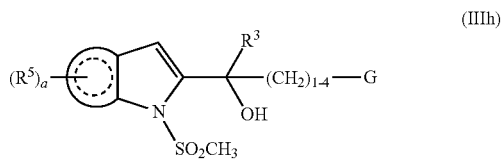

wherein G is Cl, for the compound of formula (IIIh).

Compounds of formula (I) wherein R$^2$ is selected from —(CH$_2$)$_{1-4}$—O—C(O)—R$^6$ may be prepared according to the process outlined in Scheme 7.

Scheme 7

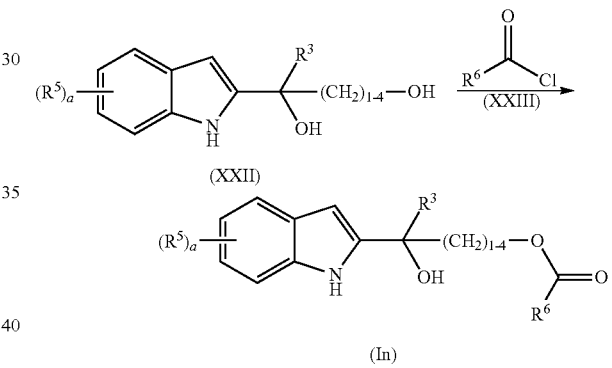

Accordingly, a suitably substituted compound of formula (XXII) (prepared as previously described in Scheme 5, de-protecting a compound of formula (Ih) wherein G is OTBS) is reacted with a suitably substituted acid chloride, a compound of formula (XXIII), a known compound or compound prepared by known methods, in the presence of an organic base, preferably, a tertiary amine base such a TEA, DIPEA, pyridine, and the like, in an organic solvent such as THF, DCM, acetonitrile, and the like, to yield the corresponding compound of formula (In).

One skilled in the art will further recognize that compounds of formula (III) wherein R$^2$ is —(CH$_2$)$_{1-4}$—O—C (O)—R$^6$ may similarly be prepared according to the process outlined in Scheme 7 by substitution of a suitably substituted compound of formula (IIIh)

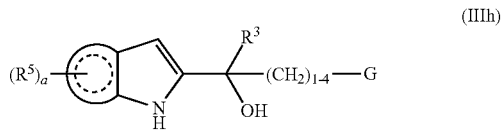

wherein G is OTBS, for the compound of formula (Ih).

Compounds of formula (I) wherein R¹ is other than hydrogen or wherein R⁷ is other than hydrogen may be prepared according to the process outlined in Scheme 8.

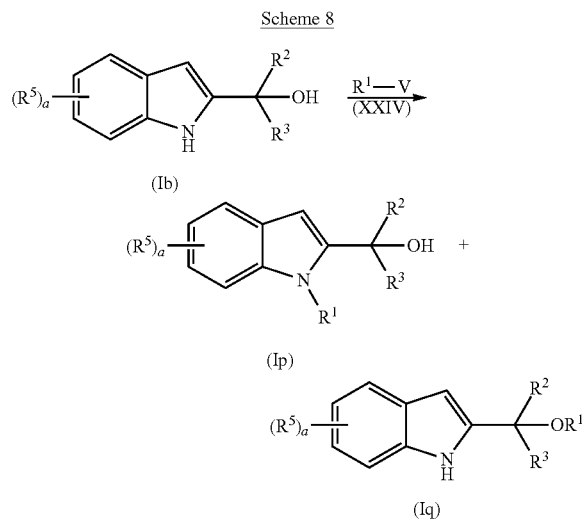

Accordingly, a suitably substituted compound of formula (Ib), is reacted with a suitably substituted compound of formula (XXIV), wherein V is Br, Cl or I, a known compound or compound prepared by known methods, in the presence of a base such as potassium t-butoxide, sodium hydride, and the like, in an organic solvent such as THF, DMF, DMAC, and the like, to yield a mixture of the corresponding compounds of formula (Ip) and (Iq).

One skilled in the art will further recognize that compounds of formula (II) and compounds of formula (III) wherein R¹ is other than hydrogen or R⁷ is other than hydrogen, may be similarly prepared according to the process outlined in Scheme 8, with substitution of suitably substituted compounds of formula (IIb) or (IIIb)

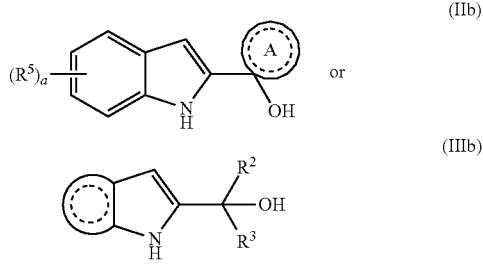

for the compound of formula (Ib).

One skilled in the art will further recognize that compounds of formula (I), compounds of formula (II) and/or compounds of formula (III) wherein b is other than 0 and/or wherein c is other than 0 may similarly be prepared according to any of the processes outlined in Schemes 2-8 by selecting and substituting suitably substituted reagents for those disclosed herein.

Compounds of formula (I) and compounds of formula (II) wherein X is O may be similarly prepared according to the processes described herein, with appropriate selection and substitution of suitable starting material.

For example, compounds of formula (I) may be prepared according to the process outlined in Scheme 1 by substituting a suitably substituted compound of formula (XXV)

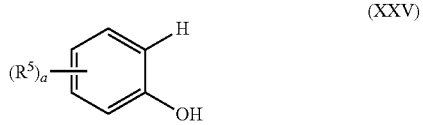

for the compound of formula (V).

Compounds of formula (I) and compounds of formula (II) wherein X is S may be prepared according to the process outlined in Scheme 9.

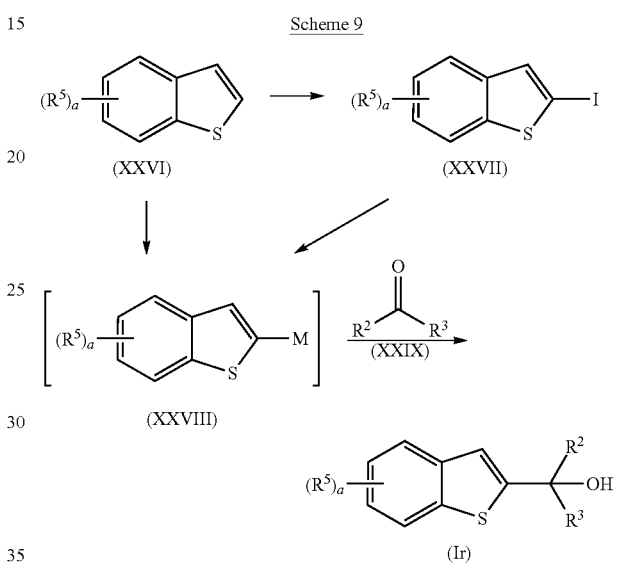

Accordingly, a suitably substituted compound of formula (XXVI), a known compound or compound prepared by known methods, is reacted with iodine or a source or iodine, according to known methods (for example, *J. Het. Chem.*, 15(2), 1978, pp 337-342), to yield the corresponding compound of formula (XXVII).

The compound of formula (XXVI) or the compound of formula (XXVII) is reacted according to known methods, to yield the corresponding compound of formula (XXVIII), wherein M is Li, Mg, Zn, Cu, and the like, and wherein the compound of formula (XXVIII) is preferably not isolated. The compound of formula (XXVIII) is reacted with a suitably substituted compound of formula (XXIX), a known compound or compound prepared by known methods, according to known methods (for example, *J. Med. Chem.*, 46(4), 2003, pp 532-541) to yield the corresponding compound of formula (Ir).

One skilled in the art will recognize that compounds of formula (I) wherein X is S and wherein R⁴, b and/or c are other then hydrogen and 0, respectively, may be similarly prepared according to the process outlined in Scheme 9 above by selecting and substituting suitably substituted reagents for the compounds of formula (XXVI).

One skilled in the art will further recognize that compounds of formula (II) wherein X is S may be similarly prepared according to the process outlined in scheme 9 above by selecting and substituting a suitably substituted cyclic ketone, for example a compound of formula (XXX)

(XXX)

for the compound of formula (XXIX).

Compounds of formula (IX) are known compounds or compounds which may be prepared by known methods. For example, compounds of formula (IX) may be prepared according to the process outlined in Scheme 10.

Scheme 10

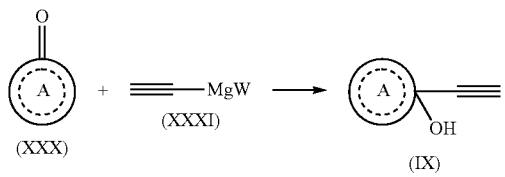

Accordingly, a suitably substituted compound of formula (XXX), a known compound or compound prepared by known methods, is reacted with a compound of formula (XXXI), wherein W is Br, Cl or I, a known compound or compound prepared by known methods, in an anhydrous organic solvent such as THF, diethyl ether, and the like, to yield the corresponding compound of formula (IX).

Compounds of formula (XVIII) are known compounds or compounds which may be prepared by known methods. For example, compounds of formula (XVIII) may be prepared according to the process outlined in Scheme 11.

Scheme 11

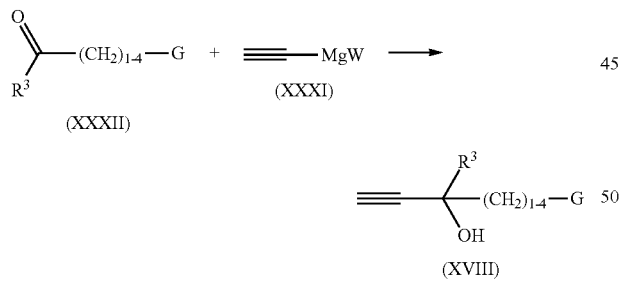

Accordingly, a suitably substituted compound of formula (XXXII), a known compound or compound prepared by known methods, wherein G is selected from the group consisting of H, Cl, OTBS and S—$R^6$, is reacted with a compound of formula (XXXI) wherein W is Br, Cl or I, a known compound, in an anhydrous organic solvent such as THF, diethyl ether, and the like, to yield the corresponding compound of formula (XVIII).

Compounds of formula (XI) and compounds of formula (XII) wherein $R^2$ is —$CH_2$—S—$R^6$ may alternatively be prepared according to the process outlined in Scheme 12.

Scheme 12

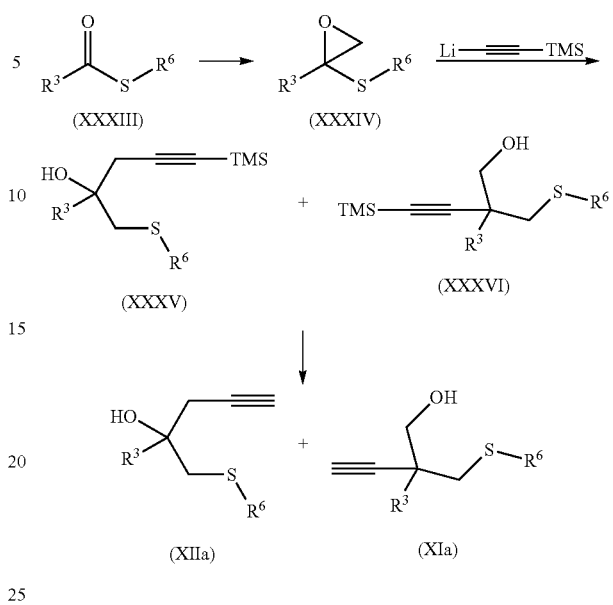

Accordingly, a suitably substituted compound of formula (XXXIII), a known compound or compound prepared by known methods, is reacted with $(CH_3)_3SI$, in the presence of a base such as sodium hydride, potassium hydride, and the like, in an organic solvent such as DMF, DMSO, and the like, to yield the corresponding compound of formula (XXXIV).

The compound of formula (XXXIV) is reacted with Li-CC-TMS, a known compound or compound prepared by known methods (for example by reacting HCC-TMS with butyl lithium), to yield a mixture of the compound of formula (XXXV) and (XXXVI).

The compound of formula (XXXV) and/or the compound of formula (XXXVI) (isolated or in a mixture) is reacted with a reagent such as TBAF, $K_2CO_3$, NaO(lower alkyl), and the like, in an organic solvent such as THF, methanol, ethanol, and the like, to yield the corresponding compound of formula (XIIa) and/or the corresponding compound of formula (XIa) (isolated or in a mixture), respectively.

Compounds of formula (XIV) wherein $R^2$ is —$(CH_2)_{1-4}$—S—$R^6$ may be prepared according to the process outlined in Scheme 13.

Scheme 13

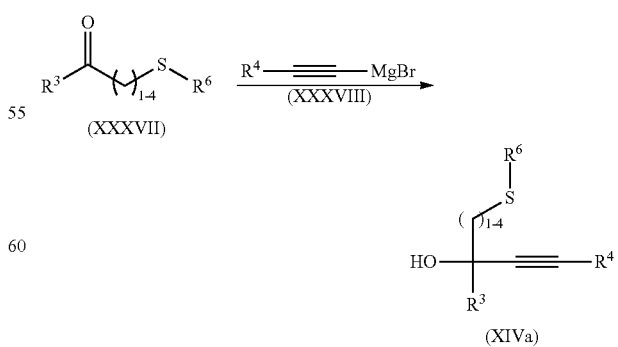

The compound of formula (XXXVII), a known compound or compound prepared by known methods, is reacted with a suitably substituted compound of formula (XXXVIII), a known compound or compound prepared by known methods, in an anhydrous organic solvent such as THF, diethyl ether, and the like, to yield the corresponding compound of formula (XIVa).

The following General Procedures are set forth to aid in the understanding of the invention, providing examples for completing selected steps in the synthesis of the compound of the present invention. These synthesis procedures are not intended and should not be construed to limit in any way the invention set forth in the claims which follow thereafter. In the general schemes described below,

represents phenyl or a six membered heteroaryl ring structure containing one to two N atoms.

EXAMPLE A

Oxidation

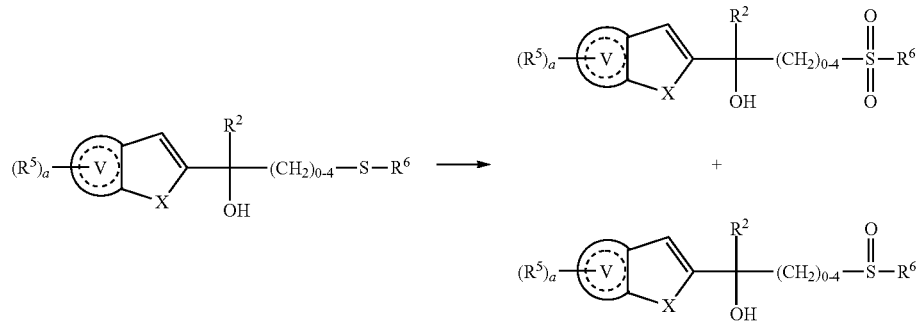

A suitably substituted sulfide is dissolved in a 1:1 mixture of dichloromethane and water and stirred rapidly. A catalytic amount of tetrabutylammonium hydrogensulfate is employed as a phase-transfer catalyst (PTC), added to the solution in an amount between about 1% and about 20%. Next 3 equivalents of OXONE® are added and the solution is stirred overnight at room temperature. The layers are separated and the aqueous layer is extracted with dichloromethane. The combined organic layers are washed with water and/or 10% sodium thiosulfate solution, then brine, dried over magnesium sulfate, filtered, and evaporated to yield a residue which is purified by column chromatography.

EXAMPLE B

De-Protection

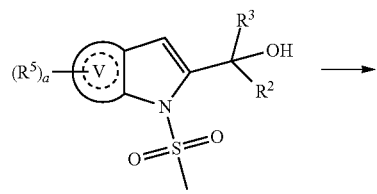

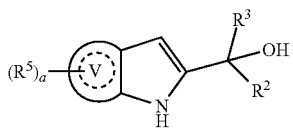

A suitably substituted protected indole derivative or intermediate is dissolved in methanol and about 1 to about 4 equivalents of sodium hydroxide solution (1 to 4 M) or lithium hydroxide dissolved in a minimal amount of water. The reaction mixture is stirred at temperature in the range of between about 0° C. to about 50° C., the reaction is allowed to proceed for about 0.5 hour to about overnight, and then the reaction mixture is concentrated under vacuum. Water is added to the residue and the solution is acidified with 1N hydrochloric acid solution. The aqueous solution is extracted twice with diethyl ether and the diethyl ether extracts are dried over magnesium sulfate, filtered, and concentrated under vacuum to yield a residue. The residue is purified by column chromatography.

EXAMPLE C

Sonogashira

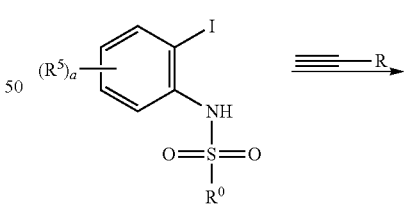

A suitably $R^0$ substituted protected aniline (wherein $R^0$ is a lower alkyl such as methyl, phenyl or tolyl) is added to a round-bottom flask along with about 5 to about 10 mole % of bis(triphenylphosphine) palladium(II) chloride and about 10 to about 25 mole % of copper iodide. The flask is fitted with a septum attached to an argon, nitrogen or alternative inert gas inlet. The solvent—tetrahydrofuran or dimethylformamide—is added via syringe followed by about 1.5 to about 2 equivalents of triethylamine or diethylamine. The solution is stirred for about 1 to about 30 minutes and a suitably substituted alkyne is added either neat or in a small amount of the solvent used in the reaction. The reaction is allowed to proceed for about 3 to about 24 hours. The solution is evaporated and the residue is purified by column chromatography.

EXAMPLE D

Alkyne

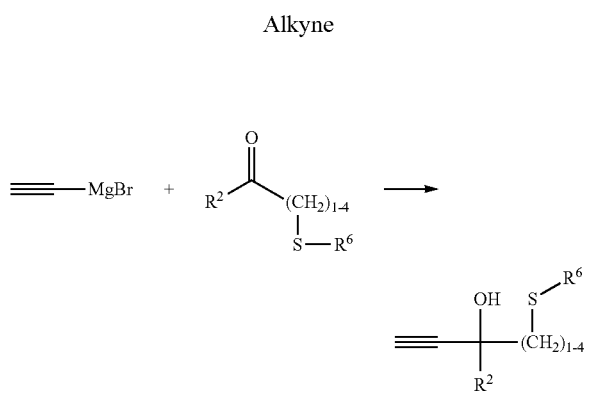

A 0.5 M solution of ethynylmagnesium bromide is cooled down in an ice bath under an argon atmosphere. A suitably substituted ketone is added in portions slowly via syringe and the reaction is allowed to proceed overnight. A solution of saturated ammonium chloride is added to the reaction and extracted twice with ethyl ether. The ethyl ether extracts are dried over magnesium sulfate, filtered, and evaporated to yield an oil. The oil is purified using a Kugelrohr or by column chromatography.

EXAMPLE E

Iodo Protected Aniline: Pyridine Method, Step 1

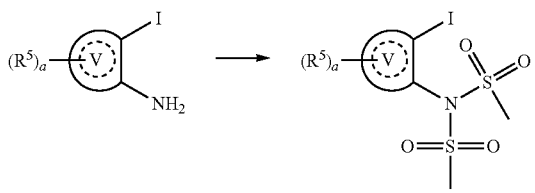

A suitably substituted aniline or derivative is dissolved in pyridine. About 5 equivalents of methanesulfonyl chloride is added and the solution is stirred overnight at room temperature. The solution is evaporated under vacuum and ethyl acetate is added to the residue and then decanted. This is done multiple times. The washes are combined and then washed with water, 1N hydrochloric acid solution, water and brine, then dried over magnesium sulfate, filtered and evaporated to yield a solid.

EXAMPLE F

Iodo Protected Aniline: Pyridine Method, Step 2

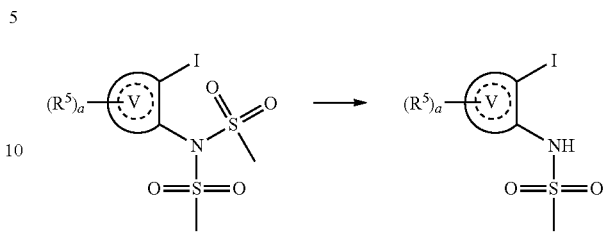

A solution of a suitably substituted bismethanesulfonate derivative in methanol is heated to about 50° C. in a water bath. Lithium hydroxide or sodium hydroxide (about 1.5 equivalents) in a minimal amount of water is added. The solution is stirred for about two hours at about 50° C. then allowed to proceed overnight at about room temperature. The solvent is removed under vacuum and water is added. The solution is acidified with 1N hydrochloric acid solution and a solid precipitates out. The solid is filtered off and washed with water and pentane. The solid is then taken up in ethyl acetate or diethyl ether and the organic solution is washed with water, dried over magnesium sulfate, filtered, evaporated to yield a solid.

EXAMPLE G

Iodo Protected Aniline: Potassium t-Butoxide Route

A suitably substituted iodoaniline or derivative is dissolved in THF and cooled in an ice bath under argon. Potassium t-butoxide (1.0M in THF) (about 3.2 equivalents) is added dropwise via syringe in portions over about one-half hour. The solution is stirred for about one-half hour and about 1.6 equivalents of methanesulfonyl chloride are added all at once. The reaction is allowed to go overnight. Water and 1N hydrochloric acid are added to the solution and then extracted twice with diethyl ether. The diethyl ether extracts are washed with water and brine, then dried over magnesium sulfate, filtered, and evaporated to yield a residue which is purified by column chromatography as necessary.

EXAMPLE H

Iodination

A suitably substituted aniline or derivative is dissolved in a 1:1 mixture of THF and methanol. About 1.1 equivalents of N-iodosuccinimide are then added, followed by addition of about 5 mol % of p-toluenesulfonic acid monohydrate. The solution is stirred overnight, then concentrated and diethyl ether is added. The solution is washed with water twice to remove succinimide, then washed with brine, dried over magnesium sulfate, filtered, evaporated to yield a solid which is triturated with pentane or hexanes to remove iodine. The solid is then again filtered and washed with pentane or hexanes and dried.

EXAMPLE I

Sulfide Displacement

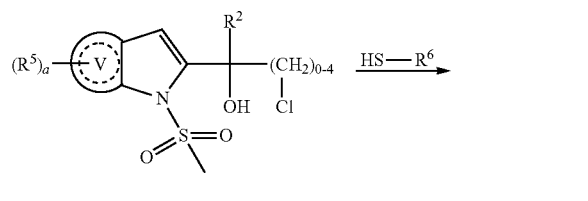

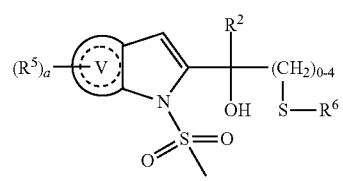

A suitably substituted alkyl chloride is dissolved in methanol. The anion of the substituted arylthio is prepared by dissolving the thiol in about an equimolar amount of 0.5M sodium methoxide in methanol. The thiolate solution (about 2 equivalents) is added to the alkyl chloride in methanol and stirred overnight. The solution is concentrated and 1N HCl is added, followed by extraction twice with ethyl ether. The ether extracts are dried over magnesium sulfate, filtered, and evaporated to yield a residue. The residue is purified by column chromatography.

The following Examples are set forth to aid in the understanding of the invention, and are not intended and should not be construed to limit in any way the invention set forth in the claims which follow thereafter.

In the Examples which follow, some synthesis products may be listed as having been isolated as a residue. It will be understood by one of ordinary skill in the art that the term "residue" does not limit the physical state in which the product was isolated and may include, for example, a solid, an oil, a foam, a gum, a syrup, and the like.

EXAMPLE 1

1-(3,4-Dichloro-phenylsulfanyl)-2-(5-nitro-6-trifluoromethyl-1H-indol-2-yl)-propan-2-ol

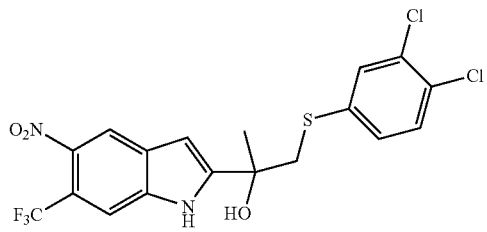 [SMILES: CC(O)(CSc1ccc(Cl)c(Cl)c1)c1cc2cc([N+](=O)[O-])c(C(F)(F)F)cc2[nH]1]

To a solution of 1-chloro-2-(1-methanesulfonyl-5-nitro-6-trifluoromethyl-1H-indol-2-yl)-propan-2-ol (1.0 g, 2.5 mmol) in methanol (10 mL) and tetrahydrofuran (10 mL) was added 3,4-dichlorobenzenethiol (0.64 mL, 5.0 mmol) followed by 0.5M sodium methoxide in methanol (10 mL, 5.0 mmol). The reaction mixture was stirred at room temperature overnight. The next day the solvent was evaporated and water was added and the solution was acidified with 1N HCl solution. The solution was extracted three times with ethyl acetate. The combined extracts were washed with brine, dried over magnesium sulfate, filtered, and evaporated to yield a yellow oil. The crude material (oil) was purified by column chromatography three times. The solvent systems used in the purification were of the following order: 5% diethyl ether in dichloromethane, 1% diethyl ether in dichloromethane, and 60% diethyl ether in pentane. The first product that came off was the tertiary sulfide of the title compound as a byproduct. The second product collected from the column was the title compound, a yellow solid.

MH−1=464, MH+23=488

EXAMPLE 2

1-Chloro-2-(1-methanesulfonyl-5-nitro-6-trifluoromethyl-1H-indol-2-yl)-propan-2-ol

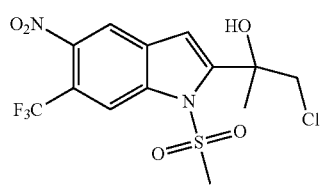 [SMILES: CC(O)(CCl)c1cc2cc([N+](=O)[O-])c(C(F)(F)F)cc2n1S(C)(=O)=O]

To a 500 mL round-bottom flask were added N-(2-iodo-4-nitro-5-trifluoromethyl-phenyl)-methanesulfonamide (4.3 g, 10.48 mmol), bis(triphenylphosphine) palladium (II) chloride (0.74 g, 1.048 mmol) and copper (I) iodide (0.40 g, 2.096 mmol). The solids were dissolved in tetrahydrofuran (100 ml) and triethylamine (2.2 mL, 15.72 mmol). The reaction mixture was then evacuated using an adapter fitted to the flask connected to a manifold with vacuum and nitrogen lines. Argon was bubbled into the solution. The flask was then filled with nitrogen and the process was repeated five times. To the reaction mixture was then added 1-chloro-2-methyl-but-3-yn-2-ol in a small amount of tetrahydrofuran (1.61 g, 11.53 mmol). The reaction was stirred overnight under nitrogen. The reaction mixture was concentrated and diethyl ether was added. Some material was observed to have crashed out. The mixture was filtered through Celite and the Celite was washed with diethyl ether. The filtrate was evaporated and the residue pre-absorbed onto silica gel. The residue was purified by column chromatography eluting with 70% dichloromethane in pentane to yield the title compound as a yellow solid.

MH−1=321, (loss of methanesulfonyl protecting group on indole ring)

EXAMPLE 3

1-Chloro-2-methyl-but-3-yn-2-ol

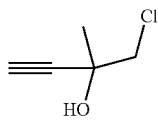

A solution of ethynyl magnesium bromide (0.5M in tetrahydrofuran, 200 mL, 100 mmol) was cooled in an ice bath under argon. Chloroacetone (8 mL, 100 mmol) was added in portions using a syringe. The solution was allowed to stir overnight at room temperature under argon. The reaction was worked-up by adding saturated ammonium chloride solution (100 mL). The solution was extracted twice with diethyl ether and the extracts washed with brine, dried over magnesium sulfate, filtered and evaporated to a brown oil. The oil was purified on a Kugelrohr as the temperature of the oven was ramped slowly to 70° C. under vacuum. Two bulbs were used to collect the distillate, which was collected to yield the title compound as an oil.

EXAMPLE 4

N-(2-Iodo-4-nitro-5-trifluoromethyl-phenyl)-methanesulfonamide

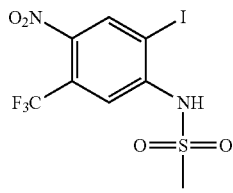 [SMILES: CS(=O)(=O)Nc1cc(C(F)(F)F)c([N+](=O)[O-])cc1I]

A solution of N-(2-iodo-4-nitro-5-trifluoromethyl-phenyl)-bismethanesulfonamide (18.85 g, 38.61 mmol) in methanol (250 mL) was heated to 50° C. in a water bath. Lithium hydroxide (1.39 g, 57.92 mmol) in a minimal amount of water was added. The solution was stirred for 2 hours, maintaining the temperature between 50 and 60° C., then let stir overnight at room temperature. The solvent was evaporated off and water was added. The water was decanted leaving a brown oil. The water was acidified to pH 1 using concentrated hydrochloric acid. An off-white solid precipitated was formed, it was filtered and washed with water and pentane and dried. The solid was dissolved in ethyl acetate and the solution washed with water, brine, dried over magnesium sulfate, filtered, and evaporated to yield the title compound as an orange solid.

MH−=409

EXAMPLE 5

N-(2-Iodo-4-nitro-5-trifluoromethyl-phenyl)-bis-methanesulfonamide

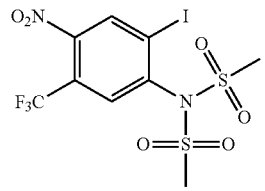 [SMILES: CS(=O)(=O)N(c1cc(C(F)(F)F)c([N+](=O)[O-])cc1I)S(C)(=O)=O]

To a solution of 2-iodo-4-nitro-5-trifluoromethyl-phenylamine (23.4 g, 70.5 mmol) in pyridine (80 mL) was added methanesulfonyl chloride (27.3 mL, 352.5). The reaction was allowed to proceed overnight at room temperature. The pyridine was evaporated and ethyl acetate was added multiple times to the residue and decanted off to yield a brown solid. The brown solid was then filtered off and washed with ethyl acetate. The combined washes were washed with water, 1N hydrochloric acid solution, water, brine, dried over magnesium sulfate, filtered, and evaporated to yield the title compound as a brown solid.

EXAMPLE 6

2-Iodo-4-nitro-5-trifluoromethyl-phenylamine

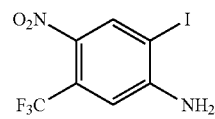 [SMILES: Nc1cc(C(F)(F)F)c([N+](=O)[O-])cc1I]

5-Amino-2-nitrobenzotrifluoride (16.25 g, 78.8 mmol) was dissolved in tetrahydrofuran (100 mL) and methanol (100 mL) and to this solution was added p-toluenesulfonic acid (0.18 g, 0.95 mmol) and N-iodosuccinimide (17.8 g, 78.8 mmol). The solution was stirred all day. N-iodosuccinimide (0.78 g, 3.47 mmol) and p-toluenesulfonic acid (0.2 g, 1.05 mmol) were then added and the solution stirred overnight at room temperature under nitrogen. The solution was concentrated under vacuum to a small volume. Water (200 mL) was added to the reaction mixture and a brown solid precipitated out. The solid was filtered and washed with water, then dissolved in ethyl acetate (100 mL) and diethyl ether (60 mL). The organic solution was washed with 10% sodium thiosulfate solution (50 mL). This created an emulsion which was alleviated by adding diethyl ether and water and filtering undissolved material. The layers were separated and the organic layer was washed with 10% sodium thiosulfate solution (50 mL), water was then added to the aqueous layer and the layers separated. The organic layer was washed with brine (50 mL), dried over magnesium sulfate, filtered, and evaporated to yield the title compound as a brown solid that was dried under vacuum.

MH−=331

EXAMPLE 7

1-(3,4-Dichloro-phenylsulfanyl)-2-(1-methanesulfonyl-5-nitro-6-trifluoromethyl-1H-indol-2-yl)-propan-2-ol

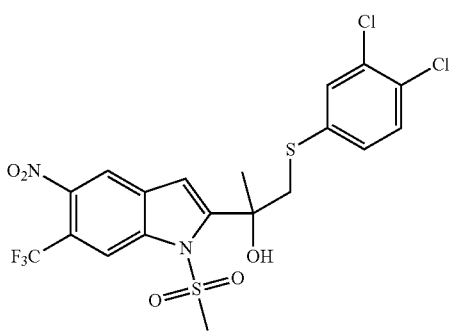 [SMILES: CC(O)(CSc1ccc(Cl)c(Cl)c1)c1cc2cc([N+](=O)[O-])c(C(F)(F)F)cc2n1S(C)(=O)=O]

A solution of 3,4-dichlorobenzenethiol (0.04 mL, 0.29 mmol) in DMF (3 mL) was prepared. To this solution was added diisopropylethylamine (0.05 mL, 0.29 mmol) after which the solution turned yellow. 1-Methanesulfonyl-2-(2-methyl-oxiranyl)-5-nitro-6-trifluoromethyl-1H-indole (53 mg, 0.145 mmol) in DMF (0.5 mL) was added via syringe and the reaction mixture stirred. After 2 hours the solution was added to water and 1N HCl. An off-white solid was filtered off, washed with water, and allowed to dry. The solid was purified by column chromatography eluting with dichloromethane to yield the title compound as an oil.

MH+Na=566

EXAMPLE 8

1-Methanesulfonyl-2-(2-methyl-oxiranyl)-5-nitro-6-trifluoromethyl-1H-indole

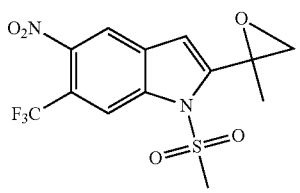 [SMILES: CC1(c2cc3cc([N+](=O)[O-])c(C(F)(F)F)cc3n2S(C)(=O)=O)CO1]

A solution of 2-isopropenyl-1-methanesulfonyl-5-nitro-6-trifluoromethyl-1H-indole (2.55 g, 7.32 mmol) in acetonitrile (18 mL) was prepared. Most of the solid was observed to dissolve in the acetonitrile. Water was added (2 mL) to the reaction mixture resulting in some cloudiness. N-bromosuccinimide was added (1.46 g, 8.20 mmol) followed by additional acetonitrile (5 mL). The reaction was allowed to proceed overnight. Water was added and the solution was extracted twice with diethyl ether. The diethyl ether extracts were washed with water, then brine, dried over magnesium sulfate, filtered, and evaporated to yield a residue. The residue was purified by column chromatography eluting with 30, 50, and 57% diethyl ether in pentane. Some mixed fractions with product were evaporated down and triturated with diethyl ether to yield the title product as a white solid which was filtered off.

MH+Na=387

MH−=285 (loss of methanesulfonyl group)

EXAMPLE 9

2-Isopropenyl-1-methanesulfonyl-5-nitro-6-trifluoromethyl-1H-indole

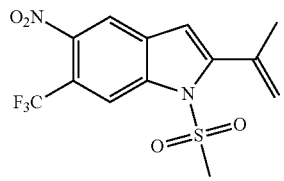 [SMILES: C=C(C)c1cc2cc([N+](=O)[O-])c(C(F)(F)F)cc2n1S(C)(=O)=O]

This compound was prepared using the general Sonagashira conditions as described in general Example C, starting from N-(2-iodo-4-nitro-5-trifluoromethyl-phenyl)-methanesulfonamide (9.0 g, 21.9 mmol) and 2-methyl-1-buten-3-yne (6.25 mL, 65.7 mmol) to yield the title compound as a reddish-brown solid.

EXAMPLE 10

1-(4-Chloro-phenylsulfanyl)-2-(1H-indol-2-yl)-propan-2-ol

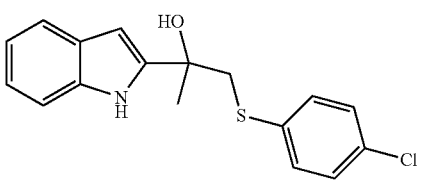 [SMILES: CC(O)(CSc1ccc(Cl)cc1)c1cc2ccccc2[nH]1]

A solution of 1-(4-chloro-phenylsulfanyl)-2-(1-methanesulfonyl-1H-indol-2-yl)-propan-2-ol (0.18 g, 0.46 mmol) in methanol (10 mL) was prepared. 1M Sodium hydroxide (3.2 mL, 3.2 mmol) was then added to the reaction mixture. The reaction did not go to completion after stirring overnight at room temperature. 3N Sodium hydroxide solution was then added and the solution became milky white. The solution gradually became clear. Diethyl ether was added and the layers separated. The aqueous layer was acidified with 1N HCl and extracted with diethyl ether. The diethyl ether extracts were washed with 1N HCl solution, water and brine, dried over magnesium sulfate, filtered, and evaporated to yield crude product. The crude material was purified by column chromatography eluting with 30 and 50% diethyl ether/pentane to yield the title compound as a solid.

MH−=316

EXAMPLE 11

1-(4-Chloro-phenylsulfanyl)-2-(1-methanesulfonyl-1H-indol-2-yl)-propan-2-ol

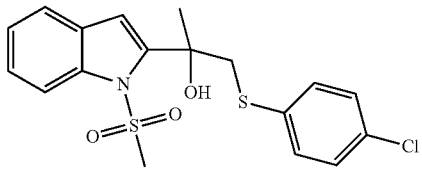 [SMILES: CC(O)(CSc1ccc(Cl)cc1)c1cc2ccccc2n1S(C)(=O)=O]

A solution of 1-chloro-2-(1-methanesulfonyl-1H-indol-2-yl)-propan-2-ol (0.36 g, 1.25 mmol) in methanol (12 mL) was prepared. To this solution was added 4-chlorothiophenol (0.36 g, 2.50 mmol) dissolved into 0.5 M sodium methoxide in methanol solution (5 mL, 2.50 mmol). The reaction was stirred overnight at room temperature. The solvent was evaporated and 1N HCl was added to the residue. The solution was extracted twice with diethyl ether and the diethyl ether extracts dried over magnesium sulfate, filtered and evaporated to yield a yellow oil. The oil was purified by column chromatography eluting with 30% diethyl ether/pentane to yield the title compound as a clear oil.

MH+Na=418

EXAMPLE 12

1-Chloro-2-(1-methanesulfonyl-1H-indol-2-yl)-propan-2-ol

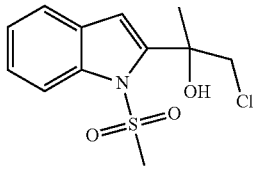 [SMILES: CC(O)(CCl)c1cc2ccccc2n1S(C)(=O)=O]

This compound was prepared using the general Sonagashira procedure as described in General Example C, from N-(2-iodo-phenyl)-methanesulfonamide (1.65 g, 5.55 mmol) and 1-chloro-2-methyl-but-3-yn-2-ol (0.79 g, 6.66 mmol) to yield a brown oil.

EXAMPLE 13

N-(2-Iodo-phenyl)-methanesulfonamide

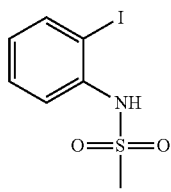

This compound was prepared using the general pyridine method, step 2 as described in General Procedures Example F, starting from N-(2-iodo-phenyl)-bismethanesulfonamide (19.27 g, 51.36 mmol) to yield the title compound as a brown solid.

MH−=296

EXAMPLE 14

N-(2-Iodo-phenyl)-bismethanesulfonamide

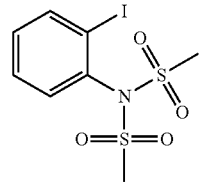 [SMILES: CS(=O)(=O)N(c1ccccc1I)S(C)(=O)=O]

This compound was prepared using the general pyridine method, step 1, as described in the General Procedure Example E, starting from 2-iodoaniline (20 g, 91.31 mmol) to yield the title compound as a brown solid.

MH−=296, loss of methanesulfonyl group

EXAMPLE 15

2-(5-Chloro-6-trifluoromethyl-1H-indol-2-yl)-1-(4-fluoro-benzenesulfonyl)-propan-2-ol

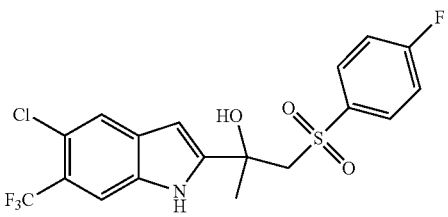 [SMILES: CC(O)(CS(=O)(=O)c1ccc(F)cc1)c1cc2cc(Cl)c(C(F)(F)F)cc2[nH]1]

To a solution of 2-(5-chloro-6-trifluoromethyl-1H-indol-2-yl)-1-(4-fluoro-phenylsulfanyl)-propan-2-ol (0.42 g, 1.04 mmol) in dichloromethane (10 mL) was added water (10 mL). The solution was stirred rapidly and tetrabutylammonium hydrogensulfate (12 mg, 0.035 mmol) was added followed by OXONE® (1.02 g, 1.66 mmol). The reaction mixture turned bright yellow and was allowed to proceed overnight at room temperature. The reaction mixture was diluted with water and dichloromethane, the layers were separated and the aqueous layer was extracted with dichloromethane. The combined organic layers were washed with water, twice with 10% sodium thiosulfate solution and brine, then dried over magnesium sulfate. The magnesium sulfate was filtered off and the filtrate was concentrated and pre-absorbed onto silica gel and purified by column chromatography eluting with 80% diethyl ether/pentane to yield the title product as a solid.

$^1$H NMR (400 MHz, CDCl$_3$) δ 8.88 (brs, 1H), 7.75 dd, J=5.0, 8.8 Hz, 2H), 7.70 (s, 1H), 7.53 (s, 1H), 7.05 (t, J=8.4, 2H), 6.04 (s, 1H), 4.76 (s, 1H), 3.71 (d, J=14.6, 1H), 3.65 (d, J=14.5, 1H), 1.85 (s, 3H)

MH−=434.

EXAMPLE 16

1-Ethanesulfinyl-2-(5-nitro-6-trifluoromethyl-1H-indol-2-yl)-propan-2-ol and

1-Ethanesulfonyl-2-(5-nitro-6-trifluoromethyl-1H-indol-2-yl)-propan-2-ol

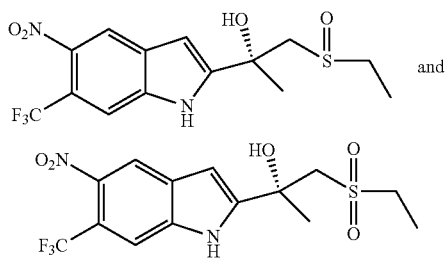

and

These compounds were prepared using the general oxidation procedure as described in the General Procedures Example A, employing less OXONE® (0.35 g, 0.57 mmol). The starting material was 1-ethylsulfanyl-2-(5-nitro-6-trifluoromethyl-1H-indol-2-yl)-propan-2-ol (Assigned stereochemistry is R) (0.4 g, 1.1 mmol). The crude material was purified by column chromatography eluting with 3% methanol in diethyl ether. The first compound that came off was Compound #156, which was isolated as a solid.

MH+23=403

The next compound that came off the column was Compound #155, which was isolated as a solid.

MH+23=387

EXAMPLE 17

1-Ethylsulfanyl-2-(5-fluoro-6-trifluoromethyl-1H-indol-2-yl)-propan-2-ol

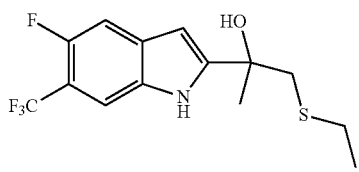 [SMILES: CCSCC(C)(O)c1cc2cc(F)c(C(F)(F)F)cc2[nH]1]

This compound was prepared using the general de-protection procedure as described in the General Procedure Example B. The starting material used was 1-ethylsulfanyl-2-(5-fluoro-1-methanesulfonyl-6-trifluoromethyl-1H-indol-2-yl)-propan-2-ol (0.8 g, 2.0 mmol) and the base used was 4M sodium hydroxide (1 mL, 4.0 mmol). The product was obtained as a solid.

MH+=304 which is a loss of water

EXAMPLE 18

1-Ethylsulfanyl-2-(5-fluoro-1-methanesulfonyl-6-trifluoromethyl-1H-indol-2-yl)-propan-2-ol

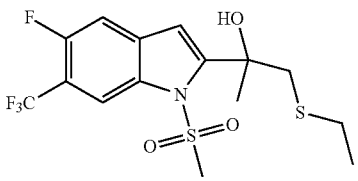 [SMILES: CCSCC(C)(O)c1cc2cc(F)c(C(F)(F)F)cc2n1S(C)(=O)=O]

This compound was prepared using the general Sonagashira procedure as described in the General Procedures Example C. The starting material was N-(4-fluoro-2-iodo-5-trifluoromethyl-phenyl)-methanesulfonamide (0.77 g, 2.0 mmol) and 1-ethylsulfanyl-2-methyl-but-3-yn-2-ol (0.29 g, 2.0 mmol), reacted to yield the title compound as a golden oil.

MH+Na=422

EXAMPLE 19

N-(4-Fluoro-2-iodo-5-trifluoromethyl-phenyl)-methanesulfonamide

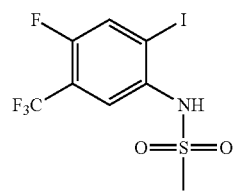 [SMILES: CS(=O)(=O)Nc1cc(C(F)(F)F)c(F)cc1I]

This compound was prepared using the general pyridine method, step 2 as described in the General Procedure Example F. The starting material was N-(4-fluoro-2-iodo-5-trifluoromethyl-phenyl)-bismethanesulfonamide (8.2 g, 17.8 mmol) which was reacted to yield the title compound as an orange solid.

MH−=382

EXAMPLE 20

N-(4-Fluoro-2-iodo-5-trifluoromethyl-phenyl)-bis-methanesulfonamide

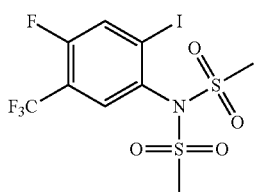 [SMILES: CS(=O)(=O)N(c1cc(C(F)(F)F)c(F)cc1I)S(C)(=O)=O]

This compound was prepared using the general pyridine procedure, step 1 as described in the General Procedure Example E. The starting material used was 4-fluoro-2-iodo-5-trifluoromethyl-phenylamine (5.6 g, 18.36 mmol), which was reacted to yield the title compound as a solid.

MH−=382, loss of methanesulfonyl group

EXAMPLE 21

4-Fluoro-2-iodo-5-trifluoromethyl-phenylamine

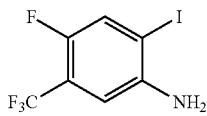 [SMILES: Nc1cc(C(F)(F)F)c(F)cc1I]

This compound was prepared using the standard iodination procedure, as described in General Procedures Example H, to yield the title compound as a reddish-brown oil.
MH+=306

EXAMPLE 22

2-(5-Amino-6-trifluoromethyl-1H-indol-2-yl)-1-ethylsulfanyl-propan-2-ol

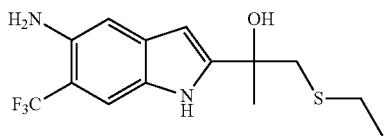 [SMILES: CCSCC(C)(O)c1cc2cc(N)c(C(F)(F)F)cc2[nH]1]

A solution of 1-ethylsulfanyl-2-(5-nitro-6-trifluoromethyl-1H-indol-2-yl)-propan-2-ol (0.35 g, 1.0 mmol) in ethanol (20 mL) was prepared. To the solution was then added saturated ammonium chloride solution (20 mL). Indium was added (1.15 g, 10 mmol) and the reaction heated to reflux. After one-half hour the reaction was complete. The reaction mixture was filtered through Celite and the Celite washed with water and diethyl ether. The layers were separated and the aqueous layer extracted with diethyl ether. The organic layers were dried over magnesium sulfate, filtered, and evaporated to yield a residue. The residue was dissolved in dichloromethane and purified by column chromatography eluting with 1:1 diethyl ether/hexanes to yield the title compound as a solid.
MH+=319

EXAMPLE 23

2-(2-Ethylsulfanyl-1-methoxy-1-methyl-ethyl)-5-nitro-6-trifluoromethyl-1H-indole

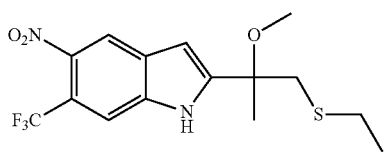 [SMILES: CCSCC(C)(OC)c1cc2cc([N+](=O)[O-])c(C(F)(F)F)cc2[nH]1]

This compound was prepared using the general de-protection procedure, as described in General Procedures Example. The starting material used was 2-(2-ethylsulfanyl-1-methoxy-1-methyl-ethyl)-1-methanesulfonyl-5-nitro-6-trifluoromethyl-1H-indole (0.17 g, 0.39 mmol). The base used was 4N sodium hydroxide (0.19 mL, 0.77 mmol). The title compound was obtained as a yellow solid.
M+23=385

EXAMPLE 24

2-(2-Ethylsulfanyl-1-methoxy-1-methyl-ethyl)-1-methanesulfonyl-5-nitro-6-trifluoromethyl-1H-indole

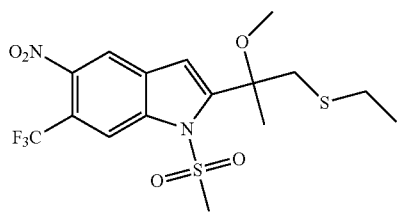 [SMILES: CCSCC(C)(OC)c1cc2cc([N+](=O)[O-])c(C(F)(F)F)cc2n1S(C)(=O)=O]

This compound was prepared using the standard Sonagashira procedure as described in General Procedures Example C. The starting material was N-(2-iodo-4-nitro-5-trifluoromethyl-phenyl)-methanesulfonamide (0.34 g, 0.82 mmol) and 4-ethylsulfanyl-3-methoxy-3-methyl-but-1-yne (0.13 g, 0.82 mmol), reacted to yield the title compound as a yellow film.

EXAMPLE 25

4-Ethylsulfanyl-3-methoxy-3-methyl-but-1-yne

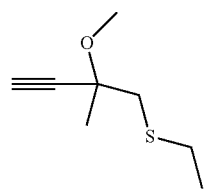

1-Ethylsulfanyl-2-methyl-but-3-yn-2-ol (0.29 g, 2.0 mmol) was added to a mixture of sodium hydride (60% dispersion in mineral oil, 88 mg, 2.2 mmol) in dimethylformamide (5 mL) under argon. Iodomethane (0.12 mL, 2.0 mmol) was then added to the reaction mixture via syringe and the mixture allowed to stir overnight. The mixture was poured onto water and extracted twice with diethyl ether. The diethyl ether extracts were washed with water and brine, dried over magnesium sulfate, filtered, and evaporated to yield a yellow oil. The oil was purified by column chromatography eluting with dichloromethane to yield the title compound as a clear liquid.
Product does not mass.

EXAMPLE 26

2-Ethanesulfinyl-1-(5-nitro-6-trifluoromethyl-1H-indol-2-yl)-ethanol

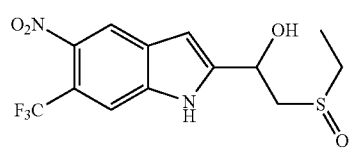 [SMILES: CCS(=O)CC(O)c1cc2cc([N+](=O)[O-])c(C(F)(F)F)cc2[nH]1]

This compound was prepared using the general oxidation procedure as described in General Procedures Example B, starting from 2-ethylsulfanyl-1-(5-nitro-6-trifluoromethyl-1H-indol-2-yl)-ethanol (0.36 g, 1.08 mmol) to yield the title compound as a solid.
MH+23(Na)=373, MH–=349

EXAMPLE 27

2-Ethylsulfanyl-1-(5-nitro-6-trifluoromethyl-1H-indol-2-yl)-ethanol

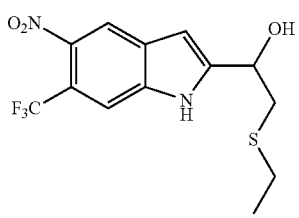 [SMILES: CCSCC(O)c1cc2cc([N+](=O)[O-])c(C(F)(F)F)cc2[nH]1]

This compound was prepared using the general de-protection procedure described in General Procedures Example B, starting from 2-ethylsulfanyl-1-(1-methanesulfonyl-5-nitro-6-trifluoromethyl-1H-indol-2-yl)-ethanol (1.52 g, 3.69 mmol) and 4M sodium hydroxide as base (1.8 mL, 7.38 mmol) to yield the title compound as a bright yellow solid.
MH–=333, MH+23(Na)=357.

EXAMPLE 28

2-Ethylsulfanyl-1-(1-methanesulfonyl-5-nitro-6-trifluoromethyl-1H-indol-2-yl)-ethanol

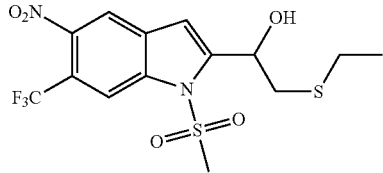 [SMILES: CCSCC(O)c1cc2cc([N+](=O)[O-])c(C(F)(F)F)cc2n1S(C)(=O)=O]

This compound was prepared using the general Sonagashira procedure as described in General Procedures Example C, starting from N-(2-iodo-4-nitro-5-trifluoromethyl-phenyl)-methanesulfonamide (1.89 g, 4.6 mmol) and 1-ethylsulfanyl-but-3-yn-2-ol (0.6 g, 4.6 mmol), reacted to yield the title compound as a yellow solid.
MH+23(Na)=435

EXAMPLE 29

Ethylsulfanyl-but-3-yn-2-ol

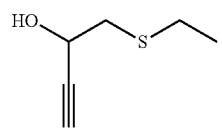

This compound was prepared from the general alkyne procedure as described in General Procedures Example D, starting from 0.5M ethynylmagnesium bromide (25 mL, 12.58 mmol) and ethylsulfanyl-acetaldehyde (1.31 g, 12.58 mmol), reacted to yield the title compound as a yellow oil.

EXAMPLE 30

2-(5-Nitro-6-trifluoromethyl-1H-indol-2-yl)-1-(2,2,2-trifluoro-ethylsulfanyl)-butan-2-ol

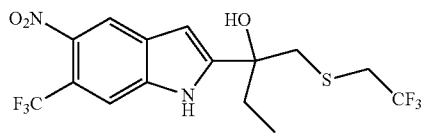 [SMILES: CCC(O)(CSCC(F)(F)F)c1cc2cc([N+](=O)[O-])c(C(F)(F)F)cc2[nH]1]

This compound was prepared using the standard de-protection procedure, as described in General Procedure Example B, starting from 2-(1-methanesulfonyl-5-nitro-6-trifluoromethyl-1H-indol-2-yl)-1-(2,2,2-trifluoro-ethylsulfanyl)-butan-2-ol (0.65 g, 1.31 mmol) and using 4N sodium hydroxide as base (1 mL, 4.0 mmol) to yield the title compound as a solid.
MH–=415, MH+23=439

EXAMPLE 31

2-(1-Methanesulfonyl-5-nitro-6-trifluoromethyl-1H-indol-2-yl)-1-(2,2,2-trifluoro-ethylsulfanyl)-butan-2-ol

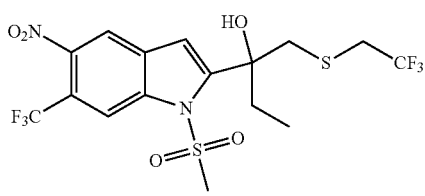 [SMILES: CCC(O)(CSCC(F)(F)F)c1cc2cc([N+](=O)[O-])c(C(F)(F)F)cc2n1S(C)(=O)=O]

This compound was prepared using the general Sonagashira procedure as described in General Procedures Example C, reacting N-(2-iodo-4-nitro-5-trifluoromethyl-phenyl)-methanesulfonamide (0.62 g, 1.5 mmol) and 3-(2,2,2-Trifluoro-ethylsulfanylmethyl)-pent-1yn-3-ol (0.32 g, 1.5 mmol) to yield the title compound as a yellow sticky oil.
MH+23=517, MH–=415, loss of methanesulfonyl group

EXAMPLE 32

2-(5-Chloro-6-trifluoromethyl-1H-indol-2-yl)-1-(2,2,2-trifluoro-ethylsulfanyl)-butan-2-ol

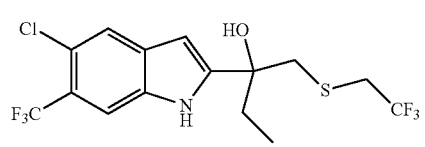 [SMILES: CCC(O)(CSCC(F)(F)F)c1cc2cc(Cl)c(C(F)(F)F)cc2[nH]1]

This compound was prepared using the standard deprotection procedure from, as described in General Procedures Example B, reacting 2-(5-chloro-1-methanesulfonyl-6-trifluoromethyl-1H-indol-2-yl)-1-(2,2,2-trifluoro-ethylsulfanyl)-butan-2-ol (0.24 g, 0.50 mmol) and using 4N sodium hydroxide as a base (0.37 mL, 0.50 mmol) to yield the title compound as a yellow sticky oil.

MH−=404

EXAMPLE 33

2-(5-Chloro-1-methanesulfonyl-6-trifluoromethyl-1H-indol-2-yl)-1-(2,2,2-trifluoro-ethylsulfanyl)-butan-2-ol

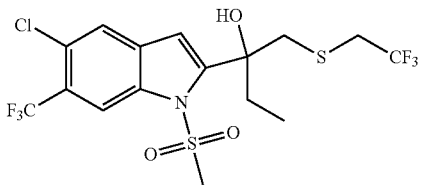 [SMILES: CCC(O)(CSCC(F)(F)F)c1cc2cc(Cl)c(C(F)(F)F)cc2n1S(C)(=O)=O]

This compound was prepared using the standard Sonagashira procedure as described in General Procedures Example C, reacting from N-(4-chloro-2-iodo-5-trifluoromethyl-phenyl)-methanesulfonamide (0.60 g, 1.5 mmol) and 3-(2,2,2-Trifluoro-ethylsulfanylmethyl)-pent-1yn-3-ol (0.32 g, 1.5 mmol) to yield the title compound as a yellow sticky oil.

MH−=404, loss of methanesulfonyl group

EXAMPLE 34

2-(3-Chloro-5-nitro-6-trifluoromethyl-1H-indol-2-yl)-1-(2,2,2-trifluoro-ethanesulfonyl)-butan-2-ol

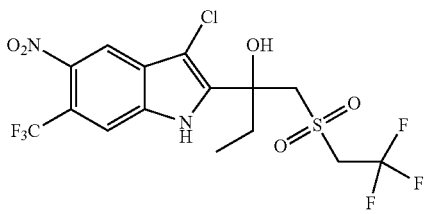 [SMILES: CCC(O)(CS(=O)(=O)CC(F)(F)F)c1[nH]c2cc(C(F)(F)F)c([N+](=O)[O-])cc2c1Cl]

A solution of 2-(5-nitro-6-trifluoromethyl-1H-indol-2-yl)-1-(2,2,2-trifluoro-ethanesulfonyl)-butan-2-ol (100 mg, 0.22 mmol) in tetrahydrofuran (5 mL) was prepared. To this solution was added N-chlorosuccinimide (33 mg, 0.25 mmol). The solution was stirred overnight at room temperature. Water was added and the solution extracted twice with diethyl ether. The diethyl ether extracts were dried over magnesium sulfate, filtered, and evaporated to yield a yellow oil. The oil was dissolved in diethyl ether and purified by column chromatography eluting with diethyl ether to yield the title compound as a yellow powder.

MH+23=505, MH−=481

EXAMPLE 35

2-(5-Nitro-6-trifluoromethyl-1H-indol-2-yl)-1-(2,2,2-trifluoro-ethanesulfonyl)-butan-2-ol

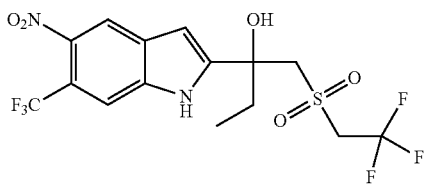 [SMILES: CCC(O)(CS(=O)(=O)CC(F)(F)F)c1cc2cc([N+](=O)[O-])c(C(F)(F)F)cc2[nH]1]

This compound was prepared using the general oxidation procedure as describe in General Procedures Example A. The starting material used was 2-(5-nitro-6-trifluoromethyl-1H-indol-2-yl)-1-(2,2,2-trifluoro-ethanesulfanyl)-butan-2-ol (0.25 g, 0.61 mmol), which was reacted to yield the title compound as a yellow, fluffy solid.

M+23=471

EXAMPLE 36

2-(5-Fluoro-6-trifluoromethyl-1H-indol-2-yl)-1-(2,2,2-trifluoro-ethylsulfanyl)-butan-2-ol

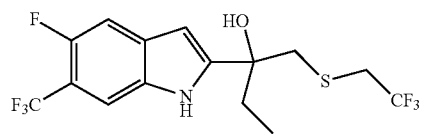 [SMILES: CCC(O)(CSCC(F)(F)F)c1cc2cc(F)c(C(F)(F)F)cc2[nH]1]

This compound was prepared using the general de-protection procedure as describe in General Procedures Example B, reacting 2-(5-fluoro-1-methanesulfonyl-6-trifluoromethyl-1H-indol-2-yl)-1-(2,2,2-trifluoro-ethylsulfanyl)-butan-2-ol (0.59 g, 1.26 mmol) and using 4N sodium hydroxide as base (1 mL, 4.0 mmol) to yield the title compound as a solid.

MH−=388

EXAMPLE 37

2-(5-Fluoro-1-methanesulfonyl-6-trifluoromethyl-1H-indol-2-yl)-1-(2,2,2-trifluoro-ethylsulfanyl)-butan-2-ol

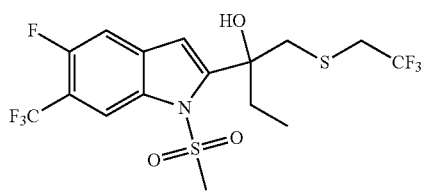 [SMILES: CCC(O)(CSCC(F)(F)F)c1cc2cc(F)c(C(F)(F)F)cc2n1S(C)(=O)=O]

This compound was prepared using the general Sonagashira procedure as describe in General Procedures Example C, reacting N-(4-fluoro-2-iodo-5-trifluoromethyl-phenyl)-methanesulfonamide (0.57 g, 1.5 mmol) and 3-(2, 2,2-trifluoro-ethylsulfanylmethyl)-pent-1yn-3-ol (0.32 g, 1.5 mmol) to yield the title compound as a brown oil.
MH+Na=490, MH−=388, loss of methanesulfonyl group

EXAMPLE 38

1-Butylsulfanyl-2-(5-nitro-6-trifluoromethyl-1H-indol-2-yl)-propan-2-ol

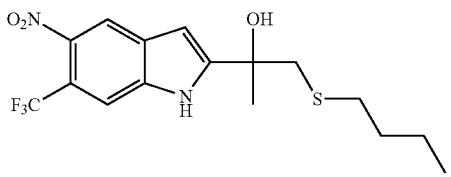 [SMILES: CCCCSCC(C)(O)c1cc2cc([N+](=O)[O-])c(C(F)(F)F)cc2[nH]1]

This compound was prepared using the general de-protection procedure as describe in General Procedures Example B. The starting material used was 1-butylsulfanyl-2-(1-methanesulfonyl-5-nitro-6-trifluoromethyl-1H-indol-2-yl)-propan-2-ol (0.53 g, 1.16 mmol). The base that was used was 4N sodium hydroxide solution (1 mL, 4 mmol). The title compound was obtained as a yellow sticky oil.
MH−=375

EXAMPLE 39

1-Butylsulfanyl-2-(1-methanesulfonyl-5-nitro-6-trifluoromethyl-1H-indol-2-yl)-propan-2-ol

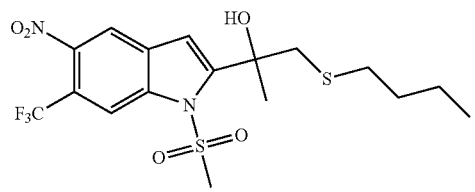 [SMILES: CCCCSCC(C)(O)c1cc2cc([N+](=O)[O-])c(C(F)(F)F)cc2n1S(C)(=O)=O]

This compound was prepared using the general Sonagashira procedure as describe in General Procedures Example C, reacting N-(2-iodo-4-nitro-5-trifluoromethyl-phenyl)-methanesulfonamide (0.82 g, 2.0 mmol) and 3-methyl-hept-1-yn-3-ol (0.34 g, 2.0 mmol) to yield the title compound as a yellow oil.
MH+23=477

EXAMPLE 40

1-Butylsulfanyl-2-methyl-but-3-yn-2-ol

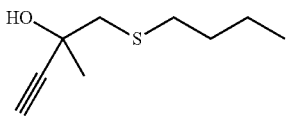

This compound was prepared using the general alkyne procedure as describe in General Procedures Example D, reacting 0.5M ethynylmagnesium bromide (35.6 mL, 17.78 mmol) and hexan-2-one (2.6 g, 17.78 mmol) to yield the title compound as a yellow liquid.

EXAMPLE 41

1-Butylsulfanyl-propan-2-one

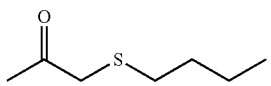

A solution of 1-butanethiol (2.1 mL, 20.0 mmol) in methanol (133 mL) was prepared and cooled in an ice bath under an argon atmosphere. 1M Sodium hydroxide was then added (20 mL, 20 mmol), followed by addition of chloroacetone (1.9 mL, 24.0 mmol). The reaction solution was stirred cold for two hours and then concentrated on a rotary evaporator. Water was added and the mixture extracted twice with diethyl ether. The diethyl ether extracts were dried over magnesium sulfate, filtered, and evaporated to yield a yellow oil. The oil was used without further purification.

EXAMPLE 42

2-(6-Chloro-5-fluoro-1H-indol-2-yl)-1-ethylsulfanyl-propan-2-ol

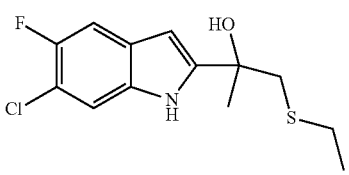 [SMILES: CCSCC(C)(O)c1cc2cc(F)c(Cl)cc2[nH]1]

To a solution of 2-(6-chloro-5-fluoro-1-methanesulfonyl-1H-indol-2-yl)-1-ethylsulfanyl-propan-2-ol (0.30 g, 0.82 mmol) in methanol (10 mL) was added 4M sodium hydroxide solution (0.4 mL). The reaction was allowed to proceed overnight at room temperature. Complete reaction was not achieved, so additional 1M sodium hydroxide solution (1 mL) was added and the reaction mixture was heated to 50° C. The reaction mixture was kept at 50° C. for two hours then allowed to stir overnight at room temperature. The reaction mixture was concentrated and to the concentrate was added 1N hydrochloric acid solution and water. The mixture was extracted twice with ethyl ether. The extracts were dried over $Mg_2SO_4$, filtered, and evaporated to yield a residue. The residue was purified by column chromatography eluting with dichloromethane to yield the title compound as a yellow oil.
MH−=286
$^1$H NMR (400 MHz, $CDCl_3$) δ 8.56 (brs, 1H), 7.35 (q, J=6.1 Hz, 1H), 2.57 (q, J=7.2 Hz, 2H), 1.05 (t, J=7.2 Hz, 3H).

EXAMPLE 43

2-(6-Chloro-5-fluoro-1-methanesulfonyl-1H-indol-2-yl)-1-ethylsulfanyl-propan-2-ol

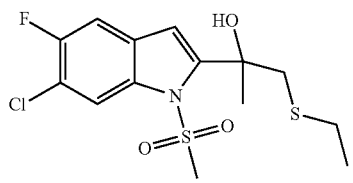 [SMILES: CCSCC(C)(O)c1cc2cc(F)c(Cl)cc2n1S(C)(=O)=O]

To a 50 mL round-bottom flask were added N-(5-chloro-4-fluoro-2-iodo-phenyl)-methanesulfonamide (0.30 g, 1.0 mmol), bis(triphenylphosphine) palladium(II) chloride (35 mg, 0.05 mmol) and copper (I) iodide (19 mg, 0.1 mmol). The flask was fitted with a septum and stirred under argon. Tetrahydrofuran (5 mL) and triethylamine (0.28 mL, 2.0 mmol) were then added via syringe. 1-Ethylsulfanyl-2-methyl-but-3-yn-2-ol (0.14 g, 1.0 mmol) in tetrahydrofuran (1 mL) was added via syringe and the reaction maintained with stirring at 50-60° C. for four hours. The solution was evaporated and the residue purified by column chromatography using dichloromethane as solvent to yield the title compound as a brown oil.

MH+Na=388, MH− shows a loss of water at 348

EXAMPLE 44

1-Ethylsulfanyl-2-methyl-but-3-yn-2-ol

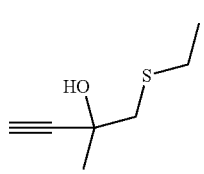

A solution of 0.5M ethynyl magnesium bromide (60 mL, 30 mmol) was cooled in an ice bath under argon. (Ethylthio) acetone (3.55 g, 30 mmol) was added dropwise via syringe. The reaction mixture was stirred overnight at room temperature. The reaction mixture was then poured onto a saturated ammonium chloride solution and then extracted twice with diethyl ether, dried over magnesium sulfate, filtered, and evaporated to yield a yellow oil. The oil was purified by column chromatography eluting with dichloromethane to yield the title compound as a yellow liquid.

EXAMPLE 45

2-(2-Ethylsulfanyl-1-hydroxy-1-methyl-ethyl)-6-trifluoromethyl-1H-indole-5-carbonitrile

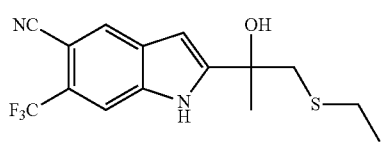 [SMILES: CCSCC(C)(O)c1cc2cc(C#N)c(C(F)(F)F)cc2[nH]1]

This compound was prepared using the general de-protection procedure as describe in General Procedures Example B, reacting 2-(2-ethylsulfanyl-1-hydroxy-1-methyl-ethyl)-1-methanesulfonyl-6-trifluoromethyl-1H-indole-5-carbonitrile (219 mg, 0.54 mmol) and using 4M sodium hydroxide (0.40 mL, 1.62 mmol) as the base, to yield the title compound as a white solid.

MH−=327

EXAMPLE 46

2-(2-Ethylsulfanyl-1-hydroxy-1-methyl-ethyl)-1-methanesulfonyl-6-trifluoromethyl-1H-indole-5-carbonitrile

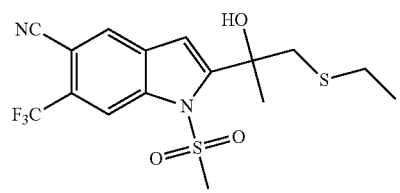 [SMILES: CCSCC(C)(O)c1cc2cc(C#N)c(C(F)(F)F)cc2n1S(C)(=O)=O]

This compound was prepared using the general Sonagashira procedure as describe in General Procedures Example C, reacting N-(4-cyano-2-iodo-5-trifluoromethyl-phenyl)-methanesulfonamide (1.0 g, 2.56 mmol) and 1-ethylsulfanyl-2-methyl-but-3-yn-2-ol (0.37 g, 2.56 mmol) to yield the title compound as a yellow sticky oil.

MH−=327, loss of methanesulfonyl group. MH+23(Na)=429

EXAMPLE 47

1-Cyclopentylsulfanyl-propan-2-one

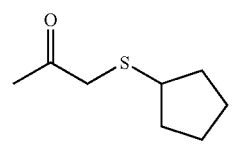

Cyclopentyl mercaptan (6.72 mL, 62.8 mmoL) in THF (50 mL) was treated with NaH (60%, 69.1 mmoL, 2.76 g) at 0° C. After bubbling ceased, chloroacetone (5.0 mL, 62.8 mmoL) was added into the reaction mixture via syringe slowly. The reaction mixture was then stirred at 0° C. for 2 hrs. The solvent was then removed and water and Et$_2$O were added. The Et$_2$O layer was washed with brine, dried over Na$_2$SO$_4$ and concentrated to yield the title compound as an oil.

$^1$H NMR (CDCl$_3$, 400 MHz) δ 3.22 (s, 2H), 2.95 (m, 1H), 2.28 (s, 3H), 2.05~1.48 (m, 8H).

EXAMPLE 48

1-Isopropylsulfanyl-propan-2-one

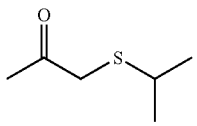

Isopropyl mercaptan (5.83 mL, 62.8 mmoL) in THF (50 mL) was treated with NaH (60%, 69.1 mmoL, 2.76 g) at 0° C. After bubbling ceased, chloroacetone (62.8 mmoL, 5 mL) was added into the reaction mixture via syringe slowly. The reaction mixture was then stirred at 0° C. for 2 hrs. The solvent was then removed and water and Et$_2$O were added. The Et$_2$O layer was washed with brine, dried over Na$_2$SO$_4$ and concentrated to yield the title compound as an oil.

$^1$H NMR (CDCl$_3$, 400 MHz) δ 3.25 (s, 2H), 2.95 (m, 1H), 2.30 (s, 3H), 1.20 (d, J=12.0 Hz, 3H), 1.15 (d, J=12.0 Hz, 3H).

EXAMPLE 49

1-(2,2,2-Trifluoro-ethylsulfanyl)-propan-2-one

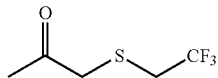

2,2,2-Trifluoroethanethiol (5.59 mL, 62.8 mmoL) in THF (50 mL) was treated with NaH (60%, 69.1 mmoL, 2.76 g) at 0° C. After bubbling ceased, chloroacetone (62.8 mmoL, 5 mL) was added into the reaction mixture via syringe slowly. The reaction mixture was then stirred at 0° C. for 2 hrs. The solvent was then removed and water and Et$_2$O were added. The Et$_2$O layer was washed with brine, dried over Na$_2$SO$_4$ and concentrated to yield the title compound as an oil.

$^1$H NMR (CDCl$_3$, 400 MHz) δ 3.40 (s, 2H), 3.15 (abq, J=12.0 Hz, 2H), 2.31 (s, 3H).

EXAMPLE 50

1-Isopropylsulfanyl-2-methyl-but-3-yn-2-ol

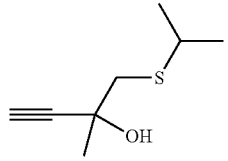

Ethynyl magnesium bromide (0.5 M in THF, 12.12 mmoL, 25 mL) was added dropwise into a solution of the compound prepared as in Example 48 (0.80 g, 6.06 mmoL) at 0° C. After addition, the reaction mixture was stirred for another 30 min at 0° C. Saturated NH$_4$Cl was added to quench the reaction. THF was removed and Et$_2$O was added. The aqueous phase was extracted with Et$_2$O and the combined organic layer was washed with brine, dried and concentrated to yield the crude title compound as a clear oil. The crude material was purified using column chromatography (silica gel, 4:1 hexanes:EtOAc as eluent) to yield the title compound as a colorless oil.

$^1$H NMR (CDCl$_3$, 400 MHz) δ 3.18 (m, 1H), 3.05 (d, J=10.5 Hz, 1H), 2.72 (d, J=10.5 Hz, 1H), 2.42 (s, 1H), 2.38 (s, 1H), 1.55 (s, 3H), 1.28 (d, J=13.5 Hz, 3H), 1.24 (d, J=13.5 Hz, 3H).

EXAMPLE 51

1-Cyclopentylsulfanyl-2-methyl-but-3-yn-2-ol

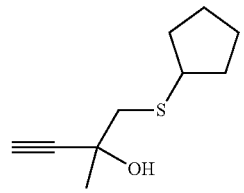

Ethynyl magnesium bromide (0.5 M in THF, 12.12 mmoL, 25 mL) was added dropwise into a solution of the compound prepared as in Example 47 (1.0 g, 6.33 mmoL) at 0° C. After addition, the reaction mixture was stirred for another 30 min at 0° C. Saturated NH$_4$Cl was added to quench the reaction. THF was removed and Et$_2$O was added. The aqueous phase was extracted with Et$_2$O and the combined organic layer was washed with brine, dried and concentrated to give the crude title compound as a clear oil. The crude material was purified using column chromatography (silica gel, 4:1 hexanes:EtOAc as eluent) to yield the title compound as a colorless oil.

$^1$H NMR (CDCl$_3$, 400 MHz) δ 3.30 (m, 1H), 3.21 (d, J=11.0 Hz, 1H), 2.75 (d, J=11.0 Hz, 1H), 2.42 (s, 1H), 2.05 (m, 2H), 1.80 (m, 2H), 1.55 (s, 3H), 1.60~1.40 (m, 4H).

EXAMPLE 52

2-Methyl-1-(2,2,2-trifluoro-ethylsulfanyl)-but-3-yn-2-ol

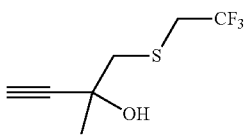

Ethynyl magnesium bromide (0.5 M in THF, 12.12 mmoL, 25 mL) was added dropwise into a solution of the compound prepared as in Example 49 (1.05 g, 6.10 mmoL) at 0° C. After addition, the reaction mixture was stirred for another 30 min at 0° C. Saturated NH$_4$Cl was added to quench the reaction. THF was removed and Et$_2$O was added. The aqueous phase was extracted with Et$_2$O and the combined organic layer was washed with brine, dried and concentrated to yield the crude title compound as a clear oil. The crude material was purified using column chromatography (silica gel, 4:1 hexanes:EtOAc as eluent) to yield the title compound as a colorless oil.

$^1$H NMR (400 MHz, CDCl$_3$) δ 3.40 (m, 1H), 3.25 (m, 1H), 3.10 (abq, J=12.5 Hz, 1H), 2.85 (abq, J=12.5 Hz, 1H), 2.78 (s, 1H), 2.54 (s, 1H), 1.60 (s, 3H).

EXAMPLE 53

1-Ethylsulfanyl-2-methyl-pent-3-yn-2-ol

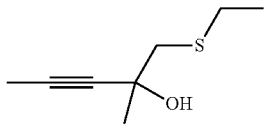

(Ethylthio)acetone (3.0 g, 25.4 mmoL) was treated dropwise with CH$_3$CCMgBr (0.5 M, 28.0 mmoL, 56 mL) at 0° C. After addition, the reaction was stirred for additional 30 min and then quenched with saturated NH$_4$Cl. THF was removed in vacuo. Water and Et$_2$O were added and the aqueous layer was exacted 3× with Et$_2$O. The combined organic layer was washed with brine, dried over anhydrous Na$_2$SO$_4$, filtered and concentrated to yield crude title product as a yellow oil. The crude material was then purified by column chromatography (silica gel, hexanes:EtOAc 6:1 as eluent) to yield the title compound as a colorless oil.

$^1$H NMR (CDCl$_3$, 400 MHz) δ 3.48 (dd, J=10.5, 4.8 Hz, 1H), 3.10 (s, 1H), 3.02 (d, J=15.0 Hz, 1H), 2.72 (dd, J=10.5, 2.0 Hz, 1H), 2.70 (d, J=15.0 Hz, 1H), 1.86 (s, 3H), 1.52 (s, 3H), 1.25 (t, J=15.0 Hz, 3H).

EXAMPLE 54

1-Benzylsulfanyl-2-(1-methanesulfonyl-5-nitro-6-trifluoromethyl-1H-indol-2-yl)-propan-2-ol

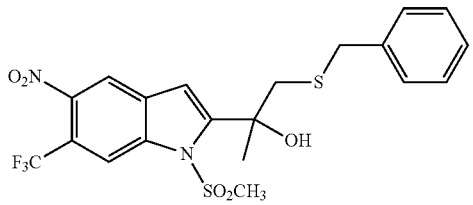 [SMILES: CC(O)(CSCc1ccccc1)c1cc2cc([N+](=O)[O-])c(C(F)(F)F)cc2n1S(C)(=O)=O]

The compound prepared as in Example 4 (500 mg, 1.32 mmoL), PdCl$_2$(Ph$_3$P)$_2$ (186 mg, 0.265 mmoL), CuI (50 mg, 0.265 mmoL) and TEA (1 mL, 6.70 mmoL) in THF (10 mL) was degassed with N$_2$ for 5 min. Benzylsulfanyl-2-methyl-but-3-yn-2-ol, the compound prepared as in Examples 49-52 substituting phenylmethyl-thiol for trifluoroethanethiol (300 mg, 1.46 mmoL) was added dropwise into the reaction mixture via syringe at room temperature. The reaction was stirred for 2 hrs. The solvent was then removed and Et$_2$O was added into the residue. The mixture was then filtrated through a pad of Celite and the filtrate was washed with brine, dried over anhydrous Na$_2$SO$_4$, then concentrated to yield a crude brown oil. The crude material was purified using column chromatography (silica gel, 3:1 hexanes:EtOAc as eluent) to yield the title compound as a yellow oil.

$^1$H NMR (CDCl$_3$, 400 MHz) δ 8.60 (s, 1H), 8.06 (s, 1H), 7.28~7.18 (m, 5H), 6.75 (s, 1H), 4.08 (s, 1H), 3.68 (s, 2H), 3.32 (s, 3H), 3.30 (d, J=12.0 Hz, 1H), 3.12 (d, J=12.0 Hz, 1H), 1.78 (s, 3H)

MS (m/z): 489 (M+H)$^+$

EXAMPLE 55

1-Benzylsulfanyl-2-(5-nitro-6-trifluoromethyl-1H-indol-2-yl)-propan-2-ol

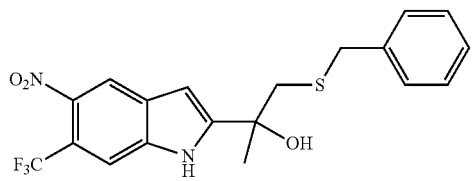 [SMILES: CC(O)(CSCc1ccccc1)c1cc2cc([N+](=O)[O-])c(C(F)(F)F)cc2[nH]1]

The compound prepared as in Example 54 (565 mg, 1.16 mmoL) in 4 N NaOH/MeOH solution (2 mL) was stirred at room temperature for 30 min. The solvent was removed. CH$_2$Cl$_2$ and H$_2$O were added. The organic layer was washed with brine and dried over anhydrous Na$_2$SO$_4$, then concentrated to yield a crude brown oil. The crude material was purified using column chromatography (silica gel, 3:1 hexanes:EtOAc as eluent) to yield the title compound as a light yellow solid.

$^1$H NMR (CDCl$_3$, 400 MHz) δ 9.18 (br, s, 1H), 8.18 (s, 1H), 7.75 (s, 1H), 7.35~7.14 (m, 5H), 6.42 (s, 1H), 3.69 (s, 2H), 3.08 (d, J=10.5 Hz, 1H), 2.92 (d, J=10.5 Hz, 1H), 1.62 (s, 3H)

MS (m/z): 411 (M+H)$^+$, 433 (M+Na)$^+$.

EXAMPLE 56

1-Isopropylsulfanyl-2-(1-methanesulfonyl-5-nitro-6-trifluoromethyl-1H-indol-2-yl)-propan-2-ol

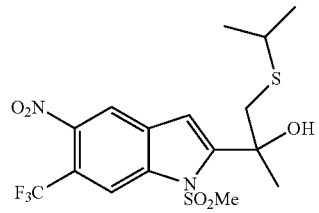

The compound prepared as in Example 4 (225 mg, 0.595 mmoL), PdCl$_2$(Ph$_3$P)$_2$ (84 mg, 0.119 mmoL), CuI (23 mg, 0.119 mmoL) and TEA (0.4 mL, 2.98 mmoL) in THF (10 mL) was degassed with N$_2$ for 5 min. The compound prepared in Example 50 (300 mg, 1.46 mmoL) was added dropwise into the reaction mixture via syringe at room temperature. The reaction was stirred for 2 hrs. The solvent was then removed and Et$_2$O was added into the residue. The mixture was then filtrated through a pad of Celite and the filtrate was washed with brine, dried over anhydrous Na$_2$SO$_4$, then concentrated to yield a crude brown oil. The crude material was purified using column chromatography (silica gel, 3:1 hexanes:EtOAc as eluent) to yield the title compound as a yellow oil.

$^1$H NMR (CDCl$_3$, 400 MHz) δ 8.65 (s, 1H), 8.16 (s, 1H), 6.85 (s, 1H), 4.08 (s, 1H), 3.50 (s, 3H), 3.48 (d, J=10.5 Hz, 1H), 3.15 (d, J=10.5 Hz, 1H), 2.92 (m, J=11.0 Hz, 1H), 1.82 (s, 3H), 1.22 (d, J=11.0 Hz, 6H)

MS (m/z): 441 (M+H)$^+$, 463 (M+Na)$^+$.

EXAMPLE 57

1-Isopropylsulfanyl-2-(5-nitro-6-trifluoromethyl-1H-indol-2-yl)-propan-2-ol

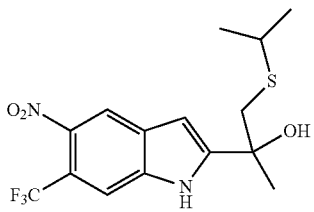 [SMILES: CC(C)SCC(C)(O)c1cc2cc([N+](=O)[O-])c(C(F)(F)F)cc2[nH]1]

The compound prepared as in Example 56 (125 mg, 0.284 mmoL) in 4 N NaOH/MeOH solution (2 mL) was stirred at room temperature for 30 min. The solvent was removed. CH$_2$Cl$_2$ and H$_2$O were added. The organic layer was washed with brine and dried over anhydrous Na$_2$SO$_4$, then concentrated to yield a crude brown oil. The crude material was purified using column chromatography (silica gel, 3:1 hexanes:EtOAc as eluent) to yield the title compound as a light yellow solid.

$^1$H NMR (CDCl$_3$, 400 MHz) δ 9.28 (br, s, 1H), 8.22 (s, 1H), 7.78 (s, 1H), 6.52 (s, 1H), 3.45 (br, s, 1H), 3.12 (s, 2H), 3.04 (d, J=10.5 Hz, 1H), 2.82 (m, 1H), 2.65 (d, J=10.5 Hz, 1H), 1.68 (s, 3H), 1.25 (d, J=11.0 Hz, 6H)

MS (m/z): 363 (M+H)$^+$.

EXAMPLE 58

2-(1-Methanesulfonyl-5-nitro-6-trifluoromethyl-1H-indol-2-yl)-1-(2,2,2-trifluoro-ethylsulfanyl)-propan-2-ol

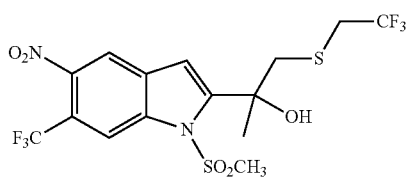 [SMILES: CC(O)(CSCC(F)(F)F)c1cc2cc([N+](=O)[O-])c(C(F)(F)F)cc2n1S(C)(=O)=O]

The compound prepared as in Example 4 (1.75 g, 4.63 mmoL), PdCl$_2$(Ph$_3$P)$_2$ (650 mg, 0.93 mmoL), CuI (177 mg, 0.93 mmoL) and TEA (3.23 mL, 23.15 mmoL) in THF (30 mL) were degassed with N$_2$ for 5 min. The compound prepared as in Example 52 (917 mg, 4.63 mmoL) was added dropwise into the reaction mixture via syringe at room temperature. The reaction was stirred for 2 hrs. The solvent was then removed and Et$_2$O was added into the residue. The mixture was then filtrated through a pad of Celite and the filtrate was washed with brine, dried over anhydrous Na$_2$SO$_4$, then concentrated to yield a crude brown oil. The crude material was purified using column chromatography (silica gel, 3:1 hexanes:EtOAc as eluent) to yield the title compound as a yellow oil.

$^1$H NMR (CDCl$_3$, 400 MHz) δ 8.62 (s, 1H), 8.11 (s, 1H), 6.82 (s, 1H), 4.05 (s, 1H), 3.55 (d, J=10.5 Hz, 1H), 3.40 (s, 3H), 3.32 (d, J=10.5 Hz, 1H), 3.25~3.12 (m, 2H), 1.82 (s, 3H)

MS (m/z): 481 (M+H)$^+$.

EXAMPLE 59

2-(5-Nitro-6-trifluoromethyl-1H-indol-2-yl)-1-(2,2,2-trifluoro-ethylsulfanyl)-propan-2-ol

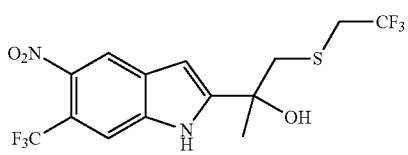 [SMILES: CC(O)(CSCC(F)(F)F)c1cc2cc([N+](=O)[O-])c(C(F)(F)F)cc2[nH]1]

The compound prepared as in Example 58 (1.45 g, 3.02 mmoL) in a 4N NaOH/MeOH solution (5 mL) was stirred at room temperature for 30 min. The solvent was removed. CH$_2$Cl$_2$ and H$_2$O were added. The organic layer was washed with brine and dried over anhydrous Na$_2$SO$_4$, then concentrated to yield a crude brown oil. The crude material was purified using column chromatography (silica gel, 3:1 hexanes:EtOAc as eluent) to yield the title compound as a light yellow solid.

$^1$H NMR (CDCl$_3$, 400 MHz) δ 9.25 (br, s, 1H), 8.21 (s, 1H), 7.80 (s, 1H), 6.48 (s, 1H), 3.25 (d, J=11.0 Hz, 1H), 3.15 (d, J=11.0 Hz, 1H), 3.10 (abq, J=10.5 Hz, 2H), 2.92 (s, 1H), 1.78 (s, 3H)

MS (m/z): 403 (M+H)$^+$, 425 (M+Na)$^+$.

Chiral separation, CH$_3$CN as eluent:
Peak 1, the (−) enantiomer
$[\alpha]_D^{20}$ −54 (c 0.21, MeOH)
Peak 2, the (+) enantiomer
$[\alpha]_D^{20}$ +56 (c 0.14, MeOH)

EXAMPLE 60

1-Cyclopentylsulfanyl-2-(1-methanesulfonyl-5-nitro-6-trifluoromethyl-1H-indol-2-yl)-propan-2-ol

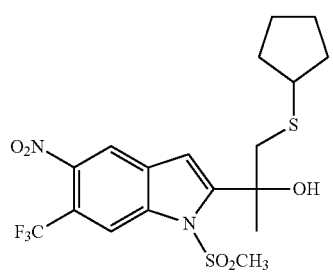 [SMILES: CC(O)(CSC1CCCC1)c1cc2cc([N+](=O)[O-])c(C(F)(F)F)cc2n1S(C)(=O)=O]

The compound prepared as in Example 4 (460 mg, 0.94 mmoL), PdCl$_2$(Ph$_3$P)$_2$ (132 mg, 0.188 mmoL), CuI (36 mg, 0.188 mmoL) and Et$_3$N (0.66 mL, 4.70 mmoL) in THF (10 mL) were degassed with N$_2$ for 5 min. The compound prepared as in Example 51 (190 mg, 1.034 mmoL) was added dropwise into the reaction mixture via syringe at room temperature. The reaction was stirred for 2 hrs. The solvent was then removed and Et$_2$O was added into the residue. The mixture was then filtrated through a pad of Celite and the filtrate was washed with brine, dried over anhydrous Na$_2$SO$_4$, then concentrated to yield a crude brown oil. The crude material was purified using column chromatography (silica gel, 3:1 hexanes:EtOAc as eluent) to yield the title compound as a yellow oil.

$^1$H NMR (CDCl$_3$, 400 MHz) δ 8.55 (s, 1H), 8.05 (s, 1H), 6.81 (s, 1H), 4.02 (s, 1H), 3.38 (d, J=11.5 Hz, 1H), 3.35 (s, 3H), 3.12 (d, J=11.5 Hz, 1H), 3.08 (m, 1H), 1.75 (s, 3H), 1.70~1.60 (m, 2H), 1.60~1.35 (m, 4H)

MS (m/z): 468 (M+H)$^+$, 490 (M+Na)$^+$.

EXAMPLE 61

1-Cyclopentylsulfanyl-2-(5-nitro-6-trifluoromethyl-1H-indol-2-yl)-propan-2-ol

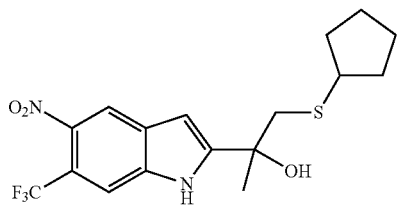 [SMILES: CC(O)(CSC1CCCC1)c1cc2cc([N+](=O)[O-])c(C(F)(F)F)cc2[nH]1]

The compound prepared as in Example 58 (395 mg, 0.848 mmoL) in a 4N NaOH/MeOH solution (5 mL) was stirred at room temperature for 30 min. The solvent was removed. CH$_2$Cl$_2$ and H$_2$O were added. The organic layer was washed with brine and dried over anhydrous Na$_2$SO$_4$, then concentrated to yield a crude brown oil. The crude material was purified using column chromatography (silica gel, 3:1 hexanes:EtOAc as eluent) to yield the title compound as a light yellow solid.

$^1$H NMR (CDCl$_3$, 400 MHz) δ 9.28 (br, s, 1H), 8.20 (s, 1H), 7.78 (s, 1H), 6.45 (s, 1H), 3.35 (s, 1H), 3.20 (d, J=11.0 Hz, 1H), 3.05 (d, J=11.0 Hz, 1H), 3.02 (m, 1H), 2.01 (m, 2H), 2.75 (m, 2H), 1.70 (s, 3H), 1.60~1.45 (m, 4H)

MS (m/z): 389 (M+H)$^+$.

EXAMPLE 62

2-(5-Nitro-6-trifluoromethyl-1H-indol-2-yl)-1-propylsulfanyl-propan-2-ol

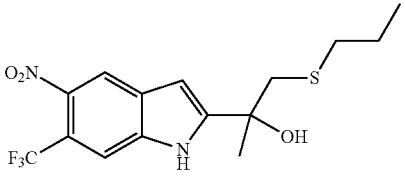 [SMILES: CCCSCC(C)(O)c1cc2cc([N+](=O)[O-])c(C(F)(F)F)cc2[nH]1]

The compound prepared as in Example 4 (300 mg, 0.732 mmoL), PdCl$_2$(Ph$_3$P)$_2$ (102 mg, 0.15 mmoL), CuI (29 mg, 0.15 mmoL) and Et$_3$N (0.26 mL, 1.83 mmoL) in THF (5 mL) was degassed with N$_2$ for 5 min. 2-Methyl-1-propyl-sulfanyl-but-3-yn-2-ol, the compound prepared as in Example 49-52 substituting propanethiol for trifluoroethanethiol (174 mg, 1.1 mmoL) was added dropwise into the reaction mixture via syringe at room temperature. The reaction was stirred for 2 hrs. The solvent was then removed and Et$_2$O was added into the residue. The mixture was then filtrated through a pad of Celite and the filtrate was washed with brine, dried over anhydrous Na$_2$SO$_4$, then concentrated to yield a brown oil. The crude material in 4N NaOH/MeOH solution (2 mL) was stirred at room temperature for 30 min. The solvent was removed. CH$_2$Cl$_2$ and H$_2$O were added. The organic layer was washed with brine and dried over anhydrous Na$_2$SO$_4$, then concentrated to yield a crude brown oil. The crude material was purified using column chromatography (silica gel, 3:1 hexanes:EtOAc as eluent) to yield the title compound as a light yellow solid.

$^1$H NMR (CDCl$_3$, 400 MHz) δ 9.26 (br, s, 1H), 8.22 (s, 1H), 7.79 (s, 1H), 6.48 (s, 1H), 3.39 (s, 1H), 3.20 (abq, J=14.3 Hz, 1H), 3.05 (abq, J=14.3 Hz, 1H), 2.46 (m, 2H), 1.69 (s, 3H), 1.58 (m, J=7.3 Hz, 2H), 0.94 (t, J=7.3 Hz, 3H)

MS (m/z): 363 (M+H)$^+$.

EXAMPLE 63

1-Ethylsulfanyl-2-(5-nitro-6-trifluoromethyl-1H-indol-2-yl)-butan-2-ol

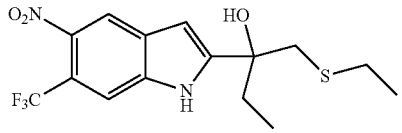 [SMILES: CCSCC(O)(CC)c1cc2cc([N+](=O)[O-])c(C(F)(F)F)cc2[nH]1]

The compound prepared as in Example 4 (300 mg, 0.732 mmoL), PdCl$_2$(Ph$_3$P)$_2$ (102 mg, 0.15 mmoL), CuI (29 mg, 0.15 mmoL) and Et$_3$N (0.26 mL, 1.83 mmoL) in THF (5 mL) was degassed with N$_2$ for 5 min. 3-Ethylsulfanyl-but-3-yn-2-ol, the compound prepared as in Example 49-52 substituting ethanethiol for trifluoroethanethiol and substituting 1-bromobutan-2-one for chloroacteone (174 mg, 1.1 mmoL) was added dropwise into the reaction mixture via syringe at room temperature. The reaction was stirred for 2 hrs. The solvent was then removed and Et$_2$O was added into the residue. The mixture was then filtrated through a pad of Celite and the filtrate was washed with brine, dried over anhydrous Na$_2$SO$_4$, concentrated to yield a crude brown oil. The crude oil in 4N NaOH/MeOH solution (2 mL) was stirred at room temperature for 30 min. The solvent was removed. CH$_2$Cl$_2$ and H$_2$O were added. The organic layer was washed with brine and dried over anhydrous Na$_2$SO$_4$, concentrated to yield a crude brown oil. The crude material was purified using column chromatography (silica gel, 3:1 hexanes:EtOAc as eluent) to yield the title compound as a light yellow solid.

$^1$H NMR (CDCl$_3$, 400 MHz) δ 9.35 (br, s, 1H), 8.25 (s, 1H), 7.78 (s, 1H), 6.45 (s, 1H), 3.40 (s, 1H), 3.21 (d, J=11.0 Hz, 1H), 3.05 (d, J=11.0 Hz, 1H), 2.75 (m, 1H), 2.60 (m, 1H), 1.98 (m, J=11.0 Hz, 2H), 1.20 (t, J=11.0 Hz, 3H), 0.90 (t, J=11.0 Hz, 3H)

MS (m/z): 363 (M+H)$^+$, 385 (M+Na)$^+$.

EXAMPLE 64

2-(1-Methanesulfonyl-5-nitro-6-trifluoromethyl-1H-indol-2-yl)-4-methylsulfanyl-butan-2-ol

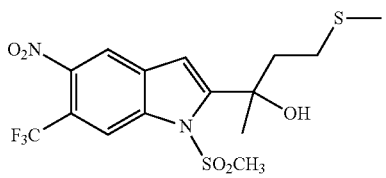 [SMILES: CSCCC(C)(O)c1cc2cc([N+](=O)[O-])c(C(F)(F)F)cc2n1S(C)(=O)=O]

The compound prepared as in Example 4 (300 mg, 0.732 mmoL), PdCl$_2$(Ph$_3$P)$_2$ (102 mg, 0.15 mmoL), CuI (29 mg, 0.15 mmoL) and Et$_3$N (0.25 mL, 1.83 mmoL) in THF (5 mL) was degassed with N$_2$ for 5 min. 3-Methyl-5-methylsulfanyl-pent-1-yl-3-ol, the compound prepared as in Example 52 substituting 4-methylsulfanyl-butan-2-one for 1-(2,2,2-trifluoroethylsulfanyl)-propan-2-one, (174 mg, 1.10 mmoL) was added dropwise into the reaction mixture via syringe at room temperature. The reaction was stirred for 2 hrs. The solvent was then removed and Et$_2$O was added into the residue. The mixture was then filtrated through a pad of Celite and the filtrate was washed with brine, dried over anhydrous Na$_2$SO$_4$, concentrated to yield a crude brown oil. The crude material was purified using column chromatography (silica gel, 3:1 hexanes:EtOAc as eluent) to yield the title compound as a yellow oil.

$^1$H NMR (CDCl$_3$, 400 MHz) δ 8.68 (s, 1H), 8.12 (s, 1H), 6.80 (s, 1H), 4.21 (s, 1H), 2.78 (m, 1H), 2.68 (m, 1H), 2.20 (s, 3H), 2.05 (m, 2H), 1.82 (s, 3H)

MS (m/z): 427 (M+H)$^+$.

EXAMPLE 65

4-Methylsulfanyl-2-(5-nitro-6-trifluoromethyl-1H-indol-2-yl)-butan-2-ol

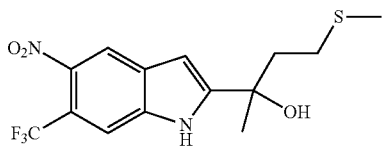 [SMILES: CSCCC(C)(O)c1cc2cc([N+](=O)[O-])c(C(F)(F)F)cc2[nH]1]

The compound prepared as in Example 64 (264 mg, 0.62 mmoL) in a 4N NaOH/MeOH solution (5 mL) was stirred at room temperature for 30 min. The solvent was removed. CH$_2$Cl$_2$ and H$_2$O were added. The organic layer was washed with brine and dried over anhydrous Na$_2$SO$_4$, concentrated to yield a crude brown oil. The crude material was purified using column chromatography (silica gel, 3:1 hexanes:EtOAc as eluent) to yield the title compound as a light yellow solid.

$^1$H NMR (CDCl$_3$, 400 MHz) δ 9.55 (br, s, 1H), 8.15 (s, 1H), 7.72 (s, 1H), 6.36 (s, 1H), 3.82 (s, 1H), 2.70 (m, 1H), 2.60 (m, 1H), 2.10 (s, 3H), 1.98 (m, 2H), 1.65 (s, 3H)

MS (m/z): 371 (M+H)$^+$, 719 (2M+Na)$^+$.

EXAMPLE 66

2-(5-Nitro-6-trifluoromethyl-1H-indol-2-yl)-1-(propane-1-sulfonyl)-propan-2-ol

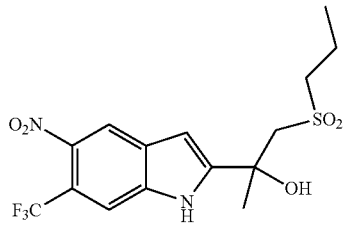 [SMILES: CCCS(=O)(=O)CC(C)(O)c1cc2cc([N+](=O)[O-])c(C(F)(F)F)cc2[nH]1]

The compound prepared as in Example 62 (75 mg, 0.21 mmoL) was dissolved in CH$_2$Cl$_2$ (2 mL) and H$_2$O (2 mL). OXONE® (176 mg, 0.31 mmoL) and Bu$_4$NHSO$_4$ (7 mg, 0.02 mmoL) were added in one portion into the reaction mixture. The mixture was stirred overnight. CH$_2$Cl$_2$ was added and the aqueous phase was extracted 3× with CH$_2$Cl$_2$. The combined organic phase was washed with brine, dried over anhydrous Na$_2$SO$_4$, then concentrated to yield a crude pale solid. The crude material was purified using column chromatography (silica gel, 1:1 hexanes:EtOAc as eluent) to yield the title compound as a white solid.

$^1$H NMR (CDCl$_3$, 400 MHz) δ 10.56 (s, br, 1H), 8.22 (s, 1H), 7.60 (s, 1H), 6.56 (s, 1H), 5.07 (s, 1H0, 3.74 (abq, J=14.7 Hz, 1H), 3.48 (abq, J=14.7 Hz, 1H), 2.80 (m, 2H), 1.88 (s, 3H), 1.81 (m, J=7.40 Hz, 2H), 0.94 (t, J=7.4 Hz, 3H)

MS (m/z): 395 (M+H)$^+$.

EXAMPLE 67

4-Methanesulfonyl-2-(5-nitro-6-trifluoromethyl-1H-indol-2-yl)-butan-2-ol and

4-Methanesulfinyl-2-(5-nitro-6-trifluoromethyl-1H-indol-2-yl)-butan-2-ol

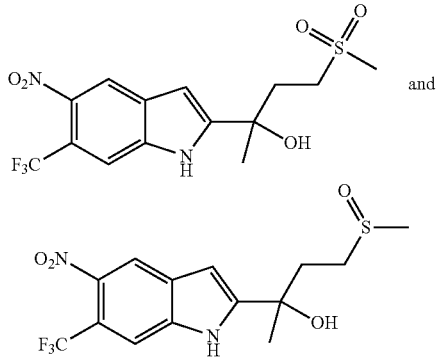

The compound prepared as in Example 65 (125 mg, 0.36 mmoL) was dissolved in CH$_2$Cl$_2$ (2 mL) and H$_2$O (2 mL). OXONE® (306 mg, 0.54 mmoL) and Bu$_4$NHSO$_4$ (12 mg, 0.036 mmoL) were added in one portion into the reaction mixture. The mixture was stirred overnight. CH$_2$Cl$_2$ was added and the aqueous phase was extracted 3× with CH$_2$Cl$_2$.

The combined organic phase was washed with brine, dried over anhydrous Na₂SO₄, concentrated to yield a crude pale solid. The crude material was purified using column chromatography (silica gel, 1:1 hexanes:EtOAc to 4:1 CH₂Cl₂: MeOH as eluent) to yield the title compounds as white solids.

4-Methanesulfonyl-2-(5-nitro-6-trifluoromethyl-1H-indol-2-yl)-butan-2-ol $^1$H NMR (CDCl$_3$, 400 MHz) δ 9.70 (s, 1H), 8.20 (s, 1H), 7.75 (s, 1H), 6.48 (s, 1H), 3.38 (br, s, 1H), 3.20 (m, 1H), 3.05 (m, 1H), 2.90 (s, 3H), 2.45 (m, 2H), 1.72 (s, 3H)
MS (m/z): 403 (M+Na)⁺.

4-Methanesulfinyl-2-(5-nitro-6-trifluoromethyl-1H-indol-2-yl)-butan-2-ol $^1$H NMR (CDCl$_3$, 400 MHz) δ 10.50 (s, br, 1H), 8.20 (s, 1H), 7.78 (s, 1H), 6.42 (s, 1H), 2.95 (m, 1H), 2.75 (m, 1H), 2.60 (s, 3H), 2.55 (t, J=10.5 Hz, 2H), 1.75 (s, 3H)
MS (m/z): 365 (M+H)⁺.

EXAMPLE 68

1-Ethanesulfonyl-2-(5-nitro-6-trifluoromethyl-1H-indol-2-yl)-butan-2-ol

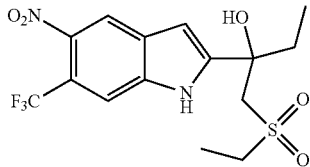 [SMILES: CCC(O)(CS(=O)(=O)CC)c1cc2cc([N+](=O)[O-])c(C(F)(F)F)cc2[nH]1]

The compound prepared as in Example 63 (105 mg, 0.29 mmoL) was dissolved in CH₂Cl₂ (2 mL) and H₂O (2 mL). OXONE® (306 mg, 0.54 mmoL) and Bu₄NHSO₄ (10 mg, 0.03 mmoL) were added in one portion into the reaction mixture. The mixture was stirred overnight. CH₂Cl₂ was added and the aqueous phase was extracted 3× with CH₂Cl₂. The combined organic phase was washed with brine, dried over anhydrous Na₂SO₄, then concentrated to yield a crude pale solid. The crude material was purified using column chromatography (silica gel, 1:1 hexanes:EtOAc as eluent) to yield the title compound as a white solid.

$^1$H NMR (CDCl$_3$, 400 MHz) δ 9.42 (s, br, 1H), 8.21 (s, 1H), 7.80 (s, 1H), 6.53 (s, 1H), 4.78 (s, 1H), 3.58 (d, J=12.0 Hz, 1H), 3.52 (d, J=12.0 Hz, 1H), 2.80 (q, J=10.5 Hz, 2H), 2.22 (m, 1H), 2.05 (m, 1H), 1.32 (t, J=10.5 Hz, 3H), 085 (t, J=11.0 Hz, 3H)
MS (m/z): 395 (M+H)⁺.

2-(2-Ethanesulfonyl-1-hydroxy-1-methyl-ethyl)-6-trifluoromethyl-1H-indole-5-carbonitrile, Compound #222

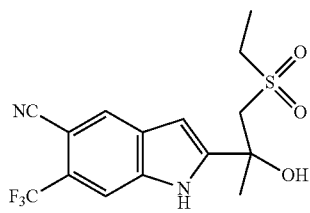 [SMILES: CCS(=O)(=O)CC(C)(O)c1cc2cc(C#N)c(C(F)(F)F)cc2[nH]1]

was similarly prepared according to the procedure described in Example 68 above, by reacting 2-(2-ethylsulfanyl-1-hydroxy-1-methyl-ethyl)-6-trifluoromethyl-1H-indole-5-carbonitrile, Compound #217.
MS calculated for C₁₅H₁₅F₃N₂O₃S: 360.08, found 359 (M−H).

2-(2-Ethanesulfonyl-1-hydroxy-1-methyl-ethyl)-3-methyl-6-trifluoromethyl-1H-indole-5-carbonitrile, Compound #251

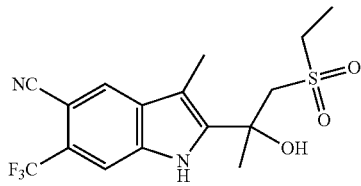 [SMILES: CCS(=O)(=O)CC(C)(O)c1[nH]c2cc(C(F)(F)F)c(C#N)cc2c1C]

was similarly prepared according to the procedure described in Example 68 above, by reacting 2-(2-ethylsulfanyl-1-hydroxy-1-methyl-ethyl)-3-methyl-6-trifluoromethyl-1H-indole-5-carbonitrile, Compound #233.
MS calculated for C₁₆H₁₇F₃N₂O₃S: 374.09, found 373 (M−H).

EXAMPLE 69

2-(5-Nitro-6-trifluoromethyl-1H-indol-2-yl)-1-(2,2,2-trifluoro-ethanesulfonyl)-propan-2-ol and 2-(5-Nitro-6-trifluoromethyl-1H-indol-2-yl)-1-(2,2,2-trifluoro-ethanesulfinyl)-propan-2-ol

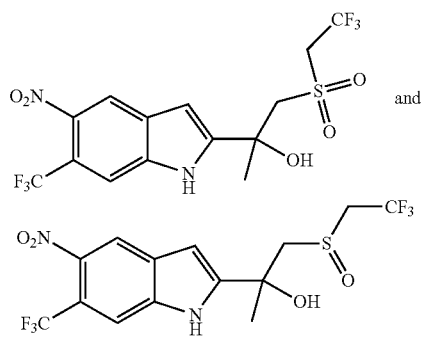

The compound prepared as in Example 59 (201 mg, 0.5 mmoL) was dissolved in CH₂Cl₂ (2 mL) and H₂O (2 mL). OXONE® (425 mg, 0.75 mmoL) and Bu₄NHSO₄ (17 mg, 0.05 mmoL) were added in one portion into the reaction mixture. The mixture was stirred overnight. CH₂Cl₂ was added and the aqueous phase was extracted 3× with CH₂Cl₂. The combined organic phase was washed with brine, dried over anhydrous Na₂SO₄, then concentrated to yield a crude pale solid. The crude material was purified using column chromatography (silica gel, 1:1 hexanes:EtOAc first and then 4:1 CH₂Cl₂: MeOH as eluent) to yield the title compounds as white solids.

2-(5-Nitro-6-trifluoromethyl-1H-indol-2-yl)-1-(2,2,2-trifluoro-ethanesulfonyl)-propan-2-ol $^1$H NMR (CD$_3$OD, 400 MHz) δ 8.25 (s, 1H), 7.85 (s, 1H), 6.65 (s, 1H), 4.45~4.30 (m, 2H), 3.78 (d, J=10.5 Hz, 1H), 3.20 (d, J=10.5 Hz, 1H), 1.90 (s, 3H)

MS (m/z): 457 (M+Na)$^+$.

2-(5-Nitro-6-trifluoromethyl-1H-indol-2-yl)-1-(2,2,2-trifluoro-ethanesulfinyl)-propan-2-ol $^1$H NMR (CD$_3$OD, 400 MHz) δ 8.25 (s, 1H), 7.90 (s, 1H), 6.70 (s, 1H), 4.05 (m, 1H), 3.75 (m, 1H), 3.68 (d, J=13.0 Hz, 1H), 3.45 (d, J=13.0 Hz, 1H), 1.86 (s, 3H)

MS (m/z): 441 (M+Na)$^+$.

EXAMPLE 70

2-(5-Nitro-6-trifluoromethyl-1H-indol-2-yl)-1-phenylmethanesulfonyl-propan-2-ol and 2-(5-Nitro-6-trifluoromethyl-1H-indol-2-yl)-1-phenylmethanesulfinyl-propan-2-ol

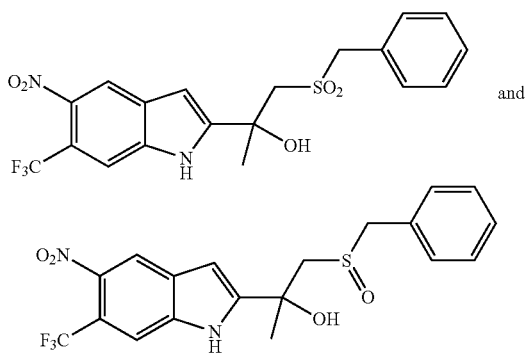

The compound prepared as in Example 55 (252 mg, 0.61 mmoL) was dissolved in CH$_2$Cl$_2$ (2 mL) and H$_2$O (2 mL). OXONE® (380 mg, 0.67 mmoL) and Bu$_4$NHSO$_4$ (5 mg, 0.06 mmoL) were added in one portion into the reaction mixture. The mixture was stirred overnight. CH$_2$Cl$_2$ was added and the aqueous phase was extracted 3× with CH$_2$Cl$_2$. The combined organic phase was washed with brine, dried over anhydrous Na$_2$SO$_4$, then concentrated to yield a crude pale solid. The crude material was purified using column chromatography (silica gel, 1:1 hexanes:EtOAc first and then 4:1 CH$_2$Cl$_2$:MeOH as eluent) to yield the title compounds as white solids.

2-(5-Nitro-6-trifluoromethyl-1H-indol-2-yl)-1-phenylmethanesulfonyl-propan-2-ol $^1$H NMR (CD$_3$OD, 400 MHz) δ 8.25 (s, 1H), 7.88 (s, 1H), 7.42 (m, 2H), 7.35 (m, 3H), 6.65 (s, 1H), 4.45 (s, 2H), 3.55 (abq, J=11.5 Hz, 2H), 3.30 (s, 1H), 1.90 (s, 3H)

MS (m.z): 443 (M+H)$^+$.

2-(5-Nitro-6-trifluoromethyl-1H-indol-2-yl)-1-phenylmethanesulfinyl-propan-2-ol $^1$H NMR (CD$_3$OD, 400 MHz) δ 8.21 (s, 1H), 7.88 (s, 1H), 7.35~7.25 (m, 5H), 6.55 (s, 1H), 4.20 (d, J=11.0 Hz, 1H), 4.05 (d, J=11.0 Hz, 1H), 3.48 (d, J=11.5 Hz, 1H), 3.28 (d, J=11.5 Hz, 1H), 1.80 (s, 3H)

MS (m/z): 427 (M+H)$^+$.

EXAMPLE 71

5-Chloro-2-isopropenyl-1-methanesulfonyl-6-trifluoromethyl-1H-indole

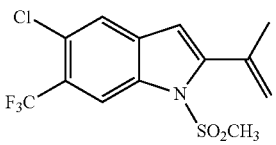 [SMILES: C=C(C)c1cc2cc(Cl)c(C(F)(F)F)cc2n1S(C)(=O)=O]

N-(4-cyano-2-iodo-5-trifluoromethyl-phenyl)-methanesulfonamide, the compound prepared as in Examples 81-82 (2.28 g, 5.69 mmoL), PdCl$_2$(Ph$_3$P)$_2$ (799 mg, 1.14 mmoL) and CuI (271 mg, 1.42 mmoL) in Et$_3$N (10 mL) was degassed with N$_2$ for 5 min. 2-Methyl-1-buten-3-yne (1.06 mL, 11.38 mmoL) was added dropwise into the reaction mixture via syringe at room temperature. The reaction was stirred for 3 hrs. The solvent was then removed and Et$_2$O was added into the residue. The mixture was then filtrated through a pad of Celite and the filtrate was washed with brine, dried over anhydrous Na$_2$SO$_4$, then concentrated to yield a crude brown oil. The crude material was purified using column chromatography (silica gel, 3:1 hexanes:EtOAc as eluent) to yield the title compound as a yellow oil.

$^1$H NMR (CDCl$_3$, 400 MHz) δ 8.40 (s, 1H), 7.72 (s, 1H), 6.51 (s, 1H), 5.31 (s, 1H), 5.20 (s, 1H), 2.92 (s, 3H), 2.18 (s, 3H)

MS (m/z): 339 (M+H)$^+$, 361 (M+Na)$^+$.

EXAMPLE 72

5-Chloro-1-methanesulfonyl-2-(2-methyl-oxiranyl)-6-trifluoromethyl-1H-indole and 1-(5-Chloro-1-methanesulfonyl-6-trifluoromethyl-1H-indol-2-yl)-ethanone

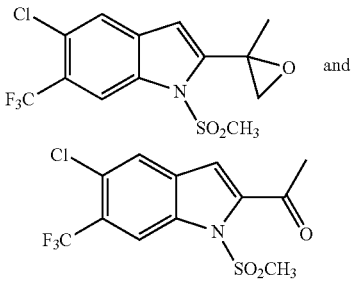

The compound prepared as in Example 71 (210 mg, 0.622 mmoL) in CH₂Cl₂ (5 mL) was treated with mCPBA (129 mg, 0.747 mmoL) at 0° C. The reaction mixture was slowly warmed to room temperature over 2 hrs. The mixture was then washed with saturated NaHCO₃, brine and dried over anhydrous Na₂SO₄, then concentrated to yield a crude white solid. The crude material was purified using column chromatography (silica gel, 3:1 hexanes:EtOAc as eluent) to yield the epoxide derivative as a white solid, along with the ketone by-product as a solid.

5-Chloro-1-methanesulfonyl-2-(2-methyl-oxiranyl)-6-trifluoromethyl-1H-indole

¹H NMR (CDCl₃, 400 MHz) δ 8.38 (s, 1H), 7.68 (s, 1H), 6.69 (s, 2H), 3.18 (s, 3H), 3.05 (m, 2H), 1.78 (s, 3H)

MS (m/z): 380 (M+Na)⁺.

1-(5-Chloro-1-methanesulfonyl-6-trifluoromethyl-1H-indol-2-yl)-ethanone

¹H NMR (CDCl₃, 400 MHz) δ 8.42 (s, 1H), 7.80 (s, 1H), 7.28 (s, 1H), 3.78 (s, 3H), 2.62 (s, 3H)

MS (m/z): 341 (M+H)⁺.

EXAMPLE 73

2-(5-Chloro-6-trifluoromethyl-1H-indol-2-yl)-1-(4-fluoro-phenylsulfanyl)-propan-2-ol

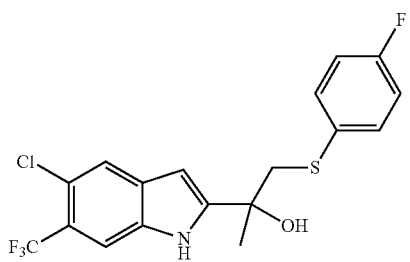 [SMILES: CC(O)(CSc1ccc(F)cc1)c1cc2cc(Cl)c(C(F)(F)F)cc2[nH]1]

4-Fluoro-phenyl thiol (55 mg, 0.425 mmoL) was treated with NaH (60%, 17 mg, 0.425 mmoL) in THF (2 mL) at 0° C. After 10 min., 5-chloro-1-methanesulfonyl-2-(2-methyl-oxiranyl)-6-trifluoromethyl-1H-indole, the epoxide derivative compound prepared as in Example 72 (100 mg, 0.425 mmoL) in THF (1 mL) was added into the reaction via syringe. The reaction was slowly warmed to room temperature. THF was removed and the residue was partitioned between CH₂Cl₂ and water. The organic layer was washed with brine and dried over anhydrous Na₂SO₄, then concentrated to yield a crude white solid. The crude material was purified using column chromatography (silica gel, 3:1 hexanes:EtOAc as eluent) to yield the title compound as a white solid.

EXAMPLE 74

2-Isopropenyl-1-methanesulfonyl-5-nitro-6-trifluoromethyl-1H-indole

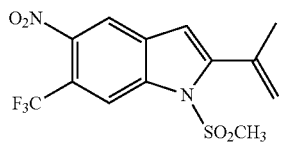

The compound prepared as in Example 4 (1.2 g, 2.08 mmoL), PdCl₂(Ph₃P)₂ (290 mg, 0.415 mmoL), CuI (80 mg, 0.415 mmoL) and Et₃N (4.16 mmoL, 0.58 mL) in THF (10 mL) was degassed with N₂ for 5 min. 2-Methyl-1-buten-3-yne (0.3 mL, 3.12 mmoL) was added dropwise into the reaction mixture via syringe at room temperature. The reaction was stirred for 3 hrs. The solvent was then removed and Et₂O was added into the residue. The mixture was then filtrated through a pad of Celite and the filtrate was washed with brine, dried over anhydrous Na₂SO₄, then concentrated to yield a crude brown oil. The crude material was purified using column chromatography (silica gel, 4:1 hexanes:EtOAc as eluent) to yield the title compound as a yellow oil.

¹H NMR (CDCl₃, 400 MHz) δ 8.52 (s, 1H), 8.12 (s, 1H), 6.68 (s, 1H), 5.45 (s, 1H), 5.32 (s, 1H), 3.08 (s, 3H)

MS (m/z): 349 (M+H)⁺.

EXAMPLE 75

1-Methanesulfonyl-2-(2-methyl-oxiranyl)-5-nitro-6-trifluoromethyl-1H-indole and 1-(1-Methanesulfonyl-5-nitro-6-trifluoromethyl-1H-indol-2-yl)-ethanone

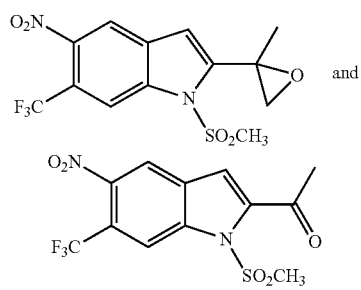

The compound prepared as in Example 9 (955 mg, 2.74 mmoL) in CH₂Cl₂ (20 mL) was treated with mCPBA (1.80 g, 8.22 mmoL) at 0° C. The reaction mixture was slowly warmed to room temperature over 2 hrs. The mixture was then washed with saturated NaHCO₃, brine and dried over anhydrous Na₂SO₄, then concentrated to yield a crude white solid. The crude material was purified using column chromatography (silica gel, 4:1 hexanes:EtOAc as eluent) to yield the epoxide derivative as a white solid, along with the ketone by-product as a solid.

1-Methanesulfonyl-2-(2-methyl-oxiranyl)-5-nitro-6-trifluoromethyl-1H-indole $^1$H NMR (CDCl$_3$, 400 MHz) δ 8.68 (s, 1H), 8.35 (s, 1H), 6.85 (s, 1H), 3.31 (s, 3H); 3.15 (m, 2H), 1.80 (s, 3H)
MS (m/z): 365 (M+H)$^+$, 387 (M+Na)$^+$.

1-(1-Methanesulfonyl-5-nitro-6-trifluoromethyl-1H-indol-2-yl)-ethanone $^1$H NMR (CDCl$_3$, 400 MHz) δ 8.71 (s, 1H), 8.32 (s, 1H), 7.40 (s, 1H), 3.75 (s, 3H), 2.70 (s, 3H)
MS (m/z): 351 (M+H)$^+$.

EXAMPLE 76

1-Isobutylsulfanyl-2-(5-nitro-6-trifluoromethyl-1H-indol-2-yl)-propan-2-ol

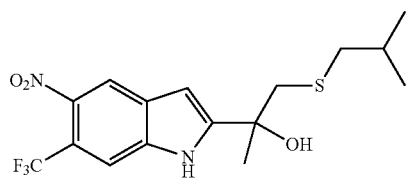 [SMILES: CC(C)CSCC(C)(O)c1cc2cc([N+](=O)[O-])c(C(F)(F)F)cc2[nH]1]

NaH (28 mg, 0.70 mmoL) was added into 2-methylpropylthiol (0.06 mL, 0.56 mmoL) in THF (2 mL) at 0° C. After bubbling ceased, the mixture was stirred for additional 30 min. 1-Methanesulfonyl-2-(2-methyl-oxiranyl)-5-nitro-6-trifluoromethyl-1H-indole, the epoxide derivative compound prepared as in Example 75, (100 mg, 0.28 mmoL) in THF (2 mL) was added dropwise and the reaction was stirred, increasing the temperature from 0° C. to room temperature. Saturated NH$_4$Cl was added to quench the reaction. THF was removed followed by addition of CH$_2$Cl$_2$ and the aqueous phase was extracted 3× with CH$_2$Cl$_2$. The combined organic phase was washed with brine, dried over anhydrous Na$_2$SO$_4$, then concentrated to yield a crude pale solid. The crude material was purified using column chromatography (silica gel, 3:1 hexanes:EtOAc as eluent) to yield the title compound as a white solid.

$^1$H NMR (CDCl$_3$, 400 MHz) δ 9.72 (br, s, 1H), 8.25 (s, 1H), 7.78 (s, 1H), 6.60 (s, 1H), 3.88 (s, 1H), 2.50 (t, J=10.5 Hz, 1H), 2.24 (d, J=10.5 Hz, 1H), 2.20 (d, J=11.0 Hz, 1H), 2.15 (d, J=11.0 Hz, 1H), 2.06 (d, J=10.5 Hz, 1H), 1.75 (s, 3H), 0.90 (d, J=10.5 Hz, 6H)
MS (m/z): 377 (M+H)$^+$.

EXAMPLE 77

4-Bromo-2-iodo-5-trifluoromethyl-phenylamine

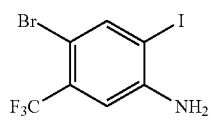

3-Trifluoro-4-bromo-aniline (5 g, 20.8 mmoL) in MeOH (10 mL) and THF (10 mL) was treated with NIS (5.16 g, 22.9 mmoL) at room temperature. After 2 hours, the reaction was quenched with saturated Na$_2$S$_2$O$_3$. The solvent was removed and the residue was partitioned between CH$_2$Cl$_2$ and water. The organic layer was washed with brine and dried over anhydrous Na$_2$SO$_4$, then concentrated to yield a crude white solid. The crude material was purified using column chromatography (silica gel, 3:1 hexanes:EtOAc as eluent) to yield the title compound as a white solid.

$^1$H NMR (CDCl$_3$, 400 MHz) δ 7.88 (s, 1H), 6.98 (s, 1H), 4.45~4.18 (br, s, 2H).

EXAMPLE 78

2-(2-Ethylsulfanyl-1-hydroxy-1-methyl-ethyl)-3-methyl-6-trifluoromethyl-1H-indole-5-carbonitrile

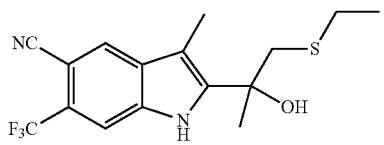

4-Amino-5-iodo-2-trifluoromethyl-benzonitrile (250 mg, 0.84 mmoL), Pd(OAc)$_2$ (0.021 mmoL, 5 mg), Ph$_3$P (0.042 mmoL, 11 mg), LiCl (0.84 mmoL, 36 mg) and KOAc (4.2 mmoL, 412 mg) were mixed together and flushed with N$_2$. DMF (10 mL) was added to the reaction and the mixture was heated to 100° C. for 6 hrs. The reaction was then cooled down and diluted with Et$_2$O. The solution was passed through a pad of Celite to remove any undissolved solids. EtOAc and H$_2$O were added. The aqueous layer was exacted 3× with Et$_2$O. The combined organic layer was washed with brine, dried over anhydrous Na$_2$SO$_4$, filtered and concentrated to yield a crude brown oil. The crude material was then purified by column chromatography (silica gel, hexanes:EtOAc 3:1 as eluent) to yield the title compound as a yellow solid.

$^1$H NMR (CDCl$_3$, 400 MHz) δ 9.18 (s, br, 1H), 8.02 (s, 1H), 7.78 (s, 1H), 3.55 (s, 1H), 3.29 (d, J=10.8 Hz, 1H), 3.04 d, J=10.8 Hz, 1H), 2.45 (abq, J=9.6 Hz, 2H), 2.38 (s, 3H), 1.72 (s, 3H), 1.23 (t, J=12.0 Hz, 3H)
MS (m/z): 343 (M+H)$^+$, 365 (M+Na)$^+$.

EXAMPLE 79

2-(5-Bromo-3-methyl-6-trifluoromethyl-1H-indol-2-yl)-1-ethylsulfanyl-propan-2-ol

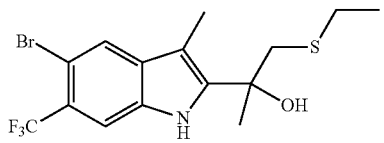 [SMILES: CCSCC(C)(O)c1[nH]c2cc(C(F)(F)F)c(C#N)cc2c1C]

The compound prepared as in Example 77 (750 mg, 2.05 mmoL), Pd(OAc)$_2$ (0.102 mmoL, 23 mg), Ph$_3$P (0.204 mmoL, 54 mg), LiCl (2.05 mmoL, 87 mg) and KOAc (10.25 mmoL, 1.01 g) were mixed together and flushed with N$_2$. DMF (10 mL) was added to the reaction and the mixture was heated to 100° C. for 6 hrs. The reaction was then cooled down and diluted with Et$_2$O. The solution was passed through a pad of Celite to remove any undissolved solids. EtOAc and H$_2$O were added. The aqueous layer was exacted 3× with Et₂O. The combined organic layer was washed with brine, dried over anhydrous Na₂SO₄, filtered and concentrated to yield a crude brown oil. The crude material was then purified by column chromatography (silica gel, hexanes:EtOAc 3:1 as eluent) to yield the title compound as a dark yellow solid.

¹H NMR (CDCl₃, 400 MHz) δ 8.85 (br, s, 1H), 7.78 (s, 1H), 7.69 (s, 1H), 3.52 (s, 1H), 3.25 (s, 1H), 3.02 (d, J=11.0 Hz, 1H), 2.50 (m, J=10.5, 2.0 Hz, 2H), 2.30 (s, 3H), 1.68 (s, 3H), 1.18 (t, J=12.5 Hz, 3H)

MS (m/z): 396, 398 (M+H)⁺.

EXAMPLE 80

1-Ethylsulfanyl-2-(3-methyl-5-nitro-6-trifluoromethyl-1H-indol-2-yl)-propan-2-ol

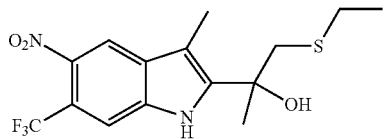 [SMILES: CCSCC(C)(O)c1[nH]c2cc(C(F)(F)F)c([N+](=O)[O-])cc2c1C]

The compound prepared as in Example 6 (320 mg, 1.053 mmoL), Pd(OAc)₂ (0.526 mmoL, 12 mg), Ph₃P (1.06 mmoL, 28 mg), LiCl (1.053 mmoL, 45 mg) and KOAc (5.265 mmoL, 517 g) were mixed together and flushed with N₂. DMF (10 mL) was added to the reaction and the mixture was heated to 100° C. for 6 hrs. The reaction was then cooled down and diluted with Et₂O. The solution was passed through a pad of Celite to remove any undissolved solids. EtOAc and H₂O were added. The aqueous layer was exacted 3× with Et₂O. The combined organic layer was washed with brine, dried over anhydrous Na₂SO₄, filtered and concentrated to yield a crude brown oil. The crude material was then purified by column chromatography (silica gel, hexanes:EtOAc 3:1 as eluent) to yield the title compound as a yellow solid.

¹H NMR (CDCl₃, 400 MHz) δ 9.29 (s, br, 1H), 8.22 (s, 1H), 7.75 (s, 1H), 3.58 (br, s, 1H), 3.25 (d, J=10.8 Hz, 1H), 3.05 (d, J=10.8 Hz, 1H), 2.38 (m, J=8.5, 7.5 Hz, 2H), 2.32 (s, 3H), 1.68 (s, 3H), 1.16 (t, J=12.0 Hz, 3H)

MS (m/z): 363 (M+H)⁺.

EXAMPLE 81

4-Amino-5-iodo-2-trifluoromethyl-benzonitrile

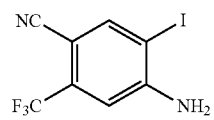

4-Amino-2-trifluoromethyl-benzonitrile (20.44 g, 109.79 mmoles) and p-toluenesulfonic acid monohydrate (1.05 g, 5.52 mmoles) were dissolved methanol (200 mL) and THF (200 mL), and the reaction mixture was stirred under a nitrogen atmosphere. The reaction vessel was wrapped in aluminium foil, while the solution was stirred for 20 min., then N-iodosuccinimide (30.41 g, 135.17 mmoles) was added and the reaction was allowed to stir overnight (16 hrs). The reaction mixture was concentrated in vacuo, triturated with hexanes (3×400 mL) and concentrated to dryness. The crude solid was dissolved in diethyl ether (400 mL), washed with water (3×), the organic extracts were diluted with hexanes (400 mL) and a white solid precipitated. The solid was filtered and dried in a vacuum oven (35° C. @ 762 Torr) overnight to yield the title compound.

¹H NMR (400 MHz, CDCl₃) δ 8.04 (s, 1H), δ 7.00 (s, 1H), δ 4.83 (br s, 2H)

MS calculated for C₈H₄F₃IN₂: 312.03, found 311 (M−H).

EXAMPLE 82

N-(4-Cyano-2-iodo-5-trifluoromethyl-phenyl)-methanesulfonamide

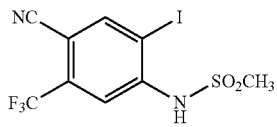

4-Amino-5-iodo-2-trifluoromethyl-benzonitrile (8.04 g, 25.77 mmoles) was dissolved in anhydrous THF (60 mL), stirred under a nitrogen atmosphere and cooled in an ice/brine bath for 20 min. 1.0 M potassium tert-butoxide in THF (82 mL, 82 mmoles) was added and the reaction mixture was stirred for 20 min. Methanesulfonyl chloride (3.2 mL, 41.18 mmoles) was then added and the reaction mixture was stirred at ambient temperature overnight. The reaction mixture was quenched with 1N HCl (90 mL) and extracted with dichloromethane (3×100 mL). The organic extracts were diluted with diethyl ether and a white solid precipitated. The solid was filtered, washed and dried to yield the title compound. The filtrate was concentrated to a crude orange solid. The compound was purified by column chromatography (SiO₂, 100% CH₂Cl₂).

¹H NMR (400 MHz, CDCl₃) δ 8.26 (s, 1H), δ 7.99 (s, 1H), δ 7.10 (s, 1H), δ 3.17 (s, 3H)

MS calculated for C₉H₆F₃IN₂O₂S: 390.12, found 389 (M−H).

EXAMPLE 83

1,1,1-Trifluoro-2-methyl-but-3-yn-2-ol

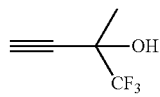

To a solution of ethynylmagnesium bromide (60 mL, 0.5 M in THF) cooled to 0° C. under nitrogen was added 1,1,1-trifluoroacetone (2.00 mL, 20.6 mmol). The solution was stirred at 0° C. for 1 hour and quenched by the cautious addition of HCl (30 mL, 1 M). After extraction with diethyl ether, the organic layer was concentrated at 35° C. on a rotary evaporator and the residue purified by flash chromatography (Silica gel, dichloromethane mobile phase) to yield the title compound as an oil, which was used in the subsequent step without further purification.

EXAMPLE 84

2-(2,2,2-Trifluoro-1-hydroxy-1-methyl-ethyl)-6-trifluoromethyl-1H-indole-5-carbonitrile (Compound #329)

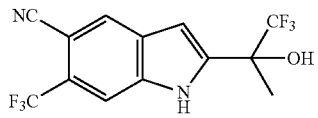 [SMILES: CC(O)(c1cc2cc(C#N)c(C(F)(F)F)cc2[nH]1)C(F)(F)F]

N-(4-Cyano-2-iodo-5-trifluoromethyl-phenyl)-methanesulfonamide (1.82 g, 4.66 mmoles), dichlorobis(triphenylphosphine)palladium (160 mg, 0.23 mmoles) and copper iodide (90 mg, 0.47 mmoles) were suspended in anhydrous THF (20 mL), under a nitrogen atmosphere. Triethylamine (1.30 mL, 9.33 mmoles) was added and after 10 min. of stirring, 1,1,1-trifluoro-2-methyl-but-3-yn-2-ol was added. The reaction mixture was stirred overnight at ambient temperature. The reaction mixture was then concentrated to a residue, which was purified by column chromatography (SiO$_2$, 100% CH$_2$Cl$_2$) to yield a semisolid.

The semisolid was dissolved in methanol (20 mL) under vigorously stirring. Then, 4.0 M sodium hydroxide solution (4.0 mL) was added. After 20 min, the reaction mixture was quenched with 1N HCl (16 mL) and extracted with diethyl ether (3×30 mL). The combined extracts were dried over MgSO$_4$, filter and concentrated in vacuo to yield the title compound as a white solid.

MS calculated for C$_{13}$H$_8$F$_6$N$_2$O: 322.05, found 321 (M–H).

EXAMPLE 85

(+) and (−) Enantiomers of 2-(2,2,2-Trifluoro-1-hydroxy-1-methyl-ethyl)-6-trifluoromethyl-1H-indole-5-carbonitrile (Compounds #334 and #335)

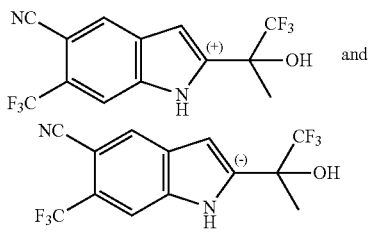

A portion of the title compound prepared as in Example 84 above, was separated into its constituent enantiomers by chiral HPLC (Chiralpak AD, isopropyl alcohol/heptane into the less polar dextrorotatory (+) compound, Compound #334 and the more polar levorotatory (−) compound Compound #335.

EXAMPLE 86

(+) and (−) Enantiomers of 2-(2-Ethylsulfanyl-1-hydroxy-1-methyl-ethyl)-6-trifluoromethyl-1H-indole-5-carbonitrile (Compounds #218 and #217)

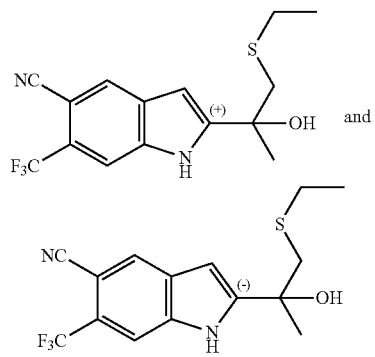

Compound #217 and Compound #218 were prepared by separating 2-(2-ethylsulfanyl-1-hydroxy-1-methyl-ethyl)-6-trifluoromethyl-1H-indole-5-carbonitrile, the compound prepared as in Example 45, by chiral HPLC (Chiralpak AD, isopropyl alcohol to yield the corresponding less polar dextrorotatory (+) compound, Compound #218 and the more polar levorotatory (−) compound, Compound #217.

EXAMPLE 87

(−) Enantiomer of 2-(2-Ethanesulfonyl-1-hydroxy-1-methyl-ethyl)-6-trifluoromethyl-1H-indole-5-carbonitrile (Compound #222)

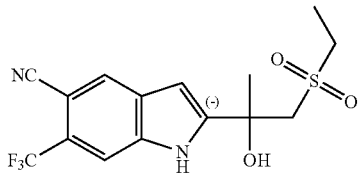 [SMILES: CCS(=O)(=O)CC(C)(O)c1cc2cc(C#N)c(C(F)(F)F)cc2[nH]1]

The (−) enantiomer of 2-(2-ethylsulfanyl-1-hydroxy-1-methyl-ethyl)-6-trifluoromethyl-1H-indole-5-carbonitrile, the compound prepared as in Example 86 above (1 equivalent) was dissolved in ethyl acetate (5 mL/mmol). A separate aqueous solution of OXONE® (3 equivalents) and Bu$_4$NHSO$_4$ (0.3 mol %) (10 mL water/g of OXONE®) was prepared and the pH of this solution adjusted to about 7 by the addition of saturated sodium bicarbonate solution. After the pH adjustment, this aqueous solution was added to the ethyl acetate solution and the resulting biphasic mixture stirred vigorously stirred. After 8 hours, an additional 3 equivalents of the pH-adjusted OXONE® solution was added and the mixture stirred overnight. Ethyl acetate (10 mL/mmol of sulfide) was added and the aqueous phase was removed. The organic phase was washed with brine, dried over anhydrous Na$_2$SO$_4$, concentrated to yield a yellow solid. This crude material (yellow solid) was purified using column chromatography (silica gel, ethyl acetate as eluent) to yield the title compound as a pale yellow solid.

X-Ray crystallographic analysis of this material indicated that the absolute configuration of the stereocenter is (R).

EXAMPLE 88

(+) and (−) Enantiomers of 2-(2-Ethylsulfanyl-1-hydroxy-1-methyl-ethyl)-3-methyl-6-trifluoromethyl-1H-indole-5-carbonitrile (Compound #234 and #233)

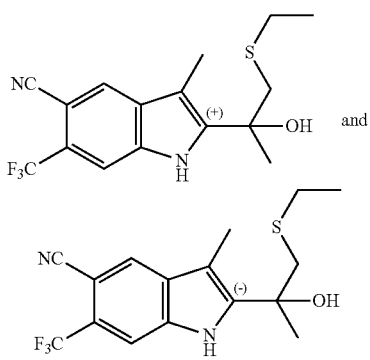

Compound #234 and Compound #233 were prepared by separating 2-(2-ethylsulfanyl-1-hydroxy-1-methyl-ethyl)-3-methyl-6-trifluoromethyl-1H-indole-5-carbonitrile, the compound prepared as in Example 78, by chiral HPLC (Chiralpak AD, 30% heptane in isopropyl alcohol into the less polar dextrorotatory (+) compound, Compound #234 and the more polar levorotatory (−) compound, Compound #223.

EXAMPLE 89

(−) Enantiomer of 2-(2-Ethanesulfonyl-1-hydroxy-1-methyl-ethyl)-3-methyl-6-trifluoromethyl-1H-indole-5-carbonitrile (Compound #251)

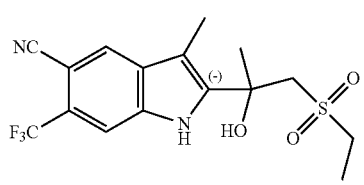 [SMILES: CCS(=O)(=O)CC(C)(O)c1[nH]c2cc(C(F)(F)F)c(C#N)cc2c1C]

The (−) enantiomer of 2-(2-ethylsulfanyl-1-hydroxy-1-methyl-ethyl)-3-methyl-6-trifluoromethyl-1H-indole-5-carbonitrile, the compound prepared as in Example 88 above (1 equivalent) was dissolved in ethyl acetate (5 mL/mmol). A separate aqueous solution of OXONE® (3 equivalents) and Bu$_4$NHSO$_4$ (0.3 mol %) (10 mL water/g of OXONE®) was prepared and the pH of this solution adjusted to about 7 by the addition of saturated sodium bicarbonate solution. After the pH adjustment, this aqueous solution was added to the ethyl acetate solution and the resulting biphasic mixture vigorously stirred. After 8 hours, an additional 3 equivalents of the pH-adjusted OXONE® solution was added and the mixture stirred overnight. Ethyl acetate (10 mL/mmol of sulfide) was added and the aqueous phase was removed. The organic phase was washed with brine, dried over anhydrous Na$_2$SO$_4$, concentrated to yield a yellow solid. This crude material (yellow solid) was purified using column chromatography (silica gel, ethyl acetate as eluent) to yield the title compound as a white solid.

EXAMPLE 90

2-(1,2-Dihydroxy-1-methyl-ethyl)-6-trifluoromethyl-1H-indole-5-carbonitrile

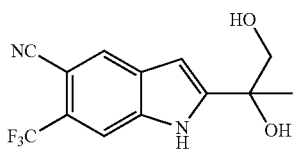 [SMILES: CC(O)(CO)c1cc2cc(C#N)c(C(F)(F)F)cc2[nH]1]

To a suspension of 2-[2-(tert-butyl-dimethyl-silanyloxy)-1-hydroxy-1-methyl-ethyl]-1-methanesulfonyl-6-trifluoromethyl-1H-indole-5-carbonitrile (9.22 g, 0.01935 mole) in methanol (150 mL), a solution of NaOH (4.64 g 0.1161 mole) in water (25 mL) was added. The resulting mixture was heated in an oil-bath at 50° C. for 4 hr and then stirred at room temperature overnight. To the reaction mixture was then added 1 N HCl until the pH was 3. The aqueous mixture was extracted with EtOAc, the organic layer was washed with water, brine, then dried over MgSO$_4$. The solvent was stripped off, the residue was triturated with DCM, and the resulting solid collected by filtration to yield the title compound as a light grey solid.

MS m/z (M−H) 283

$^1$H NMR (300 Hz, DMSO d6). δ1.50 (s. 3H), 2.50 (d, J=1.8 Hz 2H), 4.96 (t, J=5.8 Hz, 1H), 5.50 (s, 1H), 6.55 (s, 1H), 7.87 (s, 1H), 8.29 (s, 1H).

EXAMPLE 91

2-[2-(4-Cyano-phenoxy)-1-hydroxy-1-methyl-ethyl]-6-trifluoromethyl-1H-indole-5-carbonitrile (Compound #426)

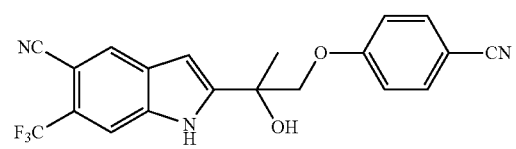 [SMILES: CC(O)(COc1ccc(C#N)cc1)c1cc2cc(C#N)c(C(F)(F)F)cc2[nH]1]

To a solution of 2-(1,2-dihydroxy-1-methyl-ethyl)-6-trifluoromethyl-1-H-indole-5-carbonitrile (209.6 mg, 0.7374 mmol) in dry DMF (4 ml) was added NaH (60 mg, 1.4749 mmol, 60% in mineral oil). After the reaction mixture was stirred at room temperature for 30 min., 4-fluorobenzonitrile (98.15 mg, 0.8115 mmol) was added, and the reaction mixture stirred at room temperature. After HPLC indicated the consumption of starting material, the reaction mixture was poured onto water and extracted with ethyl acetate. The organic layer was washed with 10% LiCl, brine and dried over MgSO$_4$. Column chromatography (EtOAc/Hexanes 50%-100%) yielded the title product as a light yellow powder.

MS: no molecular ion.

$^1$H NMR (400 Hz, MeOD). δ1.77 (s. 3H), 4.85 (s, 2H), 6.66 (s, 1H), 7.09 (d, J=9 Hz, 2H), 7.62 (d, J=9 Hz, 2H), 7.87 (s, 1H), 8.13 (s, 1H).

2-[1-Hydroxy-1-methyl-2-(3-nitro-phenoxy)-ethyl]-6-trifluoromethyl-1H-indole-5-carbonitrile, Compound #428

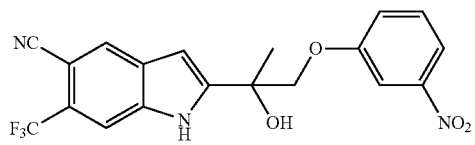 [SMILES: CC(O)(COc1cccc([N+](=O)[O-])c1)c1cc2cc(C#N)c(C(F)(F)F)cc2[nH]1]

was similarly prepared according to the procedure described in Example 91, to yield the product as a brown-yellow solid.

MS: no molecular ion $^1$H NMR (400 Hz, DMSO d6). δ1.69 (s. 3H), 4.26 (d, J=9.7 Hz, 2H), 4.33 (d, J=9.6 Hz, 2H), 6.06 (s, 1H), 6.65 (s, 1H), 7.11 (m, 1H), 7.37-7.39 (m, 1H), 7.62 (t, J=1 Hz, 1H), 7.83-7.86 (m, 1H), 7.88 (s, 1H), 8.33 (s, 1H), 12.08 (s, 1H).

2-[2-(4-Cyano-3-trifluoromethyl-phenoxy)-1-hydroxy-1-methyl-ethyl]-6-trifluoromethyl-1H-indole-5-carbonitrile, Compound #429,

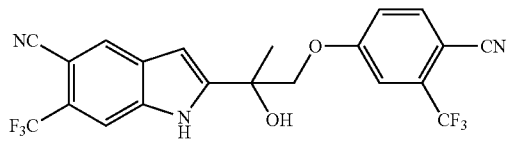 [SMILES: CC(O)(COc1ccc(C#N)c(C(F)(F)F)c1)c1cc2cc(C#N)c(C(F)(F)F)cc2[nH]1]

was similarly prepared according to the procedure described in Example 91, to yield the product as an off-white solid.

MS m/z (M−H) 452

$^1$H NMR (300 Hz, DMSO d6). δ1.68 (s. 3H), 4.36 (s, 2H), 6.10 (s, 1H), 6.67 (s, 1H), 7.44 (m, 1H), 7.49 (d, J=2.4 Hz, 1H), 7.87 (s, 1H), 8.05 (d, J=8.5 Hz, 1H), 8.32 (s, 1H).

EXAMPLE 92

In Vitro Assay-Androgen Receptor Filtration Binding Assay (PANVERA)

The assay was run on a 96 well plate with each well filled with a total reaction volume 150 μL, of a solution containing 5 pmol androgen receptor LBD (Panvera) or 30 μL of freshly prepared rat cytosol, 0.5 nM [$^3$H] R1881 tracer (NEN), 1.5 μL (10 μM) test compound or vehicle (diluted in 30% DMSO, final concentration of DMSO 0.75%) and 150 μL of TED buffer. (TED buffer contains 10 mM Tris.HCl pH 7.4, 1 mM sodium molybdate, 1.5 mM EDTA, 1 mM DTT and 10% (v/v) glycerol.)

On day one, the solution containing receptor, tracer and TED buffer was distributed into a 96 well plate. Diluted test compound or control vehicle was then added to individual wells and the plate incubated at 4° C. overnight.

On day two, to each well was then added 20 μL human γ-globulin (ICN 823102), prepared at 25 mg/ml in TE pH 8.0, and 55 μL 40% polyethylene glycol 8000 (JT Baker U222-08), prepared in TE pH 8.0. The plate was incubated at 4° C. for 60 minutes. During incubation, the harvester was rinsed with 10% PEG 8000, prepared in TE pH 8.0, and a GF/C Unifilter-96 was pre-wet with 10% PEG. The binding reaction was filtered, the retentate was washed three times with 10% PEG and dried under vacuum for a couple of minutes, then dried at 50° C. for 5 min and the plate was bottom sealed. Next, 25 μL of Microscint-20 (Packard) was added to the filter wells and the plate was top sealed. The plate wells were then counted on a TopCount (Packard).

IC$_{50}$s were determined by testing serial dilutions of the test compound (usually duplicate ten half-log dilutions starting at 10 μM) in the binding assay. Counts per well were measured and IC$_{50}$s determined by linear regression.

Representative compounds of the present invention were tested for binding to the androgen receptor according to the procedure described above with results as listed in Table A. For compounds tested more than once, each result is listed separately in the Table below.

TABLE A

| Androgen Receptor Binding (Panvera) | |
| --- | --- |
| ID No. | IC$_{50}$ (nM) |
| 1 | 14000 |
| 2 | 53000 |
| 3 | 26000 |
| 4 | 7600 |
| 5 | 39000 |
| 8 | 2650 |
| 12 | 39000 |
| 19 | >100000 |
| 20 | 23500 |
| 21 | >10200 |
| 22 | >7700 |
| 22 | >9600 |
| 23 | 54000 |
| 25 | 8800 |
| 52 | 150 |
| 53 | 1967 |
| 54 | 465 |
| 54 | 220 |
| 55 | 715 |
| 55 | 635 |
| 56 | 485 |
| 56 | 610 |
| 57 | 141 |
| 57 | 480 |
| 58 | 455 |
| 59 | 4100 |
| 60 | 6750 |
| 61 | 440 |
| 62 | 325 |
| 63 | 1550 |
| 64 | 815 |
| 65 | 945 |
| 66 | 2600 |
| 67 | 3000 |
| 68 | 19000 |
| 69 | 1200 |
| 70 | 750 |
| 75 | 9100 |
| 76 | 1244 |
| 77 | 1107 |
| 78 | 3556 |
| 79 | >9500 |
| 80 | 6400 |
| 81 | 15000 |
| 82 | 185 |
| 82 | 200 |
| 83 | 160 |

TABLE A-continued

Androgen Receptor Binding (Panvera)

| ID No. | IC$_{50}$ (nM) |
|---|---|
| 83 | 545 |
| 84 | 180 |
| 85 | 460 |
| 86 | 1250 |
| 87 | 350 |
| 87 | 1650 |
| 88 | 5150 |
| 89 | >9600 |
| 90 | >9000 |
| 91 | 1285 |
| 92 | 37000 |
| 93 | 23000 |
| 94 | 15000 |
| 95 | 3000 |
| 96 | 1710 |
| 96 | 820 |
| 97 | 7400 |
| 98 | 8500 |
| 99 | 5750 |
| 100 | 1155 |
| 101 | 3850 |
| 102 | 665 |
| 103 | 1650 |
| 104 | 930 |
| 105 | 105 |
| 106 | 225 |
| 107 | 9400 |
| 108 | 7000 |
| 109 | 2600 |
| 110 | 7700 |
| 112 | 4100 |
| 113 | 5100 |
| 114 | 4900 |
| 115 | 7700 |
| 116 | 1750 |
| 117 | 2000 |
| 253 | 335 |
| 254 | 1025 |
| 254 | 920 |
| 255 | 1255 |
| 255 | 3050 |
| 256 | 2650 |
| 257 | 5150 |
| 258 | 2450 |
| 259 | 915 |
| 260 | 2050 |
| 261 | 1457 |
| 262 | >10000 |

EXAMPLE 93

Androgen Receptor Binding Using Rat Ventral Prostate Cytosol

Rat Prostate Cytosol Preparation:

Male Sprague Dawley or Wistar rats (Charles River, 200-300 g) were used for each preparation. The day before preparing the cytosol, the rats were castrated using standard surgical procedures.

The rats were euthanized by carbon dioxide asphyxiation. The rat prostates were quickly removed and placed on ice in pre-chilled, pre-weighed 50 mL plastic tubes. No more than five prostates were placed into one tube. The tubes were then weighed and the prostate tissue wet weights calculated.

To the chilled prostate tissue was then added 1 mL/mg tissue of chilled homogenization buffer. The homogenization buffer was freshly prepared by mixing 10 mM Tris.HCl, pH 7.4, 1 mM sodium molybdate, 1.5 mM EDTA, 1 mM dithiothreitol, 10% (v/v) glycerol and 1% protease inhibitor cocktail (Sigma P 8340).

The prostate tissue was homogenized in a cold room using a pre-chilled Polytron PT3000 homogenizer (Brinkmann). Homogenization was performed at a speed setting of 20, three times for 10 sec bursts. The tubes containing the prostate tissue was kept on ice while homogenizing. The homogenate was allowed to rest on ice for 20 sec between bursts.

The homogenate was then placed into pre-chilled 3 mL polycarbonate ultracentrifuge tubes and centrifuged in the TLA-100 rotor of a TL-100 ultracentrifuge for 12 min at 100,000 rpm at 4° C. The resulting supernatant was stored in 1 mL aliquots at −80° C. until needed.

Binding to the androgen receptor was determined according to the protocol described in Example 86 using the above prepared rat cytosol.

% Inhibition was determined by testing dilutions of the test compound (usually duplicates of 10 μM) in the binding assay. Counts per well were measured and percents of inhibition determined. Androgen receptor binding IC$_{50}$s were determined by testing serial dilutions of the test compound (usually duplicate ten half-log dilutions starting at 10 μM) in the binding assay. Counts per well were measured and IC$_{50}$s determined by linear regression.

Representative compounds of the present invention were tested for binding to the androgen receptor according to the procedure described above with results as listed in Table B. For compounds tested more than once, each result is listed separately in the Table below.

TABLE B

Androgen Receptor Binding (Rat Cytosol)

| ID No. | % Inhibition | Concentration | IC$_{50}$ (nM) |
|---|---|---|---|
| 1 | 22 | 1000 nM | |
| 2 | 2.5 | 1000 nM | |
| 3 | 6.6 | 1000 nM | |
| 4 | 10.75 | 1000 nM | |
| 5 | 5.5 | 1000 nM | |
| 8 | −2 | 1000 nM | |
| 12 | 47.5 | 1000 nM | |
| 18 | 38 | 3000 nM | |
| 17 | 88 | 3000 nM | |
| 19 | −55 | 1000 nM | |
| 20 | −28.5 | 1000 nM | |
| 21 | −41.5 | 1000 nM | |
| 22 | 5.325 | 1000 nM | |
| 22 | −12.2 | 1000 nM | >7700 |
| 23 | −1.5 | 1000 nM | 6000 |
| 24 | 2 | 1000 nM | |
| 25 | −83.5 | 1000 nM | |
| 26 | 21 | 1000 nM | |
| 27 | 14 | 1000 nM | 3100 |
| 28 | −3.4 | 1000 nM | 7000 |
| 29 | −1.8 | 1000 nM | 4700 |
| 30 | −7.7 | 1000 nM | 4100 |
| 31 | 20 | 1000 nM | 4050 |
| 32 | 34 | 1000 nM | 43000 |
| 33 | 11 | 1000 nM | 29000 |
| 34 | 18 | 1000 nM | 5700 |
| 35 | −19 | 1000 nM | 4200 |
| 36 | −34 | 1000 nM | >100000 |
| 37 | 25 | 1000 nM | 3600 |
| 38 | 16 | 1000 nM | 8800 |
| 39 | 6 | 1000 nM | >6100 |
| 40 | −2.5 | 1000 nM | 3800 |
| 41 | 20 | 1000 nM | 2300 |
| 42 | 23 | 1000 nM | 7100 |
| 43 | 5.8 | 1000 nM | 9100 |
| 47 | 81 | 3000 nM | |
| 49 | 48 | 3000 nM | |
| 52 | 94.5 | 1000 nM | 79 |
| 53 | 9.75 | 1000 nM | |
| 54 | 5.5 | 1000 nM | |

TABLE B-continued

Androgen Receptor Binding (Rat Cytosol)

| ID No. | % Inhibition | Concentration | IC$_{50}$ (nM) |
|---|---|---|---|
| 55 | | | 180 |
| 55 | 5.5 | 1000 nM | |
| 56 | 38.5 | 1000 nM | |
| 57 | | | 100 |
| 57 | 78.5 | 1000 nM | |
| 58 | 79.5 | 1000 nM | |
| 59 | 67.5 | 1000 nM | 220 |
| 60 | 44.5 | 1000 nM | >10000 |
| 61 | 73 | 1000 nM | |
| 62 | 69 | 1000 nM | |
| 63 | 47.5 | 1000 nM | |
| 64 | 61.5 | 1000 nM | |
| 65 | 47.5 | 1000 nM | |
| 66 | −12 | 1000 nM | |
| 67 | 25.5 | 1000 nM | |
| 68 | 36 | 1000 nM | |
| 69 | 31 | 1000 nM | |
| 70 | 33.65 | 1000 nM | |
| 75 | 13.15 | 1000 nM | |
| 76 | −30.5 | 1000 nM | |
| 77 | −9.25 | 1000 nM | |
| 78 | 16.56 | 1000 nM | |
| 79 | 48.5 | 1000 nM | |
| 80 | −24.95 | 1000 nM | |
| 81 | 5.2 | 1000 nM | |
| 82 | 69.75 | 1000 nM | 640 |
| 82 | 83 | 1000 nM | |
| 83 | 69 | 1000 nM | |
| 83 | | | 120 |
| 84 | 86 | 1000 nM | 240 |
| 85 | 78.5 | 1000 nM | 110 |
| 85 | 89 | 1000 nM | |
| 86 | 72.5 | 1000 nM | 240 |
| 87 | 85 | 1000 nM | |
| 87 | 61.5 | 1000 nM | 120 |
| 88 | −17.45 | 1000 nM | |
| 90 | −2.5 | 1000 nM | |
| 91 | 36 | 1000 nM | |
| 92 | 14.68 | 1000 nM | |
| 93 | 35 | 1000 nM | |
| 94 | 21.8 | 1000 nM | |
| 95 | 56.5 | 1000 nM | |
| 96 | 74 | 1000 nM | |
| 96 | 59 | 1000 nM | |
| 97 | 25 | 1000 nM | |
| 98 | −31 | 1000 nM | |
| 99 | 8.5 | 1000 nM | |
| 100 | 80 | 1000 nM | |
| 101 | −24.94 | 1000 nM | |
| 102 | 73.5 | 1000 nM | 140 |
| 104 | 94.5 | 1000 nM | |
| 104 | 110 | 3000 nM | |
| 105 | 61.5 | 1000 nM | 98 |
| 106 | 63 | 1000 nM | 300 |
| 107 | 1.5 | 1000 nM | |
| 108 | 17.5 | 1000 nM | |
| 109 | 49 | 1000 nM | |
| 110 | 58.5 | 1000 nM | |
| 112 | 39.5 | 1000 nM | |
| 113 | −17.5 | 1000 nM | |
| 113 | 75.5 | 1000 nM | |
| 114 | 61 | 1000 nM | |
| 115 | 54.5 | 1000 nM | 1300 |
| 116 | 28.4 | 1000 nM | |
| 117 | 32.5 | 1000 nM | |
| 118 | 80.5 | 3000 nM | |
| 120 | 130 | 3000 nM | |
| 121 | 86 | 3000 nM | |
| 122 | 83.5 | 3000 nM | |
| 123 | 77 | 3000 nM | |
| 123 | 15 | 3000 nM | |
| 124 | 66.5 | 3000 nM | |
| 124 | 4.4 | 3000 nM | |
| 125 | 21 | 3000 nM | |
| 126 | −30 | 3000 nM | |
| 127 | −35 | 3000 nM | |
| 127 | 36 | 3000 nM | |
| 128 | 25 | 3000 nM | |
| 129 | 39.5 | 3000 nM | |
| 130 | 32.55 | 3000 nM | |
| 131 | 120 | 3000 nM | |
| 132 | 64.5 | 3000 nM | |
| 133 | 54 | 3000 nM | |
| 135 | 130 | 3000 nM | |
| 136 | 38 | 3000 nM | |
| 137 | 57.5 | 3000 nM | |
| 138 | 110 | 3000 nM | |
| 139 | 87.5 | 3000 nM | |
| 139 | 31.5 | 3000 nM | |
| 140 | 47 | 3000 nM | |
| 141 | −4.5 | 3000 nM | |
| 142 | 92 | 3000 nM | |
| 143 | 14 | 3000 nM | |
| 144 | 79 | 3000 nM | |
| 145 | 58 | 3000 nM | |
| 147 | 68 | 3000 nM | |
| 148 | 94 | 3000 nM | |
| 149 | 94 | 3000 nM | |
| 149 | 77 | 3000 nM | |
| 150 | 120 | 3000 nM | |
| 151 | 100 | 3000 nM | |
| 152 | 97 | 3000 nM | |
| 154 | 29 | 3000 nM | |
| 155 | −6.1 | 3000 nM | |
| 156 | 66 | 3000 nM | |
| 156 | 67 | 3000 nM | |
| 158 | 52 | 3000 nM | |
| 159 | 93 | 3000 nM | |
| 160 | 65 | 3000 nM | |
| 161 | 39 | 3000 nM | |
| 162 | 0.69 | 3000 nM | |
| 164 | 52 | 3000 nM | |
| 165 | 52 | 3000 nM | |
| 168 | 41 | 3000 nM | |
| 169 | 62 | 3000 nM | |
| 170 | 80 | 3000 nM | |
| 171 | 18 | 3000 nM | |
| 171 | | | 320 |
| 173 | 32 | 3000 nM | |
| 176 | 90 | 3000 nM | |
| 253 | 33.5 | 1000 nM | |
| 254 | | | 670 |
| 254 | 41 | 1000 nM | |
| 255 | 26 | 1000 nM | |
| 258 | 35.4 | 1000 nM | |
| 261 | 14.05 | 1000 nM | |
| 262 | −8.4 | 1000 nM | |
| 265 | 93.5 | 3000 nM | |
| 266 | 12.4 | 3000 nM | |
| 267 | 79 | 3000 nM | |
| 267 | 28 | 3000 nM | |
| 268 | −3.3 | 3000 nM | |

EXAMPLE 94

COS-7 Whole-Cell Androgen Receptor Binding Assay, Adenovirus Transduction

Day One:

COS-7 cells were plated in 96-well plates at 20,000 cells per well, in a solution of DMEM/F12 (GIBCO) containing 10% (v/v) charcoal-treated fetal bovine serum (Hyclone) and lacking phenol red. The cells were then incubated overnight at 37° C. in 5% (v/v) humidified $CO_2$.

Day Two:

Test compound solutions were prepared by diluting the test compound in 100% (v/v) DMSO, if necessary. Each dilution yielded a solution which was 625× the final desired test concentration.

Next, 1 mL of DMEM/F12 lacking phenol red was pipetted into each of the wells of a 2-mL 96-well assay block. Then 4 µL of the 625× test compound dilutions were pipetted into each well of the assay block. The wells were carefully mixed by pipette.

In a 15 mL or 50 mL sterile centrifuge tube, a 2.5 nM dilution of tritiated methyl-trienolone in DMEM/F12 lacking phenol red ([$^3$H]R1881; Perkin-Elmer) was prepared.

In a 15 mL or 50 mL sterile centrifuge tube, a dilution in DMEM/F12 of the adenovirus AdEasy+rAR at a moi of 1:50 per well was prepared.

The medium was removed from the 96-well plates by inversion and the plates dried very briefly, inverted, on a sterile towel. As soon as possible after medium removal, 40 µL of the diluted test compound was added to each well, in duplicate. To each well was then added 40 µL of the 2.5 nM [$^3$H]R1881 and 20 µL of the diluted adenovirus. The plates were then incubated for 48 hours at 37° C. in 5% (v/v) humidified $CO_2$.

Day Four:

The medium was removed from the above incubated plates by inversion and dried. Each well was then washed with 0.35 mL of 1×PBS. The PBS was then removed from the plates by inversion and the plates dried.

To each well was then added 50 µL of 0.5% (v/v) Triton X-100 (Sigma) in 1×PBS and the plates placed on a rotary shaker for 5 min. The contents of each well were then transferred to an OptiPlate-96 (Packard) scintillation plate. To each well was then added 0.2 mL of Microscint-20 (Packard) and the wells counted on a TopCount (Packard).

Percent inhibition was determined by testing dilutions of the test compound (usually duplicates of 10 µM) in the binding assay. Counts per well were measured and percents of inhibition determined. Androgen receptor binding $IC_{50}$s were determined by testing serial dilutions of the test compound (usually duplicate ten half-log dilutions starting at 10 µM) in the binding assay. Counts per well were measured and $IC_{50}$s determined by linear regression.

Representative compounds of the present invention were tested for binding to the androgen receptor according to the procedure described above with results as listed in Table C. Unless otherwise noted, COS binding % inhibition was determined using a concentration of 3000 nM. For compounds tested more than once, each result is listed separately in the Table below.

TABLE C

| ID No. | COS Binding % Inhibition | $IC_{50}$ (nM) |
|---|---|---|
| 10 | | >3000 |
| 11 | | >3000 |
| 17 | | >1500 |
| 47 | 78 | >1000 |
| 49 | 30 | >3000 |
| 50 | 7 | |
| 51 | 54 | |
| 104 | 94 | 1000 |
| 118 | | >1500 |
| 118 | 62 | >1300 |
| 120 | 86 | 205 |
| 121 | 72 | >1800 |
| 122 | 66 | >1600 |
| 123 | 82 | >1800 |
| 123 | 32 | >3000 |
| 124 | 54 | >880 |
| 124 | 11 | >3000 |
| 125 | 30 | |
| 126 | 29 | |
| 127 | 41 | |
| 127 | 74 | >1200 |
| 128 | 21 | >1500 |
| 129 | 10 | |
| 130 | −8 | |
| 131 | 84 | >1600 |
| 132 | 8.7 | >3000 |
| 133 | 65 | >1500 |
| 134 | | >10000 |
| 135 | 98 | 320 |
| 136 | 4.8 | 526.7 |
| 137 | 73 | >1500 |
| 138 | 78 | 317 |
| 139 | 94 | 63 |
| 139 | 97 | 252.5 |
| 140 | 51.5 | >1500 |
| 141 | 42 | |
| 141 | | >3000 |
| 142 | 90 | 220 |
| 143 | 68 | >1500 |
| 144 | | 375 |
| 145 | 84.7 | 36.7 |
| 147 | 6.1 | >3000 |
| 148 | 32 | >2400 |
| 149 | 63 | 780 |
| 149 | 78 | >790 |
| 150 | 81 | 165 |
| 150 | 74 | 626.5 |
| 151 | | >970 |
| 151 | 55 | 2185.5 |
| 152 | 39 | 108 |
| 154 | 50 | |
| 155 | 35 | |
| 156 | 42 | >1000 |
| 156 | 52 | >1000 |
| 158 | 62 | 160 |
| 158 | 56 | 550 |
| 159 | 90 | 240 |
| 160 | 84 | 250 |
| 161 | 20 | |
| 162 | 56 | |
| 164 | 68 | >1000 |
| 165 | 69 | >3000 |
| 166 | | 3000 |
| 167 | | >3000 |
| 168 | 60 | >3000 |
| 169 | 90 | 48 |
| 170 | 67 | >3000 |
| 171 | 92 | 145 |
| 171 | 94 | |
| 173 | 17 | >3000 |
| 175 | | >3000 |
| 176 | 75 | 1500 |
| 177 | 90 | 88 |
| 180 | 24 | |
| 185 | 92 | 61 |
| 189 | 100 | 280 |
| 190 | 100 | 292 |
| 191 | 65 | 840 |
| 192 | 86 | 82 |
| 194 | 80 | 320 |
| 196 | 53 | |
| 197 | 86 | >3000 |
| 198 | 55 | |
| 199 | 82 | 310 |
| 200 | 97 | 1000 |
| 201 | 86 | 340 |
| 202 | 50 | |
| 206 | −40 | |
| 207 | −35 | |
| 207 | 39 | |
| 208 | −26 | |
| 208 | −22 | |
| 209 | 61 | 1843.3 |
| 211 | 43 | |

TABLE C-continued

COS Binding

| ID No. | % Inhibition | IC$_{50}$ (nM) |
|---|---|---|
| 212 | 86 | 98 |
| 213 | 71 | >600 |
| 214 |  | >3000 |
| 217 |  | 792.4 |
| 217 | 38 | >3000 |
| 217 | 61 | 493.1 |
| 217 | 69 | 149.1 |
| 219 |  | 6.2 |
| 220 |  | 34 |
| 222 | 42 | 1584 |
| 225 | 82 | 141.6 |
| 230 | 49 |  |
| 231 | 73 | 665 |
| 231 | 78 | >3000 |
| 233 | 95 | 45.6 |
| 233 | 81 |  |
| 234 | 71 | 539.4 |
| 235 | 78 | 519.7 |
| 236 | 83 | 105 |
| 240 | 48 |  |
| 241 | 48 |  |
| 242 | 92 | 305.1 |
| 244 | 32 |  |
| 245 | 47 |  |
| 246 | 70 | 616.2 |
| 247 | 90 | 60.7 |
| 248 | 24 |  |
| 250 | 79 |  |
| 251 | 85 | 220 |
| 252 | 68 | >3000 |
| 265 | 86 | 585 |
| 266 | 38 |  |
| 267 | 75 | 264 |
| 267 | 79 | 89.6 |
| 268 | 42 |  |

EXAMPLE 95

L929 Androgen Receptor Functional Assay, Adenovirus Transduction

Day One:

L929 cells were plated in 96-well plates at 20,000 cells per well, in DMEM/F12 (GIBCO) containing 10% (v/v) charcoal-treated fetal bovine serum (Hyclone) and lacking phenol red. The plates were then incubated overnight at 37° C. in 5% (v/v) humidified $CO_2$.

Day Two:

Test compound dilutions were prepared in 100% (v/v) DMSO, if necessary. Each dilution was made to 1250× the final desired assay concentration.

First, 2 mL of DMEM/F12 lacking phenol red was pipetted into the wells of a 2-mL 96-well assay block. Next, 4 µL of the 1250× test compound dilutions were pipetted into each well of the assay block. The mixtures within the well were then carefully mixed by pipette.

In a 15 mL or 50 mL sterile centrifuge tube, a 2.5 nM (2.5×) dilution of R1881 (methyl-trienolone) in DMEM/F12 lacking phenol red was prepared.

In a second 15 mL or 50 mL centrifuge tube a solution containing an equal volume of DMEM to the first and an equal volume of 100% (v/v) DMSO to the volume of R1881 used in the first tube was prepared.

In a 15 mL or 50 mL sterile centrifuge tube, a dilution in DMEM/F12 of the adenovirus AdEasy+rAR at an moi of 1:500 per well was prepared.

The medium was removed from the 96-well plates by inversion and dried, inverted, very briefly. As soon as possible after medium removal, 40 µL of the diluted unlabeled test compound was added to each well, in duplicate. To each well designated for antagonist testing was added 40 µL of the 2.5 nM R1881 dilution to the wells for antagonist testing. To each well designated for agonist testing was added 40 µL of the DMSO dilution. Then 20 µL of the diluted adenovirus were added to all wells. The plates were incubated for 48 hours at 37° C. in 5% (v/v) humidified $CO_2$.

Day Four:

To each well was added 100 µL of Steady-Glo luciferase assay substrate (Promega) and the plates were placed on a rotary shaker for 1 min. The plates were then incubated at room temperature in the dark for one hour. The contents of each well were then transferred to a white microtiter plate (Packard) and read on a Luminoskan Ascent (Thermo Lab Systems).

L929 AR percent activity was determined by testing dilutions of the test compound using a concentration of 3000 nM unless otherwise noted. L929 percent inhibition was determined by testing dilutions of the test compound using a concentration of 3000 nM. EC$_{50}$s and IC$_{50}$s were determined by testing serial dilutions of the test compound (usually duplicate ten half-log dilutions starting at 10 µM). Luciferase activity per well were measured and EC$_{50}$s and IC$_{50}$s determined by linear regression.

Representative compounds of the present invention were tested for functional activity at the androgen receptor according to the procedure described above with results as listed in Table D. For compounds tested more than once, each result is listed separately in the Table below.

TABLE D

L929 ANDROGEN RECEPTOR FUNCTIONAL ASSAY

| ID No. | % Activity | % Inhibition | EC$_{50}$ (nM) | IC$_{50}$ (nM) |
|---|---|---|---|---|
| 47 | 2 | 75 |  |  |
| 49 | 2 | 8 |  |  |
| 50 | 2 | 36 |  |  |
| 51 | 2 | −39 |  |  |
| 104 | 9 | 18 |  |  |
| 118 | −2 @ 8000 nM | 63 | >8000 | 3067.5 |
| 120 | −5 | 44 |  |  |
| 121 | −4 | 54 |  |  |
| 122 | 10 | 35 |  |  |
| 123 | −4 | 1 |  |  |
| 123 | 1 @ 8000 nM | 30 |  |  |
| 124 | −4 | 20 |  |  |
| 124 | −4 | 99 |  |  |
| 125 | −5 | 28 |  |  |
| 126 | −5 | 25 |  |  |
| 127 | −5 | 66 |  |  |
| 127 | −5 | 32 |  |  |
| 128 | −4 | 44 |  |  |
| 129 | −5 | −8 |  |  |
| 130 | −5 | 46 |  |  |
| 131 | −5 | −4 |  |  |
| 132 | −5 | 48 |  |  |
| 133 | −4 | 19 |  |  |
| 135 | 0 | 40 |  |  |
| 136 | 0 | 75 |  |  |
| 137 | 0 | 77 |  |  |
| 138 | 0 | 19 |  |  |
| 139 | 0 | 43 |  |  |
| 139 | 1 | 91 |  |  |
| 140 | 0 | 78 |  |  |
| 141 | 0 | 42 |  |  |
| 142 | 0 | 78 |  |  |
| 143 | 0 | 67 |  |  |
| 144 | 0 | 82 |  |  |
| 145 | 1 | 94 |  |  |
| 147 | 0 | 43 |  |  |
| 148 | 0 | 77 |  |  |

TABLE D-continued

L929 ANDROGEN RECEPTOR FUNCTIONAL ASSAY

| ID No. | % Activity | % Inhibition | $EC_{50}$ (nM) | $IC_{50}$ (nM) |
| --- | --- | --- | --- | --- |
| 149 | 2 | 77 | | |
| 150 | 0 @ 8000 nM | | >8000 | 303.4 |
| 151 | −1 @ 8000 nM | | >8000 | 533.4 |
| 154 | 2 | 7 | | |
| 155 | 2 | −2 | | |
| 156 | 2 | 35 | | |
| 156 | 2 | 23 | | |
| 158 | 3 | 21 | | |
| 158 | 2 | 29 | | |
| 159 | 2 | 82 | | |
| 160 | 1 | 76 | | |
| 161 | 2 | 24 | | |
| 162 | 2 | 64 | | |
| 164 | 2 | 71 | | |
| 165 | 1 | 100 | | |
| 168 | 3 | 26 | | |
| 169 | 2 | 98 | | |
| 170 | 2 | 67 | | |
| 171 | −1 @ 8000 nM | 101 | >8000 | 366 |
| 171 | 11 | 70 | | |
| 173 | 2 | 40 | | |
| 176 | 3 | 81 | | |
| 177 | 2 | 89 | | |
| 180 | 2 | −11 | | |
| 185 | 2 | 97 | | |
| 189 | 3 | 85 | | |
| 190 | 1 | 97 | | |
| 191 | 2 | −6 | | |
| 192 | 8 | 89 | | |
| 194 | 2 | 40 | | |
| 196 | 13 | −119 | | |
| 197 | 2 | −26 | | |
| 198 | 7 | 24 | | |
| 199 | 2 | 59 | | |
| 200 | 1 | 96 | | |
| 201 | 2 | 83 | | |
| 202 | 1 | 21 | | |
| 206 | 5 | 88 | | |
| 207 | 1 | 101 | | |
| 207 | −1 | 101 | >8000 | 492.2 |
| 208 | 1 | 24 | | |
| 209 | −3 @ 8000 nM | 87 | >8000 | 372.4 |
| 211 | −1 | 88 | | |
| 212 | −3 | 101 | | |
| 213 | −1 @ 8000 nM | 92 | >8000 | 371.8 |
| 217 | 0 @ 8000 nM | 87 | >8000 | 969.4 |
| 217 | | | | 414.7 |
| 217 | 5 | 80 | | 810 |
| 218 | 0 | 62 | | |
| 219 | −3 | 103 | | |
| 220 | −3 | 103 | | |
| 221 | −1 | 23 | | |
| 222 | 0 @ 8000 nM | 61 | >8000 | 2406.7 |
| 223 | 0 @ 8000 nM | 100 | >8000 | 277.4 |
| 225 | 1 | 97 | | 228.9 |
| 230 | 0 | 45 | | |
| 231 | 0 | 75 | | 3184.4 |
| 231 | −1 | 37 | | |
| 233 | 0 | 97 | | 69.2 |
| 234 | −1 | 99 | | 214.6 |
| 235 | 3 | 95 | | 1842.7 |
| 236 | 2 | 103 | | 821.3 |
| 240 | 0 | 47 | | |
| 251 | −1 | 90 | | 200 |
| 252 | 1 | 65 | | 3100 |
| 265 | −1 | 65 | | |
| 266 | −4 | 65 | | |
| 267 | −5 | −13 | | |
| 267 | 0 | 19 | | |
| 268 | 9 | 83 | | |

EXAMPLE 96

Ventral Prostate and Seminal Vesicle Weight In Vivo Assay

Immature (approximately 50 g) castrated male Sprague Dawley rats (Charles River) were treated once daily for five days with test compound (usually given orally at 40 mg/kg in a volume of 0.3 mL, in 30% cyclodextrin or 0.5% methylcellulose vehicle) and with testosterone propionate (given subcutaneously by injection at the nape of the neck at 2 mg/kg, in a volume of 0.1 mL in sesame oil). On the sixth day, the rats were euthanized by asphyxiation in carbon dioxide. Ventral prostates and seminal vesicles were removed and their wet weights determined. Test compound activity was determined as the percent inhibition of testosterone-enhanced tissue weights, with a vehicle-treated control group set to zero percent and a testosterone alone-treated control group set to 100%.

A test compound was said to be "active" if the non weight adjusted prostate weight was ≤40 mg or the % Inhibition prostate weight, body weight adjusted was ≥40% @ 2 mg/day dosage. $ID_{50}$'s, if determined, of ≤15 mg/day also indicated an "active" compound.

Compounds #136, 139, 140, 142, 143, 159, 165, 167, 169, 170, 171, 171, 175, 176, 177, 181, 185, 190, 191, 192, 202, 205, 206, 207, 208, 209, 212, 213, 217, 222, 223, 224, 225, 230, 231, 232, 233, 236, 237, 243, 244, 250, 251, 252, 275, 276, 277, 278, 284, 288, 289, 291, 319, 327, 329, 330, 331, 332, 333, 334, 335, 344, 345, 347, 349, 354, 357 and 404 were tested according to the procedure described above and determined to be "active".

Compounds #6, 7, 9, 10, 11, 13, 14, 15, 17, 18, 47, 49, 50, 51, 85, 104, 113, 118, 123, 124, 126, 127, 129, 131, 133, 134, 135, 137, 138, 141, 146, 152, 153, 155, 156, 158, 160, 161, 162, 164, 166, 168, 173, 180, 189, 194, 196, 197, 198, 199, 200, 201, 204, 218, 219, 220, 221, 228, 234, 235, 240, 241, 242, 245, 247, 266, 267, 268, 269, 270, 273, 274, 279, 280, 281, 282, 285, 285, 287, 290, 294, 295, 317, 318, 322, 323, 324, 325, 326, 353, 397, 403, 405, 407, 408, 410, 411, 412, 413, 414, 415, 426, 428, 429, 445 and 446 were tested according to the procedure described above and determined to be "inactive". Note that while certain of these compounds may or may not have shown an effect on prostate and/or vesical weight, they are listed herein as "inactive" as they did not meet the specified criteria defined above.

EXAMPLE 97

As a specific embodiment of an oral composition, 50 mg of Compound #222 prepared as described above is formulated with sufficient finely divided lactose to provide a total amount of 580 to 590 mg to fill a size 0 hard gel capsule.

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

We claim:
1. A method of inhibiting an androgen receptor, in a subject in need thereof comprising administering to the subject a therapeutically effective amount of the compound of formula (III)

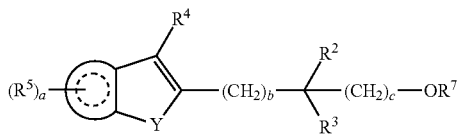

(III)

wherein

is a six membered heteroaryl ring structure containing one to two nitrogen atoms;

Y is $NR^1$;

$R^1$ is selected from the group consisting of hydrogen, lower alkyl, fluorinated lower alkyl, —$SO_2$-(lower alkyl), —$SO_2$-phenyl, —$SO_2$-tolyl, —$(CH_2)$-(fluorinated lower alkyl), -(lower alkyl)-CN, -(lower alkyl)-C(O)—O-(lower alkyl), -(lower alkyl)-O-(lower alkyl) and -(lower alkyl)—$S(O)_{0-2}$-(lower alkyl);

$R^4$ is selected from the group consisting of hydrogen, halogen, lower alkyl, lower alkenyl, lower alkynyl and cyano; wherein the lower alkyl, lower alkenyl or lower alkynyl is optionally substituted on the terminal carbon atom with —Si(lower alkyl)$_3$;

a is an integer from 0 to 4;

$R^5$ is selected from the group consisting halogen, hydroxy, carboxy, lower alkyl, halogen substituted lower alkyl, lower alkoxy, halogen substituted lower alkoxy, cyano, nitro, amino, lower alkylamino, di(lower alkyl)amino, —C(O)-(lower alkyl), —C(O)-(lower alkoxy), —C(O)—N($R^4$)$_2$, —S(O)$_{0-2}$-(lower alkyl), —$SO_2$—N($R^4$)$_2$, —N($R^4$)—C(O)-(lower alkyl), —N($R^4$)—C(O)-(halogen substituted lower alkyl) and aryl;

wherein each $R^4$ is independently selected from hydrogen or lower alkyl;

wherein the aryl is optionally substituted with one or more substituents independently selected from halogen, hydroxy, carboxy, lower alkyl, halogen substituted lower alkyl, lower alkoxy, halogen substituted lower alkoxy, cyano, nitro, amino, lower alkylamino or di(lower alkyl)amino;

b is an integer from 0 to 1;

c is an integer from 0 to 1;

$R^7$ is selected from the group consisting of hydrogen, lower alkyl and —Si(lower alkyl)$_3$;

$R^2$ is selected from the group consisting of hydrogen, lower alkyl, halogen substituted lower alkyl and —$(CH_2)_{1-4}$—Z—$R^6$;

$R^3$ is selected from the group consisting of lower alkyl, halogen substituted lower alkyl and —$(CH_2)_{1-4}$—Z—$R^6$;

wherein each Z is independently selected from the group consisting of —$S(O)_{0-2}$—, —O—, —O—C(O)—, —NH— and —N(lower alkyl)-;

wherein each $R^6$ is independently selected from the group consisting of lower alkyl, halogen substituted lower alkyl lower alkenyl, aryl, aralkyl, biphenyl, cycloalkyl, cycloalkyl-(lower alkyl), heteroaryl and heteroaryl-(lower alkyl);

wherein the cycloalkyl, aryl or heteroaryl group, whether alone or part of a substituent group is optionally substituted with one or more substituents independently selected from halogen, hydroxy, carboxy, lower alkyl, halogen substituted lower alkyl, lower alkoxy, cyano, nitro, amino, lower alkylamino, di(lower alkyl) amino, —$S(O)_{0-2}$-(lower alkyl) and —$SO_2$—N($R^4$)$_2$;

provided that when Z is O, NH or N(lower alkyl) then Z is other than lower alkenyl;

or a pharmaceutically acceptable salt thereof.

* * * * *